United States Patent
Fraser et al.

(10) Patent No.: US 7,521,420 B2
(45) Date of Patent: *Apr. 21, 2009

(54) MACROCYCLIC ANTAGONISTS OF THE MOTILIN RECEPTOR

(75) Inventors: Graeme L. Fraser, Sherbrooke (CA); Éric Marsault, Sherbrooke (CA); Mark Peterson, Sherbrooke (CA); Hamid Hoveyda, Sherbrooke (CA); Sylvie Beaubien, Sherbrooke (CA); Kamel Benakli, Montreal (CA); Robert Dèziel, Town of Mount Royal (CA)

(73) Assignee: Tranzyme Pharma, Inc., Quebec (CA)

( * ) Notice: Subject to any disclaimer, the term of this patent is extended or adjusted under 35 U.S.C. 154(b) by 40 days.

This patent is subject to a terminal disclaimer.

(21) Appl. No.: 10/872,142

(22) Filed: Jun. 18, 2004

(65) Prior Publication Data
US 2005/0054562 A1    Mar. 10, 2005

Related U.S. Application Data

(60) Provisional application No. 60/479,223, filed on Jun. 18, 2003.

(30) Foreign Application Priority Data
Jun. 18, 2004 (CA) ............... PCT/CA04/00913

(51) Int. Cl.
*A61K 38/12* (2006.01)
*C07K 5/12* (2006.01)
*C07K 1/00* (2006.01)

(52) U.S. Cl. .................. 514/11; 530/317; 530/333
(58) Field of Classification Search .............. None
See application file for complete search history.

(56) References Cited

U.S. PATENT DOCUMENTS

| | | | |
|---|---|---|---|
| 4,920,102 A | 4/1990 | Gidda et al. |
| 4,997,820 A | 3/1991 | Sutter et al. |
| 5,008,249 A | 4/1991 | Omura et al. |
| 5,143,915 A | 9/1992 | Rovnyak et al. |
| 5,175,150 A | 12/1992 | Omura et al. |
| 5,179,087 A | 1/1993 | Donald et al. |
| 5,196,452 A | 3/1993 | Hwang et al. |
| 5,252,579 A | 10/1993 | Skotnicki et al. |
| 5,292,741 A | 3/1994 | Delaszlo et al. |
| 5,376,663 A | 12/1994 | Cooper et al. |
| 5,380,888 A | 1/1995 | Sum et al. |
| 5,418,224 A | 5/1995 | Hoeltje et al. |
| 5,422,341 A | 6/1995 | Macielag et al. |
| 5,426,103 A | 6/1995 | Macpherson et al. |
| 5,432,261 A | 7/1995 | Kurono et al. |
| 5,457,111 A | 10/1995 | Luly et al. |
| 5,457,194 A | 10/1995 | Luly et al. |
| 5,459,049 A | 10/1995 | Kurono et al. |
| 5,470,830 A | 11/1995 | Macielag et al. |
| 5,470,961 A | 11/1995 | Harada et al. |
| 5,523,401 A | 6/1996 | Freiberg et al. |
| 5,530,119 A | 6/1996 | Kawai et al. |
| 5,530,120 A | 6/1996 | Luly et al. |
| 5,534,632 A | 7/1996 | Or et al. |
| 5,538,961 A | 7/1996 | Freiberg et al. |
| 5,554,605 A | 9/1996 | Freiberg et al. |
| 5,561,137 A | 10/1996 | Or et al. |
| 5,561,139 A | 10/1996 | Luly et al. |
| 5,561,140 A | 10/1996 | Kawai et al. |
| 5,561,228 A | 10/1996 | Or et al. |
| 5,563,172 A | 10/1996 | Wagner et al. |
| 5,599,927 A | 2/1997 | Or et al. |
| 5,604,234 A | 2/1997 | Or et al. |
| 5,604,294 A | 2/1997 | Luly et al. |
| 5,612,350 A | 3/1997 | Or et al. |
| 5,624,949 A | 4/1997 | Heath, Jr. et al. |
| 5,643,918 A | 7/1997 | Wagner et al. |
| 5,658,888 A | 8/1997 | Koga et al. |
| 5,696,108 A | 12/1997 | Heath, Jr. et al. |
| 5,698,578 A | 12/1997 | Heath, Jr. et al. |
| 5,708,002 A | 1/1998 | Luly et al. |
| 5,710,145 A | 1/1998 | Engel et al. |
| 5,712,253 A | 1/1998 | Lartey et al. |
| 5,719,175 A | 2/1998 | Heath, Jr. et al. |

(Continued)

FOREIGN PATENT DOCUMENTS

WO    WO-95/21186    8/1995

(Continued)

OTHER PUBLICATIONS

S.R. Vippagunta, et al. Adv. Drug Delivery Rev. (2001) 48, pp. 3-26.*

*Primary Examiner*—Andrew D Kosar
(74) *Attorney, Agent, or Firm*—Myers Bigel Sibley & Sajovec, PA

(57) ABSTRACT

The present invention is directed to novel macrocyclic compounds of formula (I) and their pharmaceutically acceptable salts, hydrates or solvates:

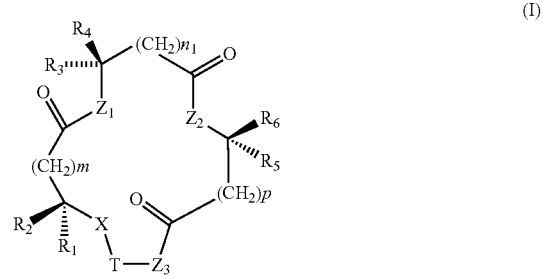

(I)

wherein $R_1$, $R_2$, $R_3$, $R_4$, $R_5$, $R_6$, $n_1$, m, p $Z_1$, $Z_2$, and $Z_3$ are as describe in the specification. The invention also relates to compounds of formula (I) which are antagonists of the motilin receptor and are useful in the treatment of disorders associated with this receptor and with or with motility dysfunction.

12 Claims, 21 Drawing Sheets

U.S. PATENT DOCUMENTS

| | | | |
|---|---|---|---|
| 5,731,320 | A | 3/1998 | Wagner et al. |
| 5,734,012 | A | 3/1998 | Dharanipragada et al. |
| 5,811,515 | A | 9/1998 | Grubbs et al. |
| 5,817,807 | A | 10/1998 | Bridger et al. |
| 5,849,691 | A | 12/1998 | Majer et al. |
| 5,854,407 | A | 12/1998 | Harada et al. |
| 5,888,971 | A | 3/1999 | Greco et al. |
| 5,912,235 | A | 6/1999 | Hoeltje et al. |
| 5,952,320 | A | 9/1999 | Davidsen et al. |
| 5,969,132 | A | 10/1999 | Farr et al. |
| 5,972,939 | A | 10/1999 | Chen et al. |
| 6,043,357 | A | 3/2000 | Abbenante et al. |
| 6,080,838 | A | 6/2000 | Etzkorn et al. |
| 6,100,239 | A | 8/2000 | Ataka et al. |
| 6,100,377 | A | 8/2000 | Greene |
| 6,121,257 | A | 9/2000 | Kawai et al. |
| 6,124,453 | A | 9/2000 | Fehr et al. |
| 6,165,985 | A | 12/2000 | Jasserand et al. |
| 6,228,986 | B1 | 5/2001 | Lanter et al. |
| 6,255,285 | B1 | 7/2001 | Kotake et al. |
| 6,281,352 | B1 | 8/2001 | Xue et al. |
| 6,307,044 | B1 | 10/2001 | Dorow et al. |
| 6,329,376 | B1 | 12/2001 | Bergman |
| 6,348,447 | B1 | 2/2002 | Hellstrom et al. |
| 6,350,755 | B1 | 2/2002 | Desolms et al. |
| 6,358,985 | B1 | 3/2002 | Anthony et al. |
| 6,380,228 | B1 | 4/2002 | Stump et al. |
| 6,384,031 | B2 | 5/2002 | Chen et al. |
| 6,392,040 | B2 | 5/2002 | Chen et al. |
| 6,403,775 | B1 | 6/2002 | McDaniel |
| 6,410,534 | B1 | 6/2002 | Dinsmore et al. |
| 6,413,964 | B1 | 7/2002 | Desolms et al. |
| 6,423,714 | B2 | 7/2002 | Chen et al. |
| 6,441,017 | B1 | 8/2002 | Bell et al. |
| 6,511,980 | B2 | 1/2003 | Johnson et al. |
| 6,534,506 | B2 | 3/2003 | Nguyen et al. |
| 6,548,501 | B2 | 4/2003 | Hakkinen .................. 514/249 |
| 6,562,823 | B1 | 5/2003 | Dinsmore et al. |
| 6,562,963 | B2 | 5/2003 | Dorow et al. |
| 6,566,385 | B2 | 5/2003 | Desolms et al. |
| 6,586,630 | B1 | 7/2003 | Matsuoka et al. |
| 6,608,027 | B1 | 8/2003 | Tsantrizos et al. |
| 6,610,722 | B2 | 8/2003 | Stump et al. |
| 6,624,165 | B2 | 9/2003 | Chen et al. |
| 6,632,818 | B2 | 10/2003 | Dinsmore |
| 6,660,832 | B1 | 12/2003 | Jefferson et al. |
| 6,667,309 | B2 | 12/2003 | Chen et al. |
| 6,720,433 | B2 | 4/2004 | Matsuoka et al. |
| 2001/0041701 | A1 | 11/2001 | Chen |
| 2001/0056106 | A1 | 12/2001 | Chen et al. |
| 2002/0002192 | A1 | 1/2002 | Chen |
| 2002/0013352 | A1 | 1/2002 | Johnson et al. |
| 2002/0016294 | A1 | 2/2002 | Venkatraman |
| 2002/0049217 | A1 | 4/2002 | Desolms et al. |
| 2002/0058286 | A1 | 5/2002 | Danishefsky et al. |
| 2002/0058817 | A1 | 5/2002 | Danishefsky et al. |
| 2002/0091151 | A1 | 7/2002 | Danishefsky et al. |
| 2002/0103238 | A1 | 8/2002 | Chen |
| 2002/0111484 | A1 | 8/2002 | Chen |
| 2002/0192773 | A1 | 12/2002 | Walsh et al. |
| 2003/0158377 | A1 | 8/2003 | Walsh et al. |
| 2003/0176643 | A1 | 9/2003 | Matsuoka et al. |
| 2003/0181363 | A1 | 9/2003 | Llinas-Brunet |
| 2003/0191053 | A1 | 10/2003 | Matsuoka et al. |
| 2003/0203906 | A1 | 10/2003 | Johnson et al. |
| 2003/0211982 | A1 | 11/2003 | Saragovi et al. |
| 2003/0224977 | A1 | 12/2003 | Llinas-Bruunet et al. |
| 2003/0236199 | A1 | 12/2003 | Pulley et al. |
| 2003/0236240 | A1 | 12/2003 | Pulley et al. |
| 2004/0002448 | A1 | 1/2004 | Tsantrizos et al. |
| 2004/0038872 | A1 | 2/2004 | Campbell et al. |
| 2004/0063640 | A1 | 4/2004 | Burg et al. |
| 2005/0049234 | A1* | 3/2005 | Deslongchamps et al. .. 514/183 |
| 2005/0119169 | A1* | 6/2005 | Deslongchamps et al. .... 514/10 |
| 2005/0137127 | A1* | 6/2005 | Deslongchamps et al. ..... 514/8 |

FOREIGN PATENT DOCUMENTS

| | | |
|---|---|---|
| WO | WO-98/46631 | 10/1998 |
| WO | WO-98/51665 | 11/1998 |
| WO | WO-00/17231 | 3/2000 |
| WO | WO-00/44770 | 8/2000 |
| WO | WO-01/05811 | 1/2001 |
| WO | WO-01/14346 | 3/2001 |
| WO | WO-01/16162 | 3/2001 |
| WO | WO-01/25257 | 4/2001 |
| WO | WO-01/42228 | 6/2001 |
| WO | WO-01/53331 | 7/2001 |
| WO | WO-01/77113 | 10/2001 |
| WO | WO-01/81325 | 11/2001 |
| WO | WO-02/16369 | 2/2002 |
| WO | WO-02/40463 | 5/2002 |
| WO | WO-02/051413 | 7/2002 |
| WO | WO-02/064623 | 8/2002 |
| WO | WO-02/070547 | 9/2002 |
| WO | WO-02/092592 | 11/2002 |
| WO | WO-02/20510 | 3/2003 |
| WO | WO-03/024996 | 3/2003 |
| WO | WO-03/053349 | 7/2003 |
| WO | WO-03/054000 | 7/2003 |
| WO | WO-03/064455 | 7/2003 |
| WO | WO-03/068168 | 8/2003 |
| WO | WO-03/076424 | 9/2003 |
| WO | WO-02/102400 | 12/2003 |
| WO | WO-03/106480 | 12/2003 |
| WO | WO-2004/000742 | 12/2003 |
| WO | WO-2004/007483 | 1/2004 |
| WO | WO-2004/012816 | 2/2004 |
| WO | WO-2004/018503 | 3/2004 |
| WO | WO-2004/026881 | 4/2004 |

* cited by examiner

General Synthetic Strategy to Conformationally-Defined Macrocycles of the Present Invention Scheme 1

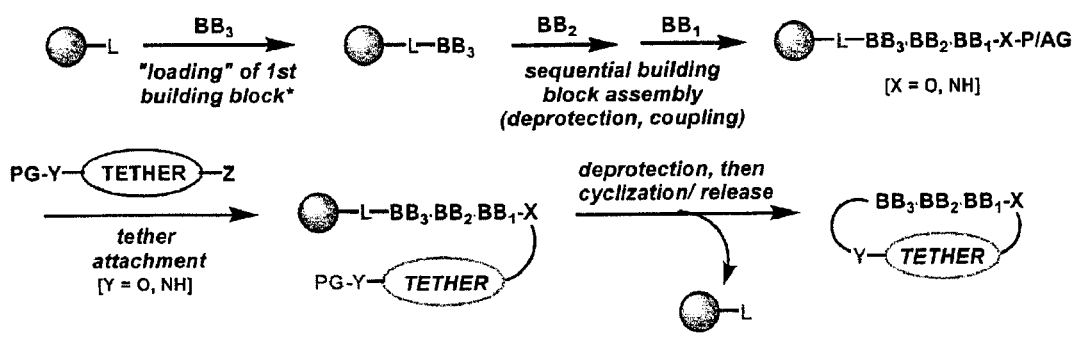

- ⬤—L = polymer with linker (L) for solid phase; appropriate protecting group for solution phase; for the latter, the scheme typically starts with the protected first building block
- $BB_i$ = building blocks (amino acids, hydroxy acids)
  *$BB_i$ numbered in order from C-terminus in analogy to standard peptide nomenclature, NOT in order of addition
- PG = protecting group
- P/AG = protecting and/or activating group
- Z = reactive group

FIG. 1

Standard Procedure for the Synthesis of Tether T8

Standard Procedure for the Synthesis of Tether T9

The yield of Ddz-T9 from T9-0 on a 65 g scale was 60.9 g (91%)

$^1$H NMR (CDCl$_3$): δ 7.19-7.01, (m, 2H), 6.92-9.83 (m, 2H), 6.53 (bs, 2H), 6.34 (t, 1H), 5.17 (bt, 1H), 4.08 (m, 2H), 3.98 (m, 2H), 3.79 (s, 6H), 3.01 (bq, 2H), 2.66 (t, 3H), 1.26 (bs, 8H);

$^{13}$C NMR (CDCl$_3$) δ 160.9, 156.8, 155.6, 149.6, 130.4, 127.5, 121.2, 111.7, 103.2, 98.4, 80., 69.7, 61.6, 55.5, 40.3, 30.5, 29.3, 27.4

Standard Procedure for the Synthesis of Ddz-propargylamine

Standard Procedure for the Synthesis of Tether T10

*Method A*

TLC (EtOAc/Hexanes 1:1, detection: UV, ninhydrin; $R_f$ = 0.17)

$^1$H NMR (CDCl$_3$) $\delta$ 7.18, t, 1H, J = 8.2Hz; 6.51, m, 5H; 6.34, t, 1H, J = 2.2Hz; 5.19, s, 1H; 4.05, t, 2H, J = 5.0Hz; 3.94, m, 4H; 3.75, s, 6H; 3.49, d, 2H J = 5.2Hz; 1.73, s, 6H.

$^{13}$C NMR (CDCl$_3$) $\delta$ 160.856; $\delta$ 160.152; 160.005; 155.410; 149.305; 130.279; 107.438; 107.310; 103.163; 101.877; 98.517; 69.488; 67.382; 61.595; 55.427; 40.420; 29.427.

HPLC (standard gradient) $t_R$: 7.25 min
MS: 420 (M+H)

*Method B*

The second synthetic route to T10 is presented in the accompanying scheme.

Standard Procedure for the Synthesis of Tether T11

TLC (15:85 THF/DCM; detection: UV; $R_f$: 0.33).

$^1$H NMR (DMSO-d$_6$) $\delta$ 8.00, d, 1H; 7.32, d, 1H; 7.15, m, 1H; 6.44, s, 2H; 6.33, s, 1H; 3.99, t, 2H; 3.71, m, 8H; 2.89, m = 4, 2H; 2.71, t, 2H; 1.71, m = 5, 2H; 1.61, s, 6H.

$^{13}$C NMR, solvent DMSO-d$_6$) $\delta$ 160.879; 153.275; 151.405; 150.447; 140.773; 122.666; 118.934; 103.347; 98.456; 79.778; 70.449; 60.212; 55.717; 55.599; 29.740; 28.592.

HPLC (standard gradient) $t_R$: 5.4 min

MS: 419 (M+H)

Standard Procedure for the Synthesis of Tether T12

Procedure for Synthesis of PPh3-DIAD Adduct

Standard Procedure for Attachment of Tethers via Reductive Amination

Standard Procedure for the Synthesis of Tether T28

Standard Procedure for the Synthesis of Tether T32

TLC (100% EtOAc; detection: UV, CMA; $R_f$ = 0.24).

$^1$H NMR (CDCl$_3$, ppm): 7.74 (1H, dd), 7.35 (1H, d), 6.72 (1H, d), 6.53-6.49 (2H, m), 3.61-3.29 (1H, m), 5.06 (1H, t), 4.25-4.01 (2H, m), 3.91-3.89 (2H, m), 3.73 (3H, s), 2.99 (2H, dd), 2.63 (2H, t), 1.71 (8H, broad), 1.53 (9H, s).

$^{13}$C NMR (CDCl$_3$, ppm): 163.8, 162.2, 161.0, 159.7, 155.9, 149.4, 130.0, 129.1, 128.0, 126.8, 110.8, 98.1, 80.9, 79.3, 69.7, 61.3, 55.5, 39.1, 29.3, 28.5, 26.7.

Standard Procedure for the Synthesis of Tether T33a and T33b $^1$H NMR (CDCl$_3$) δ (ppm) 7.18-7.11 (m, 2H), 6.90 (m, 2H), 6.52 (m, 2H), 6.33(m, 1H), 5.09 (bt, 1H), 4.52 (m, 1H), 3.77 (s, 6H), 3.08 (bq, 2H), 2.64 (bt, 2H), 1.75 (m, 8H); 1.27 (bd, 3H), $^{13}$C NMR (CDCl$_3$) δ 160.8, 155.5, 149.5, 131.2, 130.6, 127.4, 121.2, 113.3, 103.2, 98,4, 80.7, 74.8, 66.5, 55,4, 40.2, 30.6, 29.3, 29.2, 27.4, 16.1

Standard Procedure for the Synthesis of Tether T34

TLC (100% EtOAc; detection: CMA, $R_f$ = 0.5)

MW Calc. for $C_{24}H_{35}N_3O_7$, 477.55; MS Found $(M+H)^+$ 478.

$^1$H NMR (CDCl$_3$) δ 1.62 (m, 2H), 1.70 (m, 8H), 2.43 (m, 2H), 2.67 (m, 2H), 3.07 (m, 2H), 3.34 (s, 3H), 3.43 (s, 3H), 3.61 (m, 2H), 3.75 (s, 6H), 5.40 (sb, 1H), 6.31 (s, 1H), 6.49 (s, 2H)

$^{13}$C NMR (CDCl$_3$) δ 23.25 (CH$_2$), 25.97 (CH$_2$), 28.56 (CH$_3$), 39.31 (CH$_3$), 30.09 (CH$_3$), 31.25 (CH$_2$), 32.19 (CH$_2$), 40.16 (CH$_2$), 55.47 (CH$_3$), 61.38 (CH$_2$), 80.65 (Cq), 99.38 (Cq), 103.17 (Cq), 111.01(Cq), 149, 60 (Cq), 151.33 (Cq), 152.46 (Cq), 160.80 (Cq).

HPLC (standard gradient) $t_R$: 6.68 min.

Standard Procedure for the Synthesis of Tether T35

TLC (25/75 EtOAc/Hex; detection: UV, ninhydrin; $R_f$ = 0.03)

$^1$H NMR (CDCl$_3$): δ 7.06-7.00 (bt, 1H), 6.61-6.52 (m, 4H), 6.35 (m, 1H), 5.12 (bt, 1H), 4.03 (m, 2H), 3.95 (m, 2H), 3.77 (s, 6H), 3.11-3.04 (bq, 2H), 2.60 (bt, 2H), 1.75 (m, 8H)

$^{13}$C NMR (CDCl$_3$): δ 163.9, 160.9, 160.6, 157.6, 157.5, 155.6, 149.5, 130.8, 130.6, 125.9, 107.26, 106.9, 103.2, 98,4, 80.8, 77.5, 69.9, 61,3, 60.9, 60.6, 55,4, 40.3, 30.4, 29.3, 26.9,

HPLC (standard gradient): $t_R$ = 8.37 min

Standard Procedure for the Synthesis of Tether T36

TLC: (25/75 EtOAc/Hex; detection: UV, ninhydrin; $R_f$ = 0.03)

$^1$H NMR (CDCl$_3$) δ (ppm): 6.84-6.75 (m, 3H), 6.52 (bs, 2H), 6.34 (m, 1H), 5.17 (bt, 1H), 4.01 (m, 2H), 3.93 (m, 2H), 3.77 (s, 6H), 3.10 (bq, 2H), 2.63 (bt, 2H), 1.74 (m, 8H)

$^{13}$C NMR (CDCl$_3$) δ 160.9, 158.9, 155.8, 155.6, 152.9, 152.9, 149.5, 132.4, 132.3, 117.1, 116.8, 112.7, 112.6, 103.2, 98.4, 80.8, 70.4, 61.6, 55.5, 40.2, 30.3, 29.3, 27.4.

HPLC (standard gradient): $t_R$ = 8.29 min

Standard Procedure for the Synthesis of Tether T37

TLC (25/75 EtOAc/Hex; detection: UV, ninhydrin; $R_f$ = 0.03 )

$^1$H NMR (CDCl$_3$): δ 7.12-7.08 (bd, 2H), 6.76-6.73 (d, 1H), 6.52 (m, 2H), 6.33 (bs, 1H), 5.15 (bt, 1H), 4.02 (m, 2H), 3.95 (m, 2H), 3.79 (s, 6H), 3.09 (bq, 2H), 2.61 (bt, 2H), 1.74 (m, 8H). $^{13}$C NMR (CDCl$_3$) δ 160.8, 155.6, 155.4, 149.5, 132.4, 130.1, 127.0, 126.0, 112.8, 103.2, 98.4, 80.8, 70.0, 61.4, 55.5, 40.3, 30.2, 29.3, 24.5, 27.4

HPLC (standard gradient): $t_R$ = 9.60 min

Standard Procedure for the Synthesis of Tether T38

¹H NMR (CDCl₃): δ 7.20-7.10, (m, 2H), 6.95-6.80 (m, 2H), 6.55 (bs, 2H), 6.35 (s, 1H), 5.18 (bt, 1H), 4.12 (m, 1H), 3.95 (m, 2H), 3.80 (s, 6H), 3.15 (bq, 2H), 2.65 (t, 2H), 1.98 (bs, 2H), 1.65 (bs, 6H), 1.25 (m, 3H).

¹³C NMR (CDCl₃): δ 160.8, 156.6, 155.8, 149.6, 130.4, 127.5, 121.3, 111.7, 103.2, 98.4, 80.7, 73.5, 66.6, 55.5, 40.2, 30.5, 29.3, 29.1, 27.3, 19.5.

Standard Procedure for the Synthesis of Tether T39

TLC (50% EtOAc, 50% Hex; detection: UV and CMA; $R_f$ = 0.25)

$^1$H NMR (CDCl$_3$, ppm): 7.11-7.08 (2H, m), 6.86 (1H, t), 6.76 (1H, d), 5.05 (1H, broad), 4.26-3.85 (4H, m), 3.22-3.07 (2H, m), 2.71 (1H, broad), 1.66-1.60 (2H, m), 1.33 (9H, s), 1.17 (3H, d).

$^{13}$C NMR (CDCl$_3$, ppm): 156.1, 135.0, 127.1, 127.0, 121.4, 111.7, 69.9, 61.5, 39.8, 38.4, 28.7, 20.7.

Standard Procedure for the Synthesis of Tether T40

TLC (50% EtOAc, 50% Hex; detection: UV and CMA; $R_f$ = 0.25)

$^1$H NMR (CDCl$_3$, ppm): 7.11-7.08 (2H, m), 6.86 (1H, t), 6.76 (1H, d), 5.05 (1H, broad), 4.26-3.85 (4H, m), 3.22-3.07 (2H, m), 2.71 (1H, broad), 1.66-1.60 (2H, m), 1.33 (9H, s), 1.17 (3H, d).

$^{13}$C NMR (CDCl$_3$, ppm): 156.1, 135.0, 127.1, 127.0, 121.4, 111.7, 69.9, 61.5, 39.8, 38.4, 28.7, 20.7.

Standard Procedure for the Synthesis of Tether T41

TLC (100% EtOAc; detection: CMA; $R_f$ = 0.5)

$^1$H NMR (CDCl$_3$) δ 1.23 (s, 3H), 1.49 (s, 3H), 1.69 (s, 3H), 1.74 (s, 3H), 1.90 (m, 2H), 2.35 (m, 1H), 3.35 (m, 2H), 3.76 (s, 6H), 3.92 (m, 2H), 4.40 (m, 2H), 5.10 (m, 1H), 6.15 (s, 1H), 6.25 (s, 2H).

$^{13}$C NMR (CDCl$_3$) δ 25.52 (CH$_3$), 27.53 (CH$_3$), 28.88 (CH$_3$), 29.61 (CH$_3$), 35.92 (CH$_2$), 42.62 (CH$_2$), 55.43 (CH$_3$), 60.60 (CH$_2$), 82.38 (CH), 83.33 (CH), 83.68 (CH), 84.96 (CH), 98.26 (CH), 103.23 (CH), 118.3 (Cq), 149.50 (Cq), 156.20 (Cq), 160, 02 (Cq)

HPLC (standard gradient): $t_R$ = 6.64 min

MS: M+H found: 439

Standard Procedure for the Synthesis of Tether T42

$^1$H NMR (300 MHz, CDCl$_3$) δ 6.82-6.98 (m, 2H); 6.80-6.75 (m, 1H); 6.53 (s, 2H); 6.35 (t, 1H, 2 Hz); 5.23 (b, 1H); 4.08 (m, 1H); 3.90-3.68 (m, 8H); 3.20-2.97 (m, 2H); 2.95-53 (m, 4H); 2.0-1.63 (m, 10H).

$^{13}$C NMR (75.5 MHz, CDCl$_3$) δ 160.85; 155.56; 152.55; 149.56; 128.13; 127.77; 120.28; 103.22; 98.43; 80.72; 76.80; 65.76; 55.46; 40.23; 30.45; 29.34; 29.22; 27.10; 24.97; 23.94.

Scheme 2: Thioester Strategy for Macrocyclic Compounds of the Present Invention

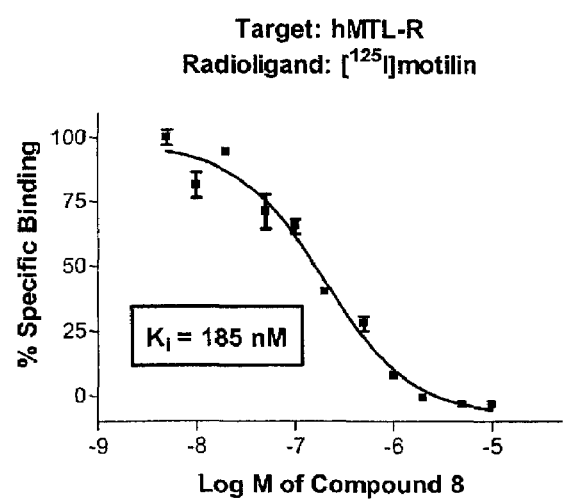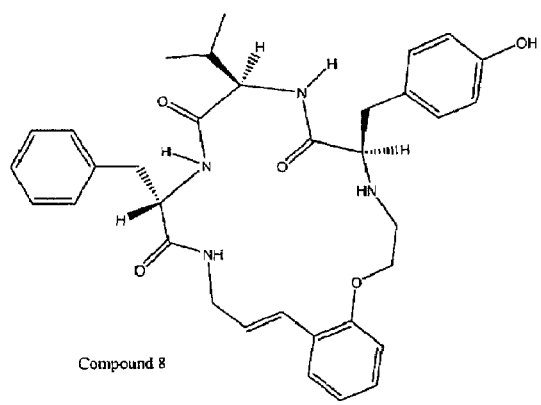
Compound 8
FIG. 23

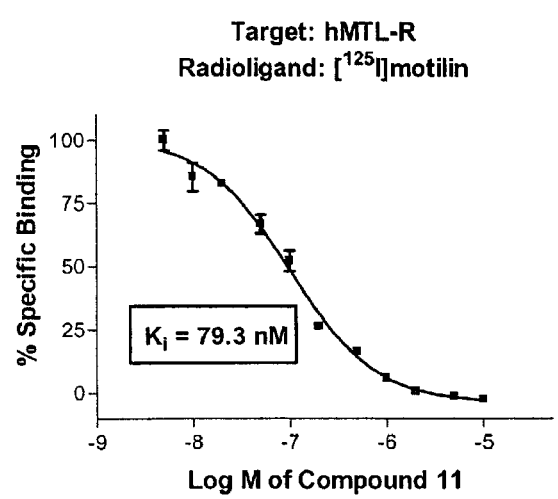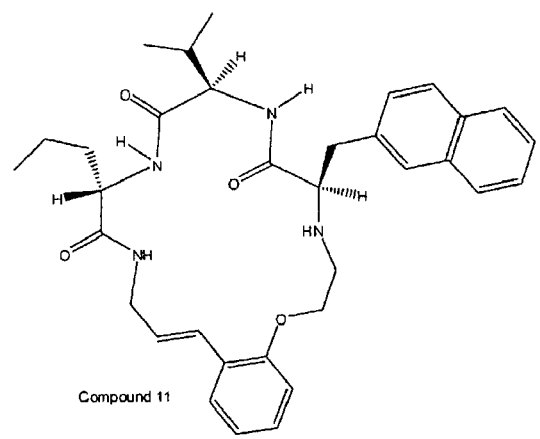
FIG. 24

MACROCYCLIC ANTAGONISTS OF THE MOTILIN RECEPTOR

FIELD OF THE INVENTION

The present invention relates to novel conformationally-defined macrocyclic compounds, pharmaceutical compositions comprising same and intermediates used in their manufacture. More particularly, the invention relates to macrocyclic compounds that have been demonstrated to selectively antagonize the activity of the motilin receptor. The invention further relates to macrocyclic compounds useful as therapeutics for a range of gastrointestinal disorders, in particular those in which malfunction of gastric motility or increased motilin secretion is observed, such as hypermotilinemia, irritable bowel syndrome and dyspepsia.

BACKGROUND OF THE INVENTION

A number of peptide hormones are involved in the control of the different functions in the gastrointestinal (GI) tract, including absorption, secretion, blood flow and motility (Mulvihill, et al. in *Basic and Clinical Endocrinology*, 4$^{th}$ edition, Greenspan, F. S.; Baxter, J. D., eds., Appleton & Lange: Norwalk, Conn., 1994, pp 551-570). Since interactions between the brain and GI system are critical to the proper modulation of these functions, these peptides can be produced locally in the GI tract or distally in the CNS.

One of these peptide hormones, motilin, a linear 22-amino acid peptide, plays a critical regulatory role in the GI physiological system though governing of fasting gastrointestinal motor activity. As such, the peptide is periodically released from the duodenal mucosa during fasting in mammals, including humans. More precisely, motilin exerts a powerful effect on gastric motility through the contraction of gastrointestinal smooth muscle to stimulate gastric emptying, decrease intestinal transit time and initiate phase III of the migrating motor complex in the small bowel (Itoh, Z., Ed., *Motilin*, Academic Press: San Diego, Calif., 1990, ASIN: 0123757304; Nelson, D. K. *Dig. Dis. Sci.* 1996, 41, 2006-2015; Peeters, T. L.; Vantrappen, G.; Janssens, J. *Gastroenterology* 1980, 79, 716-719).

Motilin exerts these effects through receptors located predominantly on the human antrum and proximal duodenum, although its receptors are found in other regions of the GI tract as well (Peeters, T. L.; Bormans, V.; Vantrappen, G. *Regul. Pept.* 1988, 23, 171-182). Therefore, motilin hormone is involved in motility of both the upper and lower parts of the GI system (Williams et al. *Am. J. Physiol.* 1992, 262, G50-G55). In addition, motilin and its receptors have been found in the CNS and periphery, suggesting a physiological role in the nervous system that has not yet been definitively elucidated (Depoortere, I.; Peeters, T. L. *Am. J. Physiol.* 1997, 272, G994-999 and O'Donohue, T. L et al. *Peptides* 1981, 2, 467-477). For example, motilin receptors in the brain have been suggested to play a regulatory role in a number of CNS functions, including feeding and drinking behavior, micturition reflex, central and brain stem neuronal modulation and pituitary hormone secretion (Itoh, Z. Motilin and Clinical Applications. *Peptides* 1997, 18, 593-608; Asakawa, A.; Inui, A.; Momose, K.; et al., M. *Peptides* 1998, 19, 987-990 and Rosenfeld, D. J.; Garthwaite, T. L. *Physiol. Behav.* 1987, 39, 753-756). Physiological studies have provided confirmatory evidence that motilin can indeed have an effect on feeding behavior (Rosenfeld, D. J.; Garthwaite, T. L. *Phys. Behav.* 1987, 39, 735-736).

The recent identification and cloning of the human motilin receptor (WO 99/64436) has simplified and accelerated the search for agents which can modulate its activity for specific therapeutic purposes.

Due to the critical and direct involvement of motilin in control of gastric motility, agents that either diminish (hypomotility) or enhance (hypermotility) the activity at the motilin receptor, are a particularly attractive area for further investigation in the search for new effective pharmaceuticals towards these indications.

Peptidic agonists of the motilin receptor, which have clinical application for the treatment of hypomotility disorders, have been reported (U.S. Pat. Nos. 5,695,952; 5,721,353; 6,018,037; 6,380,158; 6,420,521, U.S. Appl. 2001/0041791, WO 98/42840; WO 01/00830 and WO 02/059141). Derivatives of erythromycin, commonly referred to as motilides, have also been reported as agonists of the motilin receptor (U.S. Pat. Nos. 4,920,102; 5,008,249; 5,175,150; 5,418,224; 5,470,961; 5,523,401, 5,554,605; 5,658,888; 5,854,407; 5,912,235; 6,100,239; 6,165,985; 6,403,775).

Antagonists of the motilin receptor are potentially extremely useful as therapeutic treatments for diseases associated with hypermotility and hypermotilinemia, including irritable bowel syndrome, dyspepsia, gastroesophogeal reflux disorders, Crohn's disease, ulcerative colitis, pancreatitis, infantile hypertrophic pyloric stenosis, diabetes mellitus, obesity, malabsorption syndrome, carcinoid syndrome, diarrhea, atrophic colitis or gastritis, gastrointestinal dumping syndrome, postgastroenterectomy syndrome, gastric stasis and eating disorders leading to obesity.

A variety of peptidic compounds have been described as antagonists of the motilin receptor (Depoortere, I.; Macielag, M. J.; Galdes, A.; Peeters, T. L. *Eur J. Pharmacol.* 1995, 286, 241-247; U.S. Pat. Nos. 5,470,830; 6,255,285; 6,586,630; 6,720,433; U.S. 2003/0176643; WO 02/64623). These peptidic antagonists suffer from the known limitations of peptides as drug molecules, in particular poor oral bioavailability and degradative metabolism.

Cyclization of peptidic derivatives is a method employed to improve the properties of a linear peptide both with respect to metabolic stability and conformational freedom. Cyclic molecules tend to be more resistant to metabolic enzymes. Such cyclic tetrapeptide motilin antagonists have been reported (Haramura, M. et al *J. Med. Chem.* 2002, 45, 670-675, U.S. 2003/0191053; WO 02/16404).

Other motilin antagonists, which are non-peptidic and non-cyclic in nature have also been reported (U.S. Pat. Nos. 5,972,939; 6,384,031; 6,392,040; 6,423,714; 6,511,980; 6,624,165; 6,667,309; U.S. 2002/0111484; 2001/041701; 2002/0103238; 2001/0056106, 2002/0013352; 2003/0203906 and 2002/0002192)

The macrocyclic motilin antagonists of the present invention comprise elements of both peptidic and non-peptidic structures in a combination which has not been pursued for this application previously.

Indeed, the structural features of antagonists of the present invention are different. In particular, within the known motilin antagonists which are cyclic peptides, it was found that such derivatives containing D-amino acids were devoid of activity. In contrast, for the tripeptidomimetic compounds of the present invention, the D-stereochemistry is required for two of the three building elements.

The motilin antagonists of the present invention are also distinct from the prior art in that they comprise a tether element to fulfill the dual role of controlling conformations and

SUMMARY OF THE INVENTION

In a first aspect, the present invention is directed to compounds of formula (I):

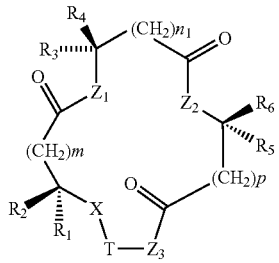

(I)

and pharmaceutically acceptable salts, hydrates or solvates thereof wherein:

$Z_1$, $Z_2$ and $Z_3$ are independently selected from the group consisting of O, N and $NR_{10}$, wherein $R_{10}$ is selected from the group consisting of hydrogen, lower alkyl, and substituted lower alkyl;

$R_1$ is independently selected from the group consisting of lower alkyl substituted with aryl, lower alkyl substituted with substituted aryl, lower alkyl substituted with heteroaryl and lower alkyl substituted with substituted heteroaryl;

$R_2$ is hydrogen;

$R_3$ is independently selected from the group consisting of alkyl and cycloalkyl with the proviso that when $Z_1$ is N, $R_3$ can form a four, five, six or seven-membered heterocyclic ring together with $Z_1$;

$R_4$ is hydrogen;

$R_5$ and $R_6$ are independently selected from the group consisting of hydrogen, alkyl, substituted alkyl, cycloalkyl, substituted cycloalkyl, heterocyclic, substituted heterocyclic, aryl, substituted aryl, heteroaryl and substituted heteroaryl, with the proviso that at least one of $R_5$ and $R_6$ is hydrogen;

X is selected from the group consisting of O, $NR_8$, and $N(R_9)_2^+$;
  wherein $R_8$ is selected from the group consisting of hydrogen, lower alkyl, substituted lower alkyl, formyl, acyl, carboxyalkyl, carboxyaryl, amido, sulfonyl, sulfonamido and amidino; and
  $R_9$ is selected from the group consisting of hydrogen, lower alkyl, and substituted lower alkyl;

m, $n_1$ and p are independently selected from 0, 1 or 2; and

T is a bivalent radical of formula II:

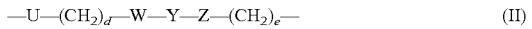

(II)

wherein d and e are independently selected from 0, 1, 2, 3, 4 or 5;
  wherein U is bonded to X of formula (I) and is —$CH_2$— or —C(=O)—;
  wherein Y and Z are each optionally present;
  W, Y and Z are independently selected from the group consisting of: —O—, —$NR_{28}$—, —S—, —SO—, —$SO_2$—, —C(=O)—, —C(=O)—O—, —O—C(=O)—, —(=ONH—, —NH—C(=O)—, —$SO_2$—NH—, —NH—$SO_2$—, —$CR_{29}R_{30}$—, —CH=CH— with a configuration Z or E, and —C≡C—, or from a ring structure independently selected from the group

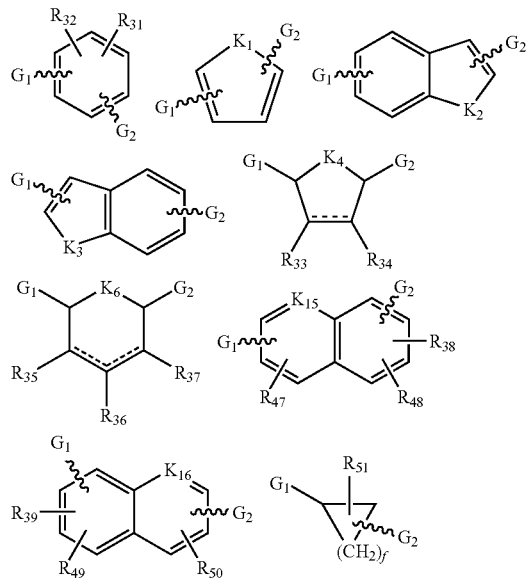

wherein any carbon atom contained within said ring structure, can be replaced by a nitrogen atom, with the proviso that if said ring structure is a monocyclic ring structure, it does not comprise more than four nitrogen atoms and if said ring structure is a bicyclic ring structure, it does not comprise more than six nitrogen atoms;

$G_1$ and $G_2$ each independently represent a covalent bond or a bivalent radical selected from the group consisting of —O—, —$NR_{41}$—, —S—, —SO—, —$SO_2$—, —C(=O)—, —C(=O)—O—, —O—C(=O)—, —C(=O)NH—, —NH—C(=O)—, —$SO_2$—NH—, —NH—$SO_2$—, —$CR_{42}R_{43}$—, —CH=CH— with a configuration Z or E, and —C≡C—; with the proviso that $G_1$ is bonded closer to U than $G_2$;

$K_1$, $K_2$, $K_3$, $K_4$, $K_6$, $K_{15}$ and $K_{16}$ are independently selected from the group consisting of O, $NR_{44}$ and S;

f is selected from 1, 2, 3, 4, 5 or 6;

$R_{31}$, $R_{32}$, $R_{38}$, $R_{39}$, $R_{48}$ and $R_{49}$ are independently selected from hydrogen, halogen, alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, amino, halogen, formyl, acyl, carboxy, carboxyalkyl, carboxyaryl, amido, carbamoyl, guanidino, ureido, amidino, cyano, nitro, mercapto, sulfinyl, sulfonyl and sulfonamido; and $R_{33}$, $R_{34}$, $R_{35}$, $R_{36}$, $R_{37}$, $R_{47}$, $R_{50}$ and $R_{51}$ are independently selected from hydrogen, halogen, alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, cyano, nitro, mercapto, sulfinyl, sulfonyl and sulfonamido.

In a second aspect, the invention also proposes compounds of formula (I) which are antagonists of the motilin receptor.

In a third aspect, the invention proposes a method of treating a disorder associated with the motilin receptor or motility dysfunction in humans and other mammals, comprising administering a therapeutically effective amount of a compound of formula (1).

While the invention will be described in conjunction with example embodiments, it will be understood that it is not intended to limit the scope of the invention to such embodiment. On the contrary, it is intended to cover all alternatives, modifications and equivalents as may be included as defined by the appended claims.

DETAILED DESCRIPTION OF THE INVENTION

Preferably in formula (I), as depicted hereinabove, $R_1$ is selected from the group consisting of —$(CH_2)_qR_{11}$, and —$CHR_{12}R_{13}$ wherein q is 0, 1, 2 or 3; and $R_{11}$ and $R_{12}$ are independently selected from a ring structure from the following group:

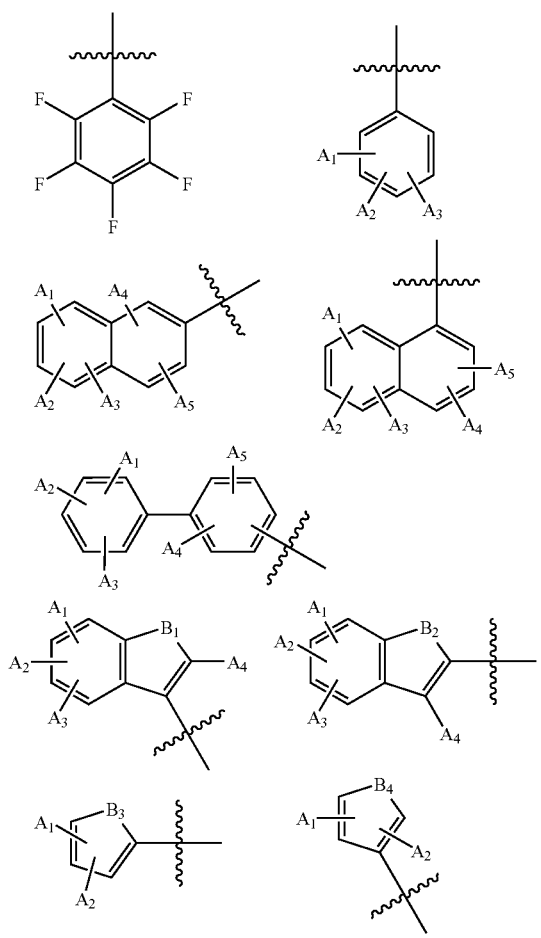

wherein any carbon atom in said ring structure can be replaced a nitrogen atom, with the proviso that if said ring structure is a monocyclic ring structure, it does not comprise more than four nitrogen atoms and if said ring structure is a bicyclic ring structure, it does not comprise more than six nitrogen atoms;

$A_1$, $A_2$, $A_3$, $A_4$ and $A_5$ are each optionally present and are independently selected from the group consisting of halogen, alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, amino, halogen, formyl, acyl, carboxy, carboxyalkyl, carboxyaryl, amido, carbamoyl, guanidino, ureido, amidino, cyano, nitro, mercapto, sulfinyl, sulfonyl and sulfonamido;

$B_1$, $B_2$, $B_3$, and $B_4$ are independently selected from $NR_{14}$, S or O, wherein $R_{14}$ is selected from the group consisting of hydrogen, alkyl, substituted alkyl, formyl, acyl, carboxyalkyl, carboxyaryl, amido, sulfonyl and sulfonamido;

$R_{13}$ is as defined for as $R_{11}$ and $R_{12}$ or is selected from the group comprising lower alkyl, substituted lower alkyl, hydroxy, alkoxy, aryloxy, amino, carboxy, carboxyalkyl, carboxyaryl, and amido.

wherein $A_1$, $A_2$, $A_3$, $A_4$ and $A_5$ are most preferably selected from halogen, trifluororomethyl, $C_{1-6}$ alkyl or $C_{1-6}$ alkoxy.

Preferably, $R_{11}$, $R_{12}$ and $R_{13}$ are selected from the group consisting of:

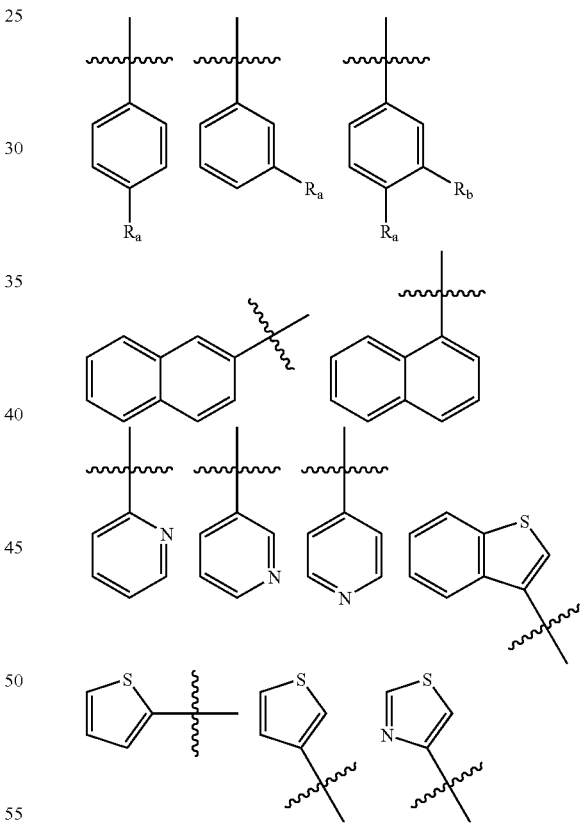

wherein $R_a$ and $R_b$ are chosen from the group consisting of Cl, F, $CF_3$, $OCH_3$, OH, and $C(CH_3)_3$ and $CH_3$.

Also preferably, $R_3$ in formula (I), is selected from the group consisting of:

—$(CH_2)_sCH_3$, —$CH(CH_3)(CH_2)_tCH_3$, —$CH(OR_{15})CH_3$, —$CH_2SCH_3$ —$CH_2CH_2SCH_3$, —$CH_2S(=O)CH_3$, —$CH_2CH_2S(=O)CH_3$, —$CH_2S(=O)_2CH_3$, —$CH_2CH_2S(=O)_2CH_3$, —$(CH_2)_uCH(CH_3)_2$, —$C(CH_3)_3$, and —$(CH_2)_y$—$R_{21}$, wherein:

s and u are independently selected from 0, 1, 2, 3, 4 or 5;

t is independently selected from 1, 2, 3 or 4;
y is selected from 0, 1, 2, 3 or 4;
$R_{15}$ is selected from the group consisting of hydrogen, alkyl, substituted alkyl, formyl and acyl;
$R_{21}$ is selected from a ring structure selected from the following group:

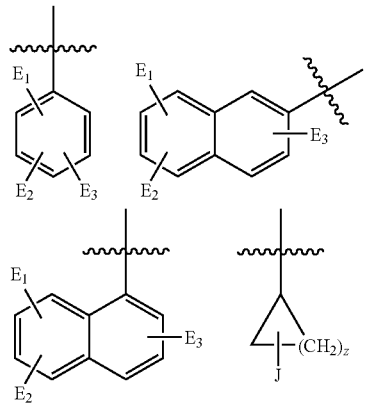

wherein any carbon atom in said ring structure can be replaced by a nitrogen atom, with the proviso that if said ring structure is a monocyclic ring structure, it does not comprise more than four nitrogen atoms and if said ring structure is a bicyclic ring structure, it does not comprise more than six nitrogen atoms;

z is selected from 1, 2, 3, 4 or 5;

$E_1$, $E_2$ and $E_3$ are each optionally present and are independently selected from the group consisting of halogen, alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, amino, halogen, formyl, acyl, carboxy, carboxyalkyl, carboxyaryl, amido, carbamoyl, guanidino, ureido, amidino, cyano, nitro, mercapto, sulfinyl, sulfonyl and sulfonamido; and J is optionally present and is selected from the group consisting of alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido.

The tether portion (T) of formula (I) is preferably selected from the group consisting of:

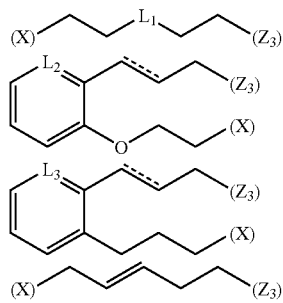

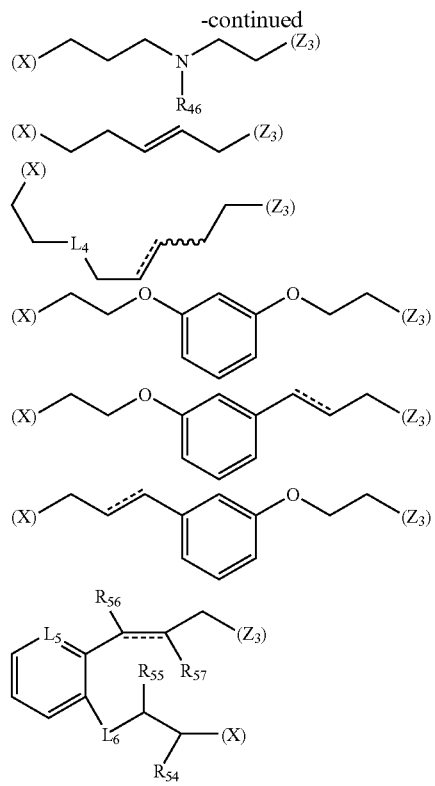

wherein $L_1$ is O, NH or NMe; $L_2$ is CH or N; $L_3$ is CH or N; $L_4$ is O or $CH_2$; $L_5$ is CH or N $L_6$ is $CR_{52}R_{53}$ or O; $R_{46}$ is H or $CH_3$;

$R_{52}$, $R_{53}$, $R_{54}$, $R_{55}$, $R_{56}$ and $R_{57}$ are independently selected from hydrogen, lower alkyl, substituted lower alkyl, hydroxy, alkoxy, aryloxy, amino, and oxo; or $R_{52}$ together with $R_{53}$ or $R_{54}$ together with $R_{55}$ or $R_{56}$ together with $R_{57}$ can independently form a three to seven-membered cyclic ring comprising carbon, oxygen, sulfur and/or nitrogen atoms;

(X) is the site of a covalent bond to X in formula (I); and ($Z_3$) is the site of a covalent bond to $Z_3$ in formula (I).

In a particularly preferred embodiment of the invention, there are provided compounds of formula (I) wherein m, n and p are 0, X, $Z_1$, $Z_2$ and $Z_3$ are NH and $R_2$, $R_4$ and $R_5$ are hydrogen, represented by formula (III):

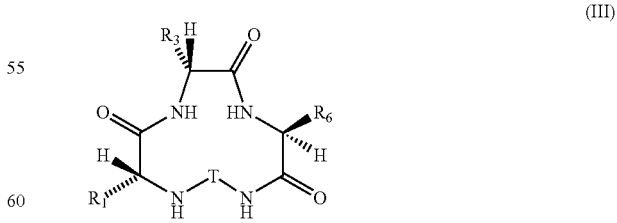

According to another aspect of the invention, there are provided compounds of formula (I) wherein when $Z_1$ is a nitrogen atom, $R_3$ forms a four, five, six or seven-membered heterocyclic ring together with $Z_1$, represented by formula (IV):

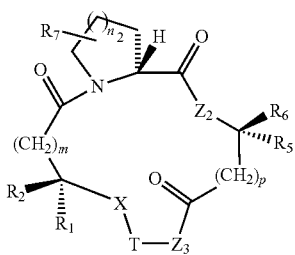

(IV)

wherein said heterocyclic ring may contain a second nitrogen atom, or an oxygen, or sulfur atom $n_2$ is selected from 0, 1, 2 or 3

$R_7$ is optionally present and is selected from the group consisting of alkyl, substituted alkyl, cycloalkyl, substituted cycloalkyl, heterocyclic, substituted heterocyclic, aryl, substituted aryl, heteroaryl, substituted heteroaryl, hydroxy, alkoxy, aryloxy, oxo, amino, halogen, formyl, acyl, carboxy, carboxyalkyl, carboxyaryl, amido, carbamoyl, guanidino, ureido, amidino, mercapto, sulfinyl, sulfonyl and sulfonamido.

It is to be understood, that in the context of the present invention, the terms amino, guanidine, ureido and amidino encompass substituted derivatives thereof as well.

Preferably, the invention provides a method of treating a disorder associated with hypermotility or hypermotilinemia in humans and other mammals comprising administering a therapeutically effective amount of a compound of formula (1).

BRIEF DESCRIPTION OF THE DRAWINGS

FIG. 1 depicts Scheme 1 presenting a general synthetic strategy to conformiationally-defined macrocycles of the present invention.

HPLC (standard gradient) $t_R$=8.46 min

Chiral material can be accessed by starting with the chiral epoxide. For example, the (S)-isomer of T38 was constructed in 89% overall yield from (S)-propylene oxide.

Figure 18:
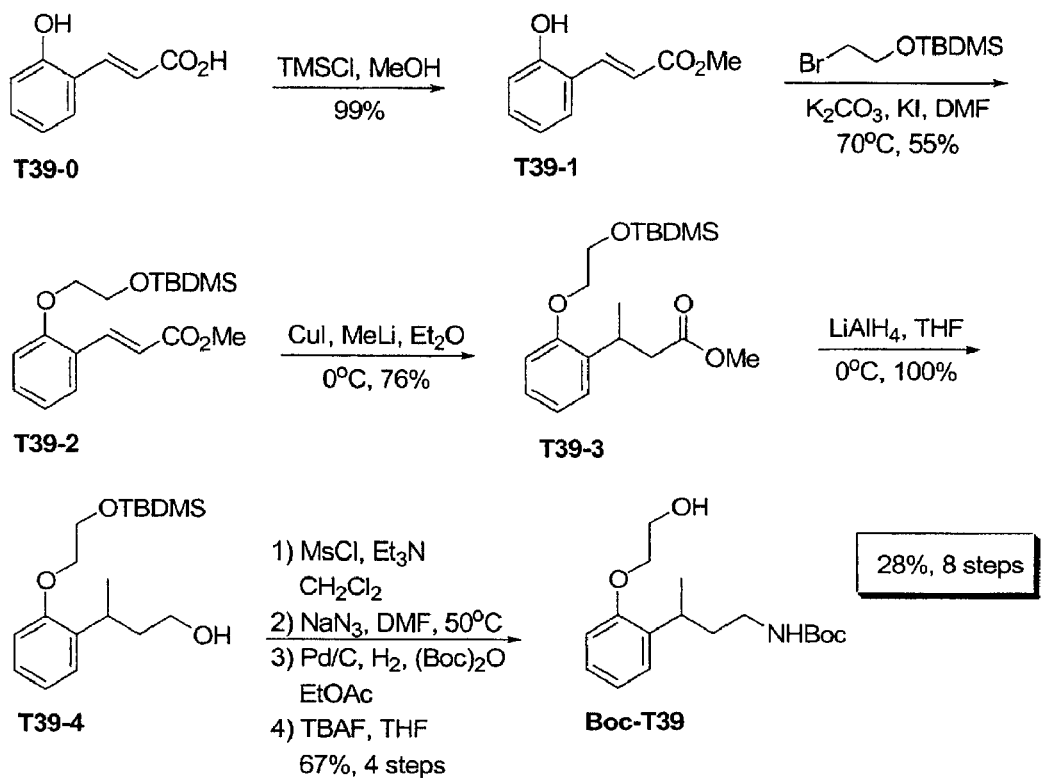

FIG. 18 depicts the standard procedure for the synthesis of tether T39. Chiral T39 can be accessed through the use of asymmetric synthesis methods, resolution or chiral chromatography techniques available in the literature.

Figure 19:
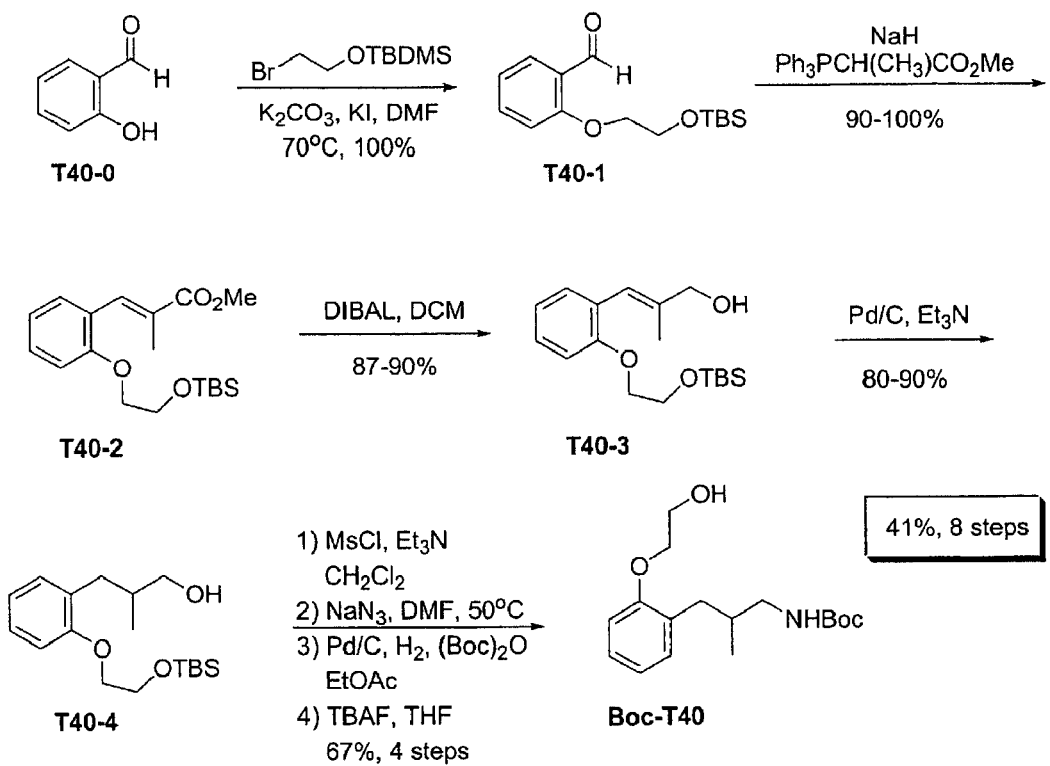

FIG. 19 depicts the standard procedure for the synthesis of tether T40. Chiral T40 can be accessed through the use of asymmetric synthesis methods, resolution or chiral chromatography techniques available in the literature.

Figure 20:
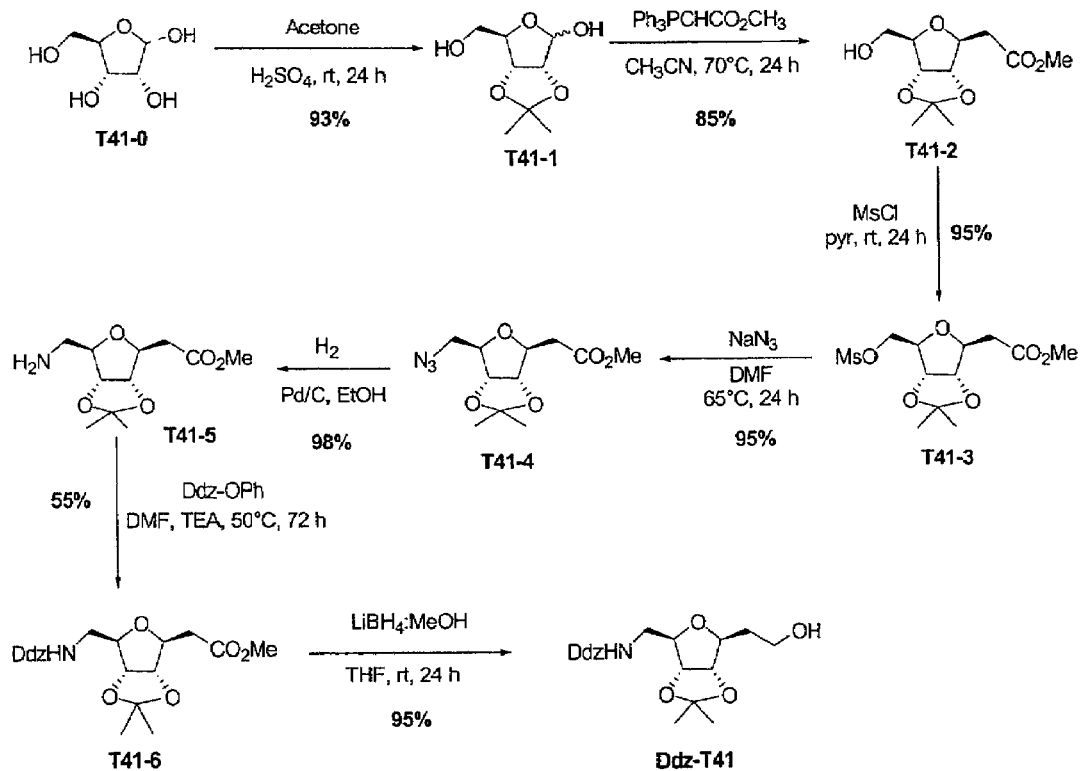

FIG. 20 depicts the standard procedure for the synthesis of tether T41.

Figure 21:
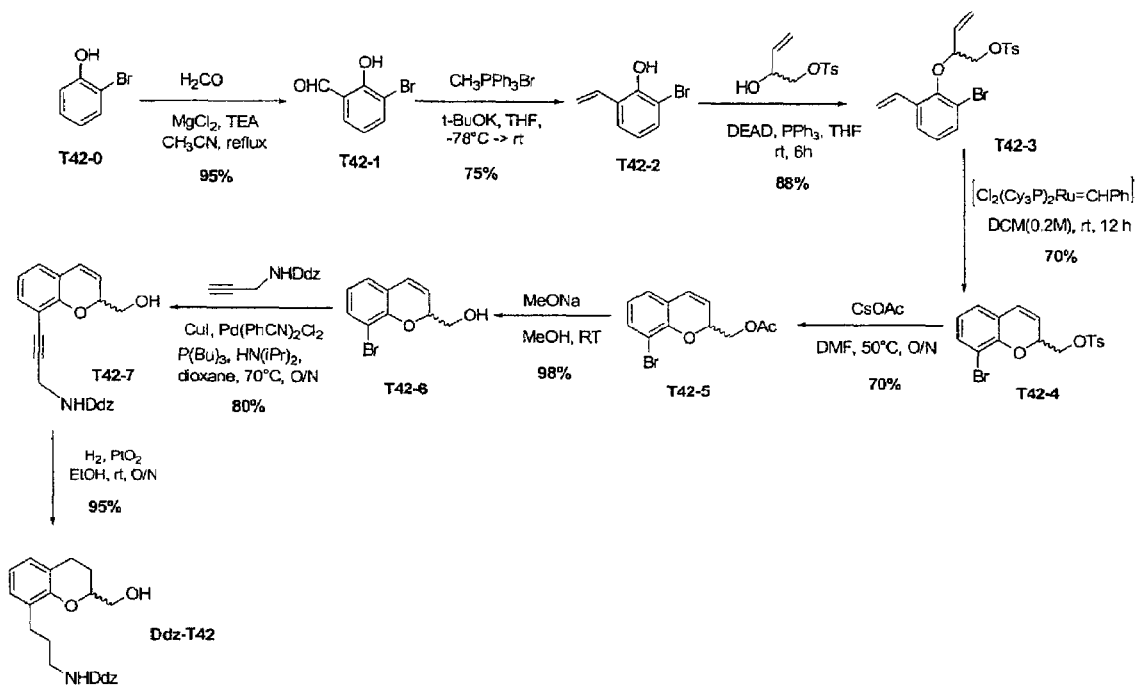

FIG. 21 depicts the standard procedure for the synthesis of tether T42.

Figure 22:
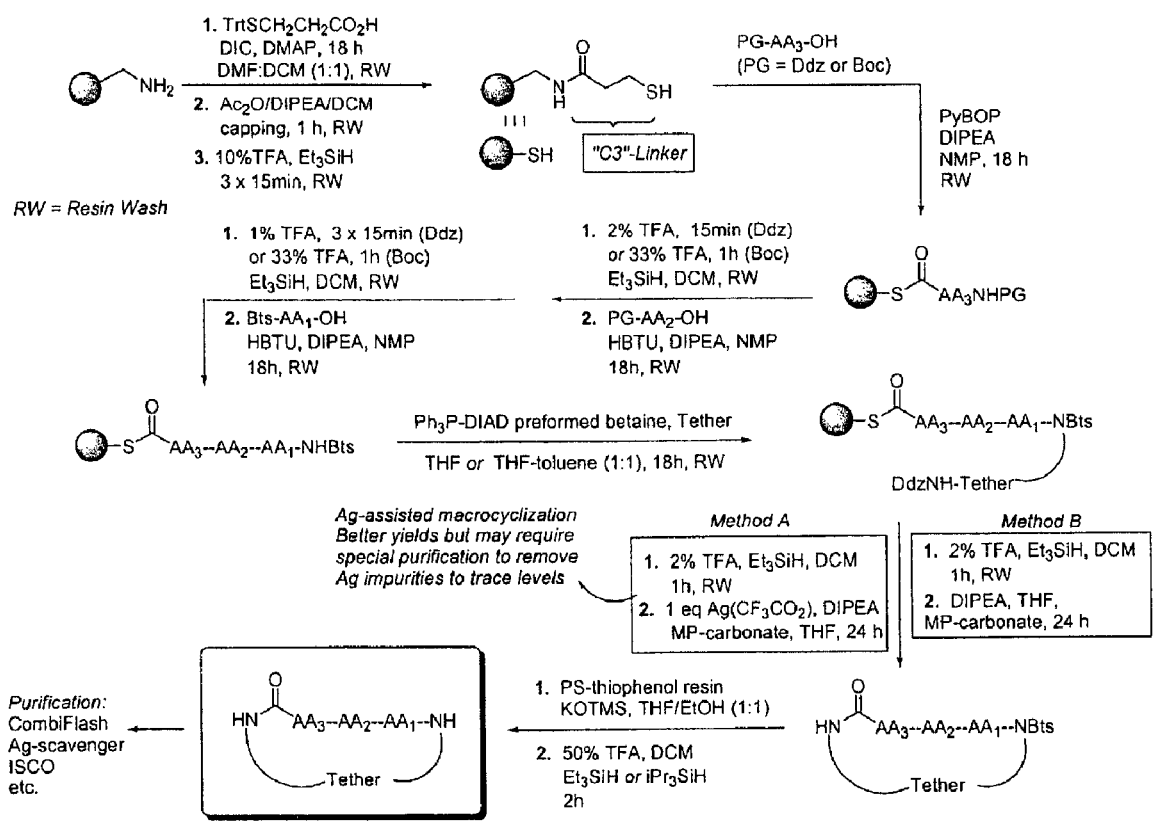

FIG. 22 depicts Scheme 2 of the thioester strategy for macrocyclic compounds of the present invention.

FIG. 23 depicts a competitive binding curve for a representative compound of the present invention (Compound 8).

FIG. 24 depicts a competitive binding curve for a representative compound of the present invention (Compound 11).

DESCRIPTION OF PREFERRED EMBODIMENTS

Although preferred embodiments of the present invention have been described in detail herein and illustrated in the accompanying structures, schemes and tables, it is to be understood that the invention is not limited to these precise embodiments and that various changes and modifications may be effected therein without departing from the scope or spirit of the present invention.

Specifically preferred compounds of the present invention, include, but are not limited to:

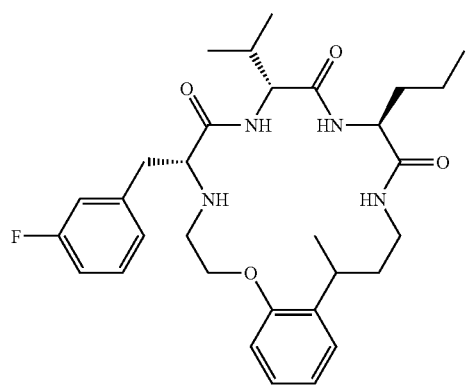

220

11
14
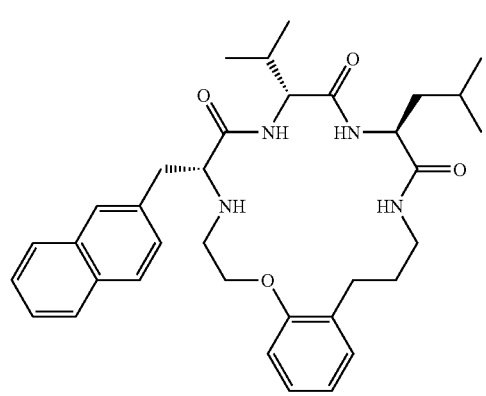
24
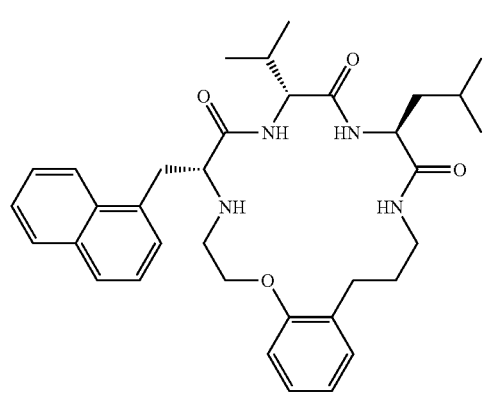
195
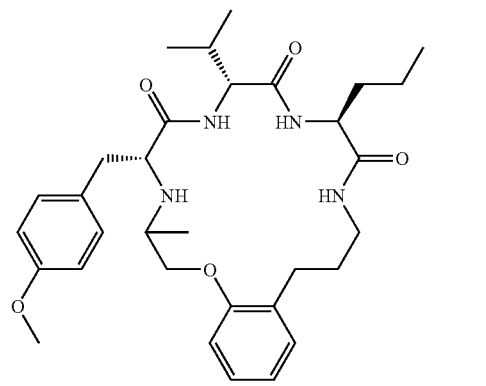
212
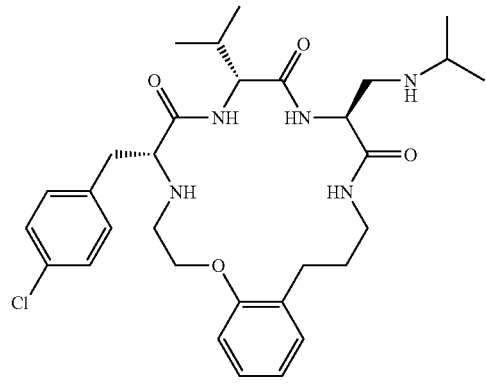
12
202
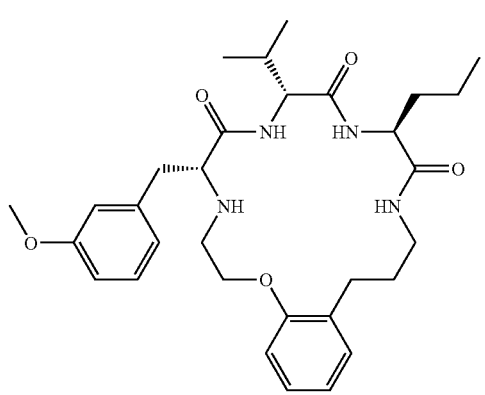
164
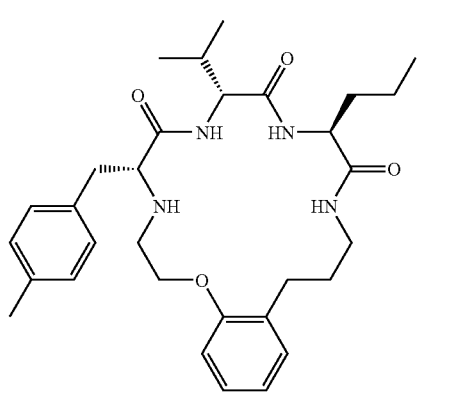
4
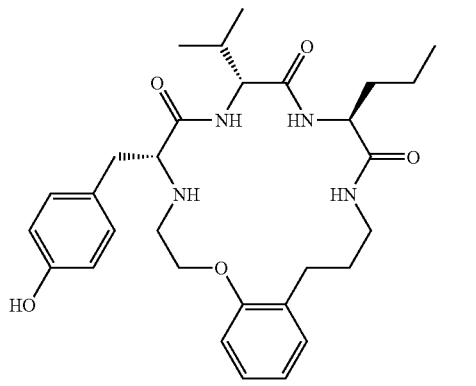
156
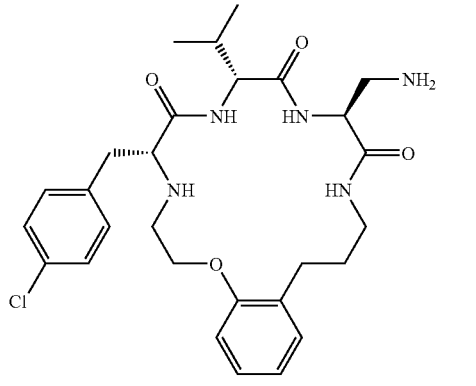

155
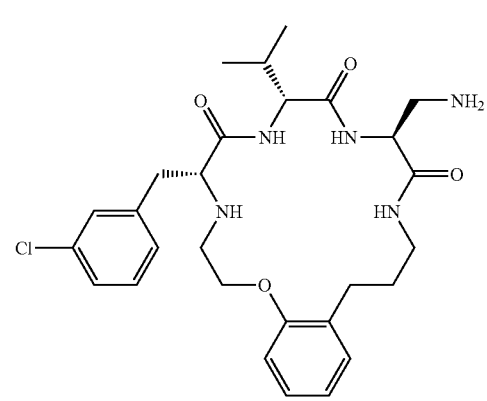
26
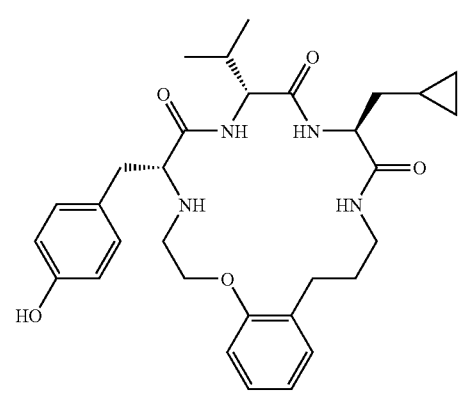
10
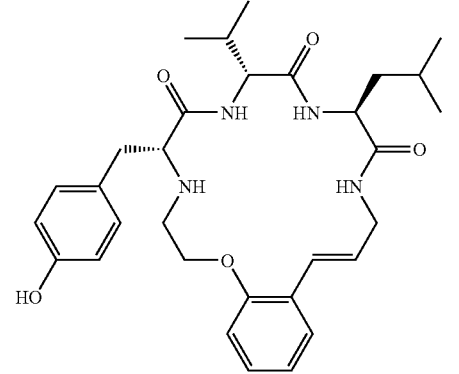
11
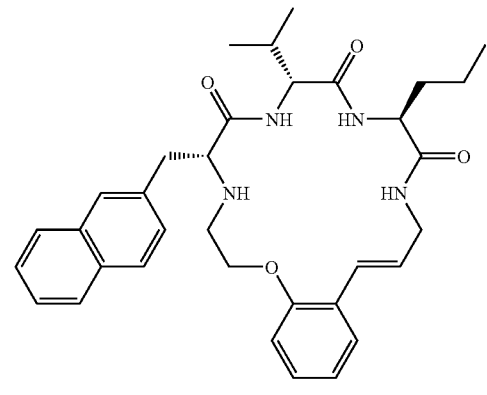
181
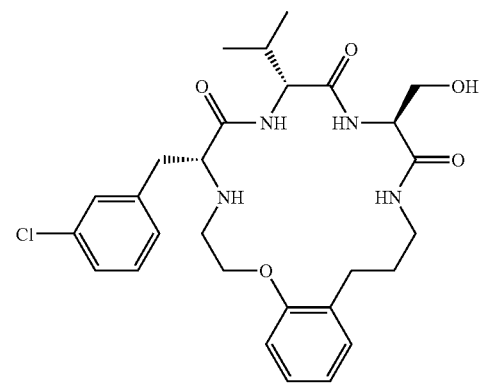
24
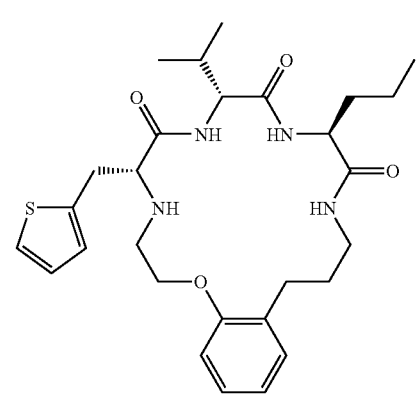
2
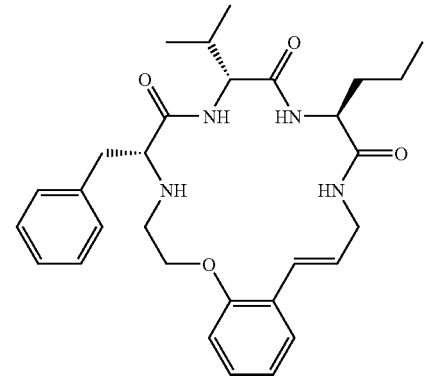
200
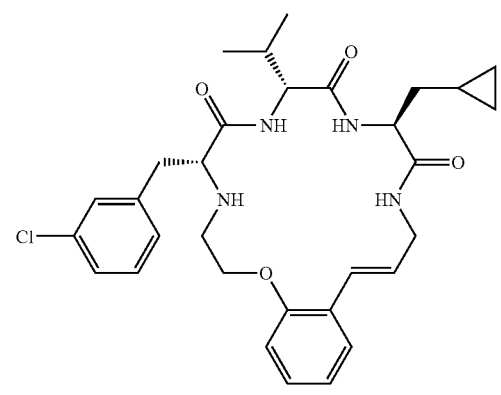

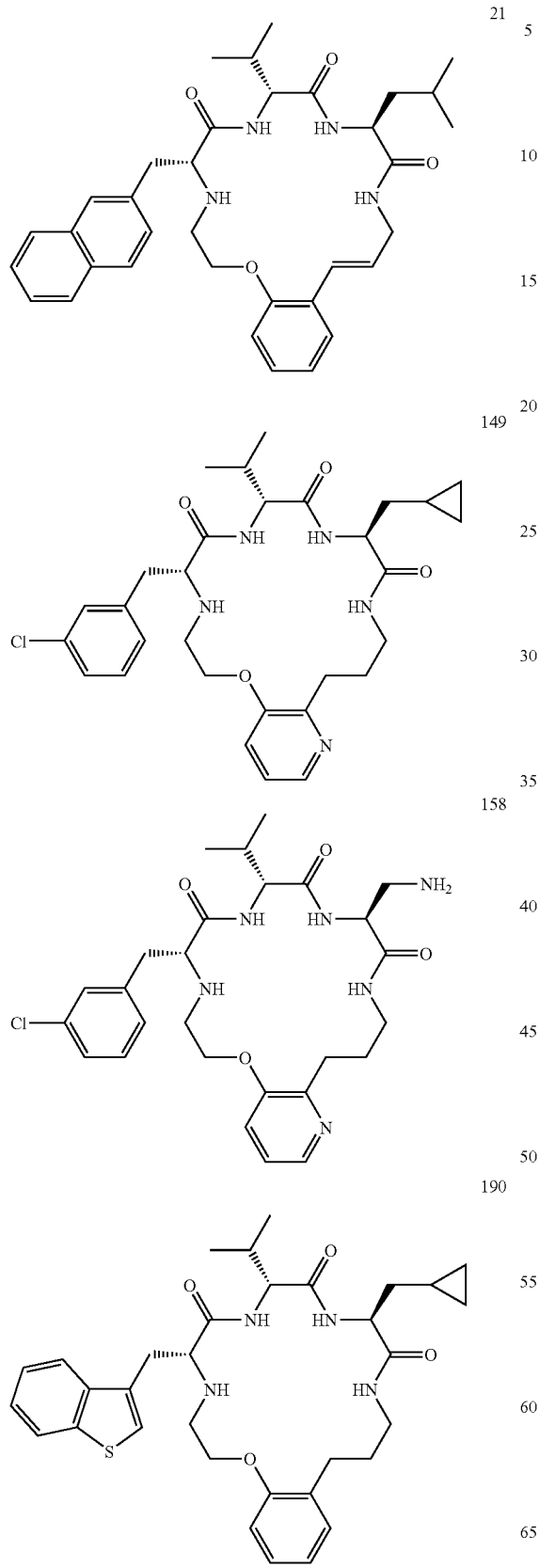
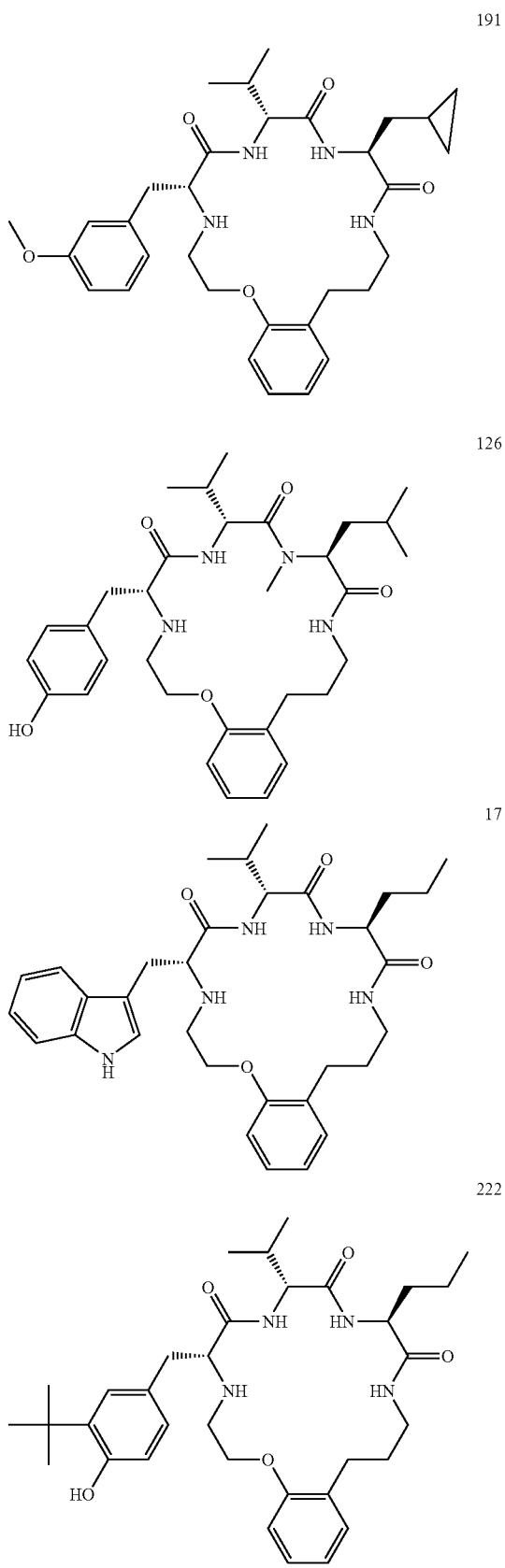

-continued
193
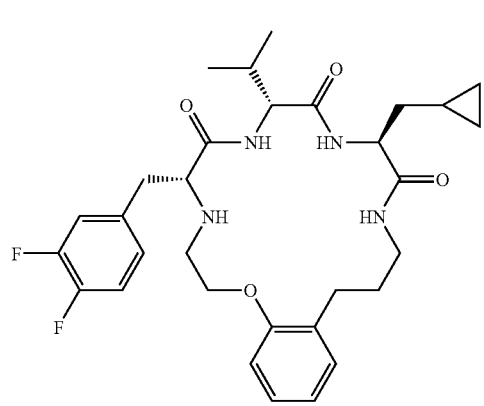
171
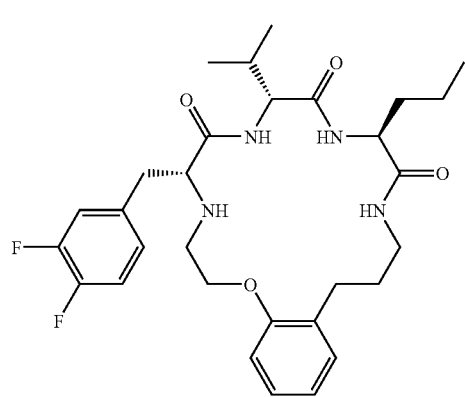
142
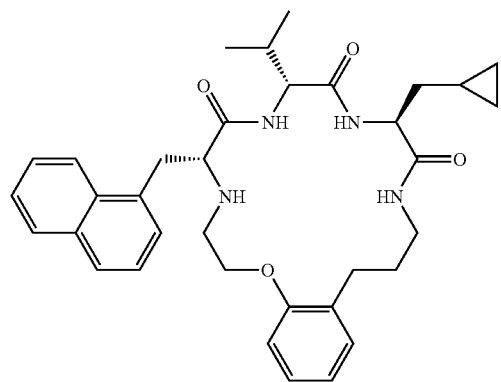
187
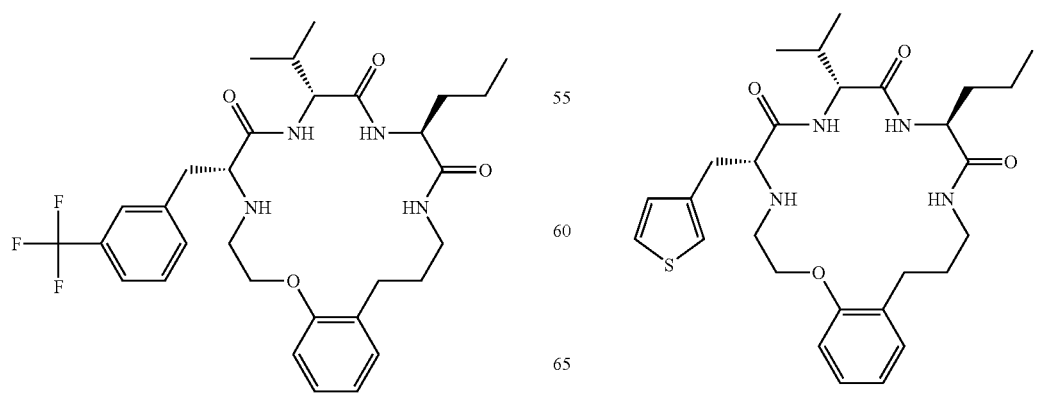
-continued
163
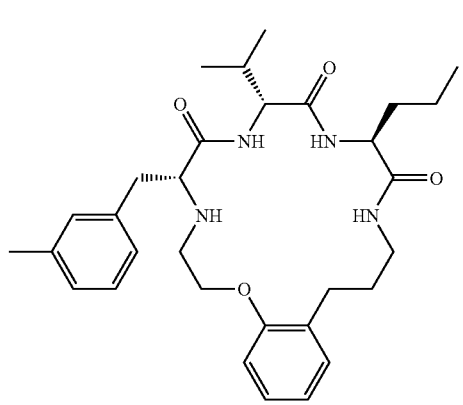
167
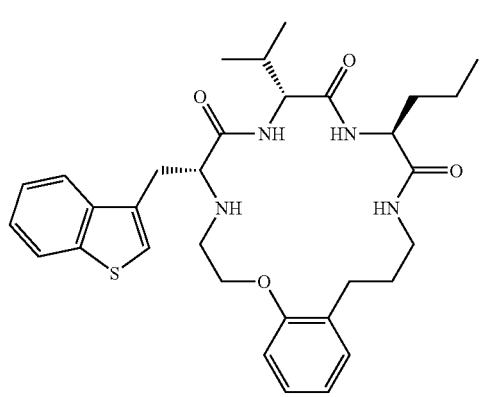
23
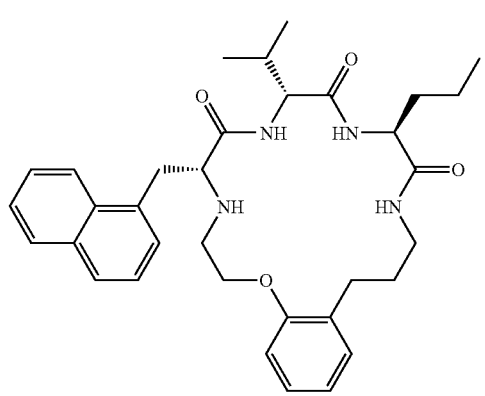
168
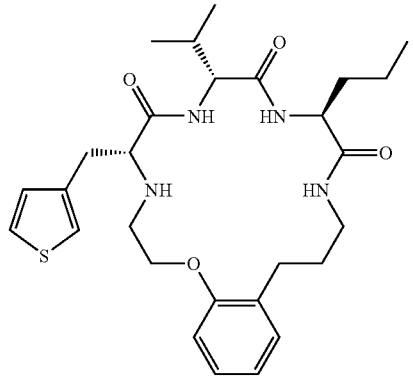

-continued
170
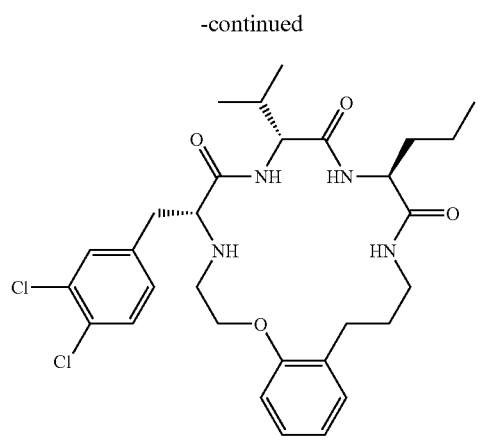
220
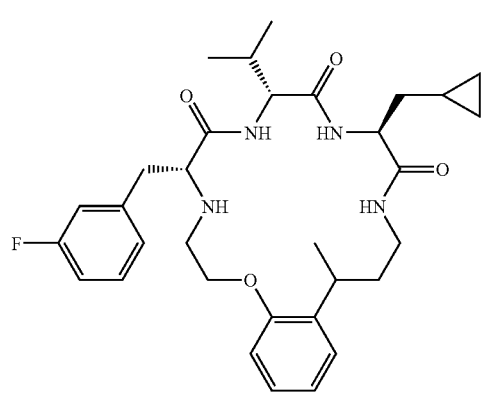
133
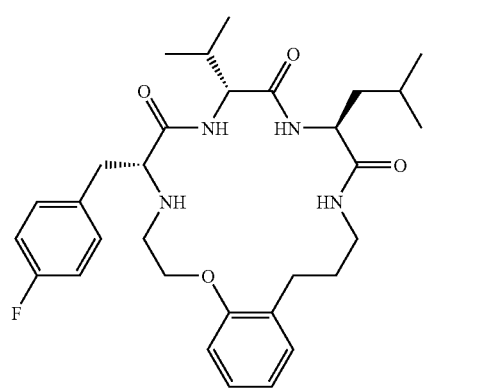
216
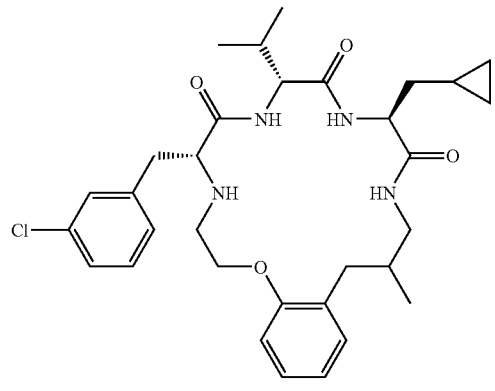
-continued
198
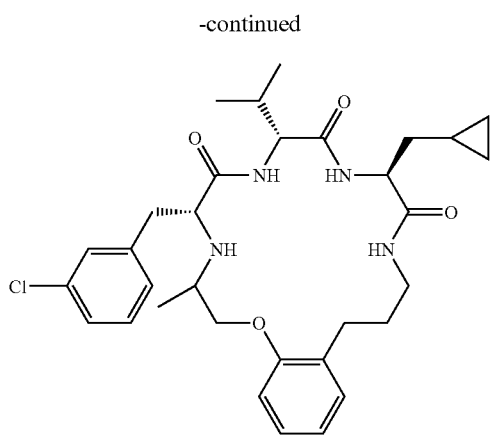
192
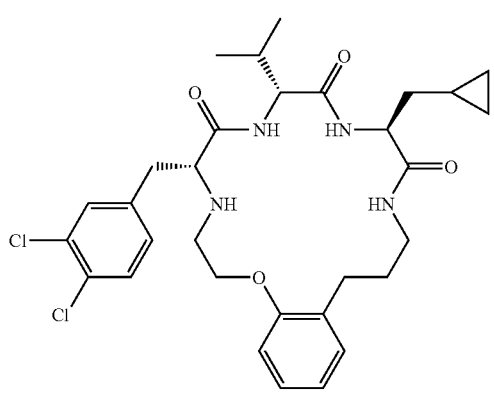
146
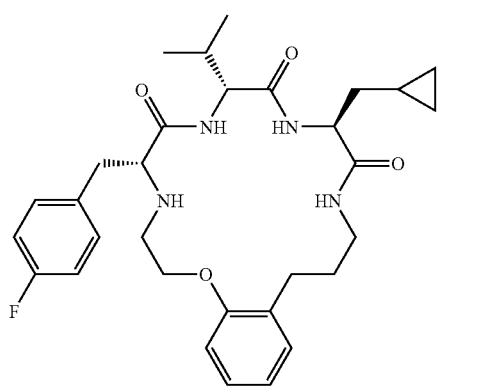
19
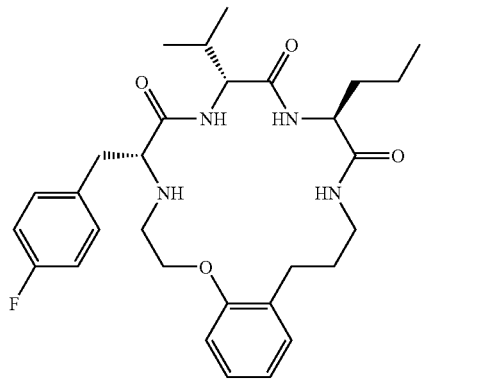

-continued
22
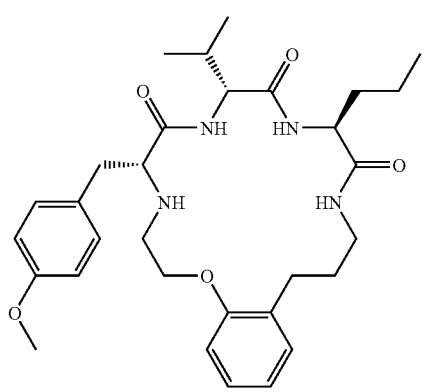
172
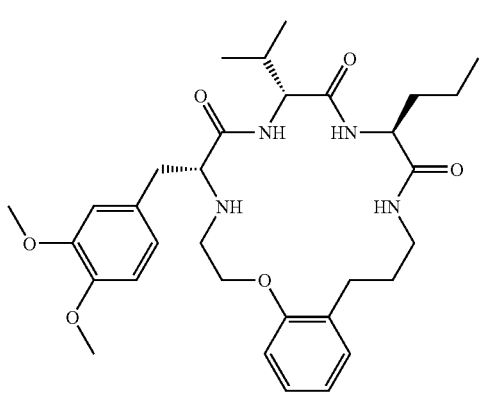
165
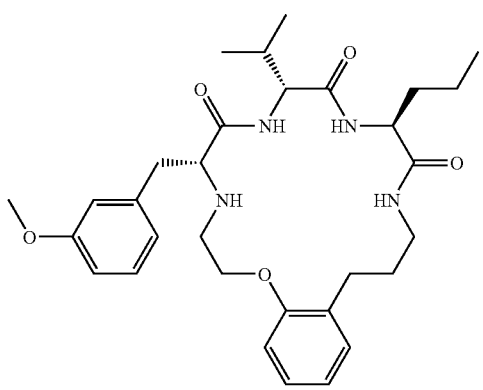
144
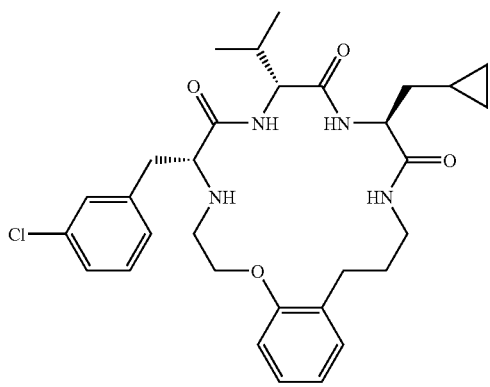
-continued
131
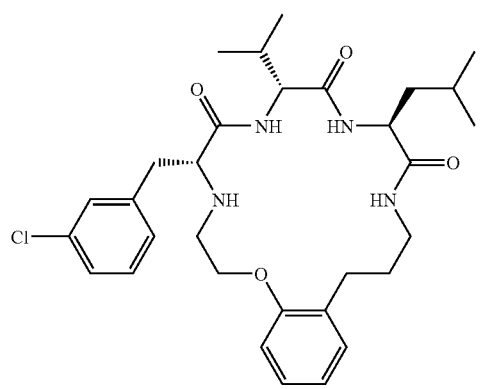
204
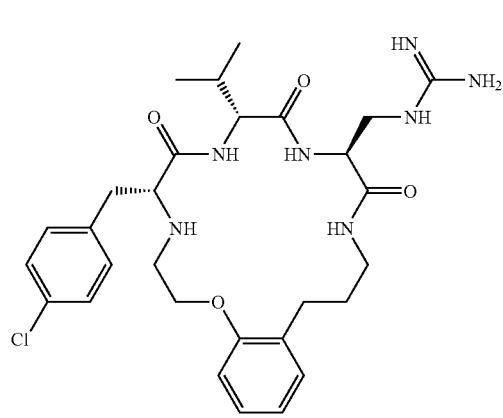
15
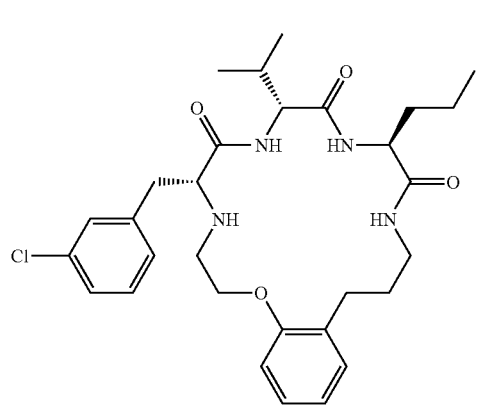
218
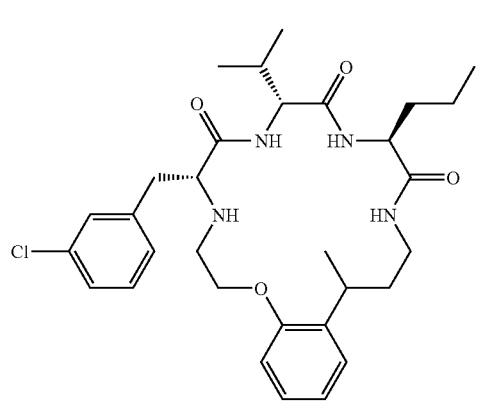

-continued
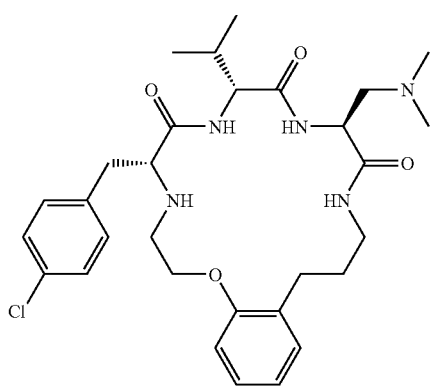
211
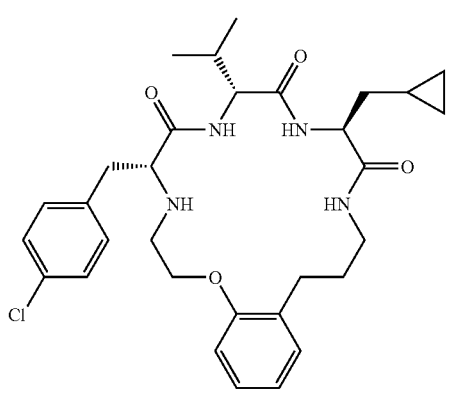
145
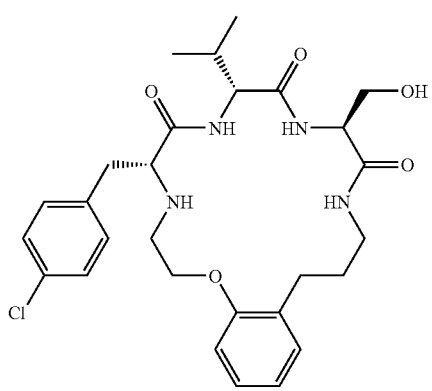
182
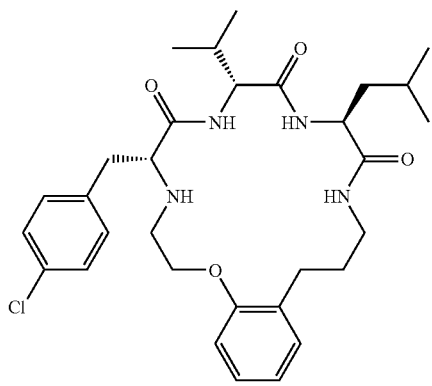
132
-continued
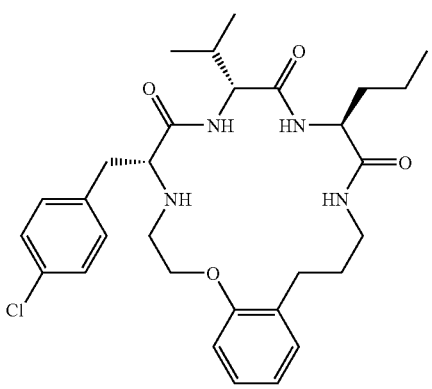
16
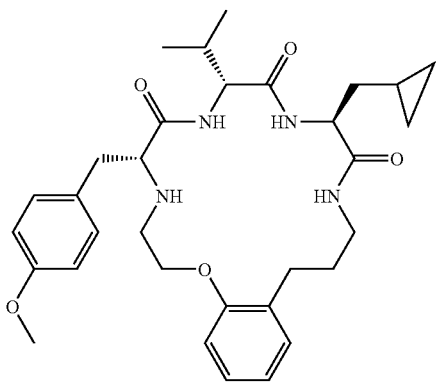
141
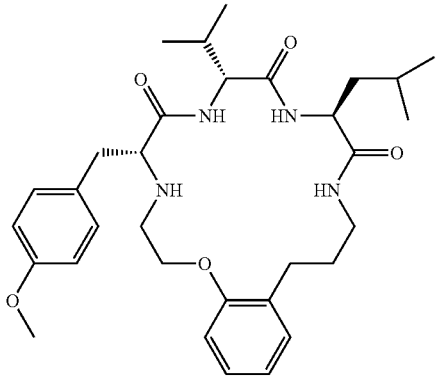
128
In addition to the preferred tethers (T) illustrated previously, other specific tethers employed for compounds of the invention are shown hereinbelow:
T2
HO⁀⁀⁀NHPG
T8
[structure with phenyl, vinyl, NHPG, and O-CH2CH2-OH]
T9
[structure with phenyl, propyl-NHPG, and O-CH2CH2-OH]

-continued

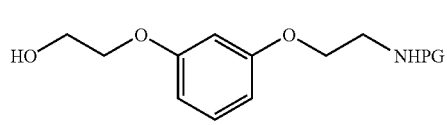

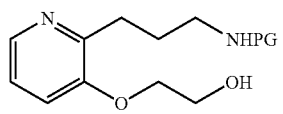

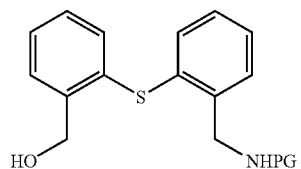

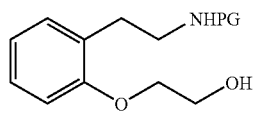

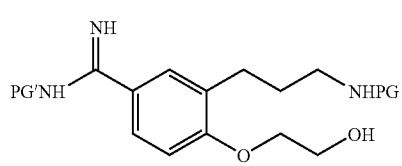

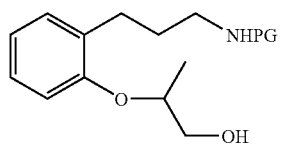

T33a [(R)-isomer]
T33b [(S)-isomer]

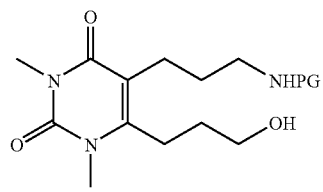

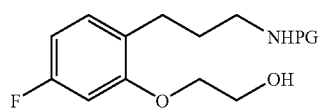

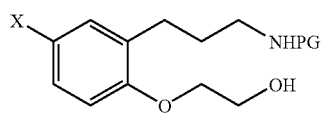

T36 (X = F)
T37 (X = Cl)

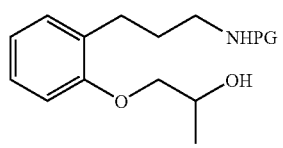

-continued

T10

T11

T12

T28

T32

T34

T35

T38

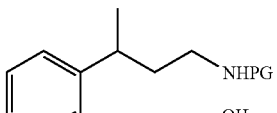  T39

T40

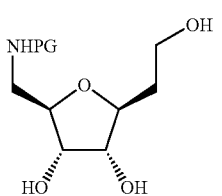  T41

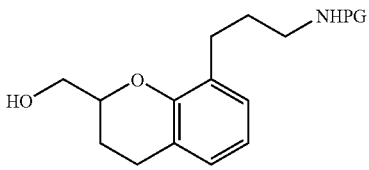  T42

PG and PG' indicate a standard amine protecting group compatible with the synthetic protocol, such as Boc, Ddz, Fmoc, or Alloc In a preferred embodiment, the present invention is directed to a method of treating irritable bowel syndrome, dyspepsia, Crohn's disease, gastroesophogeal reflux disorders, ulcerative colitis, pancreatitis, infantile hypertrophic pyloric stenosis, carcinoid syndrome, malabsorption syndrome, diarrhea, diabetes mellitus, obesity, postgastroenterectomy syndrome, atrophic colitis or gastritis, gastric stasis, gastrointestinal dumping syndrome, celiac disease and eating disorders leading to obesity in humans and other mammals comprising administering a therapeutically effective amount of a compound of formula (I).

Synthetic Methods

A. General Information

Reagents and solvents were of reagent quality or better and were used as obtained from various commercial suppliers unless otherwise noted. DMF, DCM and THF used are of DriSolv® (EM Science, now EMD Chemicals, Inc., part of Merck KgaA, Darmstadt, Germany) or synthesis grade quality except for (i) deprotection, (ii) resin capping reactions and (iii) washing. NMP used for the amino acid (AA) coupling reactions is of analytical grade. DMF was adequately degassed by placing under vacuum for a minimum of 30 min prior to use. Tyr(3tBu) was synthesized following the method reported in JP2000 44595. Cpa was made using literature methods (Tetrahedron: Asymmetry 2003, 14, 3575-3580) or obtained commercially. Boc- and Fmoc-protected amino acids and side chain protected derivatives, including those of N-methyl and unnatural amino acids, were obtained from commercial suppliers or synthesized through standard methodologies known to those in the art. Ddz-amino acids were either synthesized by standard procedures or obtained commercially from Orpegen (Heidelberg, Germany) or Advanced ChemTech (Louisville, Ky., USA). Bts-amino acids were synthesized as described in Example 6. Hydroxy acids were obtained from commercial suppliers or synthesized from the corresponding amino acids by literature methods. Analytical TLC was performed on pre-coated plates of silica gel 60F254 (0.25 mm thickness) containing a fluorescent indicator. The term "concentrated/evaporated under reduced pressure" indicates evaporation utilizing a rotary evaporator under either water aspirator pressure or the stronger vacuum provided by a mechanical oil vacuum pump as appropriate for the solvent being removed. "Dry pack" indicates chromatography on silica gel that has not been pre-treated with solvent, generally applied on larger scales for purifications where a large difference in $R_f$ exists between the desired product and any impurities. For solid phase chemistry processes, "dried in the standard manner" is that the resin is dried first in air (1 h), and subsequently under vacuum (oil pump usually) until full dryness is attained (~30 min to O/N).

B. Synthetic Methods for Building Blocks of the Invention

Example 6

Standard Procedure for the Synthesis of Bts-Amino Acids

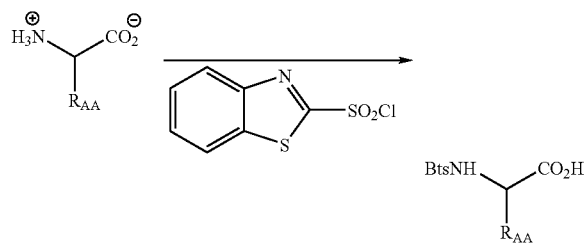

To a solution of the amino acid or amino acid derivative (0.1 mol, 1.0 eq) in 0.25 N sodium hydroxide (0.08 mol, 0.8 eq) with an initial pH of approximately 9.5 (pH meter) at rt, solid Bts-Cl (0.11 mol, 1.1 eq) was added in one portion. The resulting suspension was stirred vigorously for 2-3 d. The pH of the reaction should be adjusted with 5.0 N sodium hydroxide as required to remain within the range 9.5-10.0 during this time. Typically, the pH has to be adjusted every 20-30 min during the first 5 h. Once the pH stops dropping, it is an indication that the reaction is almost complete. This can be confirmed by TLC (EtOAc:MeOH, 95:5). Upon completion, the reaction mixture was washed with $Et_2O$. Washing is continued until the absence of non-polar impurities in the aqueous layer is confirmed by TLC (typically 3×100 mL). The aqueous solution was then cooled to 0° C., acidified to pH 2.0 with 1 N HCl until no additional cloudiness forms, and extracted with EtOAc (3×100 mL). Alternatively, a mixture of DCM and EtOAc may be used as the extraction solvent, depending on the solubility of the product obtained from different amino acids or derivatives. Note that DCM cannot be used solely as solvent because of the emulsion formed during extraction. The combined organic phases were washed with brine (2×150 mL), dried over $MgSO_4$, filtered and evaporated under reduced pressure. DCM (1×) and hexanes (2×) were evaporated from the residue in order to ensure complete removal of the EtOAc and give the desired compound as a solid in 55-98% yield.

The following are modifications that have proven useful for certain amino acids:

Gly, Ala, D-Ala, β-Ala and GABA: Use 1.5 eq of amino acid per eq of Bts-Cl, in order to prevent dibetsylation.

Met: Carry out the reaction under $N_2$ to prevent oxidation.

Gln and Asn: Due to the solubility of Bts-Gln and Bts-Asn, the work-up required is modified from the standard procedure: Upon completion of the reaction, the reaction mixture was washed with diethyl ether. Washing is continued until the absence of non-polar impurities in the aqueous layer is confirmed by TLC (typically 3×100 mL). The aqueous phase was then cooled to 0° C. and acidified to pH 2.0 with 6 N HCl. 6 N HCl was employed to minimize the volume of the solution due to the water solubility of Bts-Gln and Bts-Asn. (They are, in contrast, difficult to dissolve in DCM, EtOAc or chloroform.) The solution was maintained at 0° C. for 10 min and the product was collected by filtration as a white precipitate. The solid was washed with cold water (1×), cold brine (2×) and water (1×, 25° C.). The pH of this wash was taken, if it is not approximately 4, the solid was washed again with water. Finally, the solid was washed with cold EtOAc, then with cold $Et_2O$ (2×), and finally dried under vacuum (oil pump) (83-85% yield).

C. General Synthetic Strategy to Conformationally-Defined Macrocycles of the Present Invention The compounds of Formula I can be synthesized using traditional solution synthesis techniques or solid phase chemistry methods. In either, the construction involves four phases: first, synthesis of the building blocks, including one to four moieties, comprising recognition elements for the biological target receptor, plus one tether moiety, primarily for control and definition of conformation. These building blocks are assembled together, typically in a sequential fashion, in a second phase employing standard chemical transformations. The precursors from the assembly are then cyclized in the third stage to provide the macrocyclic structures. Finally, a post-cyclization processing stage involving removal of protecting groups and optional purification then provides the desired final compounds (see FIG. 1). This method has been previously disclosed in WO 01/25257 and U.S. patent application Ser. No. 09/679,331. A general synthetic strategy is shown in FIG. 1.

Figure 2:
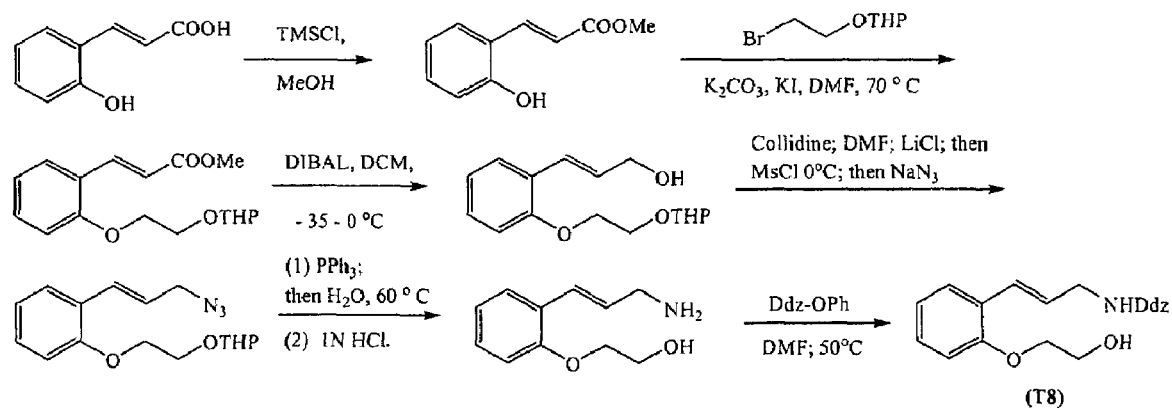
FIG. 2 depicts the standard procedure for the synthesis of tether T8.

D. Procedures for the Synthesis of Representative Tethers of the Present Invention The important tether component required for compounds of the invention are synthesized as described in WO01/25257, U.S. Provisional Pat. Appl. Ser. No. 60/491,248 or herein. A standard procedure for the synthesis of tether B is shown in FIG. 2.

Step T8-1: Chlorotrimethylsilane (116 mL, 0.91 mol, 1.5 eq) was added to a suspension of 2-hydroxycinnamic acid (100 g, 0.61 mol, 1.0 eq) in MeOH (500 mL, HPLC grade) over 30 min at 0° C. The resulting mixture was stirred at rt O/N. The reaction was monitored by TLC (EtOAc/MeOH:98/2). Heating the reaction mixture in a hot water can accelerate the process if necessary. After the reaction was completed, the reaction mixture was evaporated under reduced pressure to afford methyl 2-hydroxycinnamate as a white solid (108.5 g) in quantitative yield. The identity of this intermediate compound is confirmed by NMR. This reaction can be carried out on larger (kg) scale with similar results Step T8-2: 3,4-Dihydro-2H-pyran (DHP, 140 mL, 1.54 mol, 2.52 eq) was added dropwise to 2-bromoethanol (108 mL, 1.51 mol, 2.5 eq) in a 2 L three-neck flask with mechanical stirring at 0° C. over 2 h. The resulting mixture was stirred for additional 1 h at rt. Methyl 2-hydroxycinnamate from Step T8-1 (108 g, 0.61 mol, 1.0 eq), potassium carbonate (92.2 g, 0.67 mol, 1.1 eq), potassium iodide (20 g, 0.12 mol, 0.2 eq) and DMF (300 mL, spectrometric grade) were added to the above flask. The reaction mixture was stirred at 70° C. (external temperature) for 24 h. The reaction was monitored by TLC (DCM/Et$_2$O: 95/5). The reaction was allowed to cool to rt and Et$_2$O (450 mL) was added. The inorganic salts were removed by filtration and washed with Et$_2$O (3×50 mL). The filtrate was diluted with hexanes (400 mL) and washed with water (3×500 mL), dried over MgSO$_4$, filtered and the filtrate evaporated under reduced pressure. The crude ester (desired product and excess Br—C$_2$H$_4$—OTHP) was used for the subsequent reduction without further purification.

Step T8-3: DIBAL (1.525 L, 1.525 mol, 2.5 eq, 1.0 M in DCM) was added slowly to a solution of the above crude ester from Step T8-2 (0.61 mol based on the theoretical yield) in anhydrous DCM (610 mL) at −35° C. with mechanical stirring over 1.5 h. The resulting mixture was stirred for 1.5 h at −35° C., then 1.5 h at 0° C. The reaction was monitored by TLC (hex/EtOAc:50/50). When complete, Na$_2$SO$_4$.10H$_2$O (100 g, 0.5 eq) was slowly added; hydrogen evolution was observed, when it subsided water was added (100 mL). The mixture was warmed to rt and stirred for 10 min, then warmed to 40° C. with hot water and stirred under reflux for 20 min. The mixture was cooled to rt, diluted with DCM (600 mL), and the upper solution decanted into a filter. The solid that remained in the flask was washed with dichloromethane (5×500 mL) with mechanical stirring and filtered. The filtrate from each wash was checked by TLC, and additional washes performed if necessary to recover additional product. In an alternative work-up procedure, after dilution with DCM (600 mL), the mixture was filtered. The resulting solid was then continuously extracted with 0.5% TEA in dichloromethane using a Soxhlet extractor. Higher yield was typically obtained by this alternative procedure, although it does require more time. The filtrate was concentrated under reduced pressure and the residue purified by dry pack (EtOAc/hex/Et$_3$N: 20/80/0.5) to give the product alcohol as a yellowish oil (yield: 90%). The identity and purity were confirmed by NMR.

Step T8-4: To a mixture of the allylic alcohol from Step T8-3 (28 g, 0.100 mol, 1.0 eq) and collidine (0.110 mol, 1.1 eq) in 200 mL of anhydrous DMF under N$_2$ was added anhydrous LiCl (4.26 g, 0.100 mol, 1.0 eq.) dissolved in 100 mL of anhydrous DMF. The mixture was then cooled to 0° C., and MsCl (12.67 g, 0.110 mol, 1.1 eq., freshly distilled over P$_2$O$_5$), was added dropwise. The reaction was allowed to warm to rt and monitored by TLC (3:7 EtOAc/hex). When the reaction was complete, NaN$_3$ (32.7 g, 0.500 mol, 5.0 eq.) was added. The reaction mixture was stirred at rt O/N with progress followed by NMR. When the reaction was complete, the mixture is poured into an ice-cooled water bath, and extracted with diethyl ether (3×). The combined organic phases were then washed sequentially with citrate buffer (2×), saturated sodium bicarbonate (2×), and finally with brine(1×). The organic layer was dried with MgSO$_4$, filtered and the filtrate concentrated under reduced pressure. The allylic azide was obtained in 90% combined yield, and was of sufficient quality to use as such for the following step.

Step T8-5: PPh$_3$ (25.9 g, 0.099 mol, 1.5 eq) was added at 0° C. to a solution of the allylic azide from Step T8-4 (20.0 g, 0.066 mol, 1.0 eq.) in 100 mL of THF. The solution was stirred for 30 min at 0° C. and 20 h at rt. Water (12 mL) was then added and the resulting solution was heated at 60° C. for 4 h. The solution was cooled to rt, 2N HCl (15 mL) added and the mixture stirred for 90 min at 50° C. The separated organic phase was extracted with 0.05 N HCl (2×100 mL). The combined aqueous phase was washed with Et$_2$O (5×150 mL) and toluene (4×150 mL) (more extraction could be necessary, follow by TLC), which were combined and back-extracted with 0.05 N HCl (1×100 mL). This acidic aqueous phase from back-extraction was combined with the main aqueous phase and washed with ether (5×150 mL) again. The pH of the aqueous phase was then adjusted to 8-9 by the addition of sodium hydroxide (5 N). Care must be exercised to not adjust the pH above 9 due to the reaction conditions required by the next step. The aqueous phase was concentrated under reduced pressure (aspirator, then oil pump) or lyophilized to dryness. Toluene (2×) was added to the residue and then also evaporated under reduced pressure to remove traces of water. The crude product (desired amino alcohol along with inorgnic salt) was used for the next reaction without further purification.

Step T8-6: A mixture of the crude amino alcohol from Step T8-5 (0.5 mol based on the theoretical yield), Ddz-OPh (174 g, 0.55 mol, 1.1 eq) and Et$_3$N (70 mL, 0.5 mol, 1.0 eq) in DMF (180 mL) was stirred for 24 h at 50° C. Additional DMF is added if required to solubilize all materials. The reaction was monitored by TLC (hex/EtOAc:50/50, ninhydrin detection). After the reaction was complete, the reaction mixture was diluted with Et$_2$O (1.5 L) and water (300 mL). The separated aqueous phase was extracted with Et$_2$O (2×150 mL). The combined organic phase was washed with water (3×500 mL) and brine (1×500 mL), dried over MgSO$_4$, filtered and the filtrate concentrated under reduced pressure. The layers were monitored by TLC to ensure no product was lost into the aqueous layer. If so indicated, perform one or more additional extractions with Et$_2$O of the aqueous phase to recover this material. The crude product was purified by dry pack (recommended column conditions: EtOAc/hex/Et$_3$N: 35/65/0.5 to 65/35/0.5) to give the tether Ddz-T8 as a pale yellow syrup (yield: ~40%). The identity and purity of the product was confirmed by NMR.

$^1$H NMR (DMSO-d$_6$): 1.6 ppm (s, 6H, 2×CH$_3$), 3.6-3.8 ppm (wide s, 10H, 2×OCH$_3$, 2×OCH$_2$), 3.95 ppm (triplet, 2H, CH$_2$N), 6-6.2 ppm (m, 2H, 2×CH), 6.2-6.5 ppm (m, 3H, 3×CH, aromatic), 6.6-7.6 ppm (m, 5H, aromatic).

Figure 3:
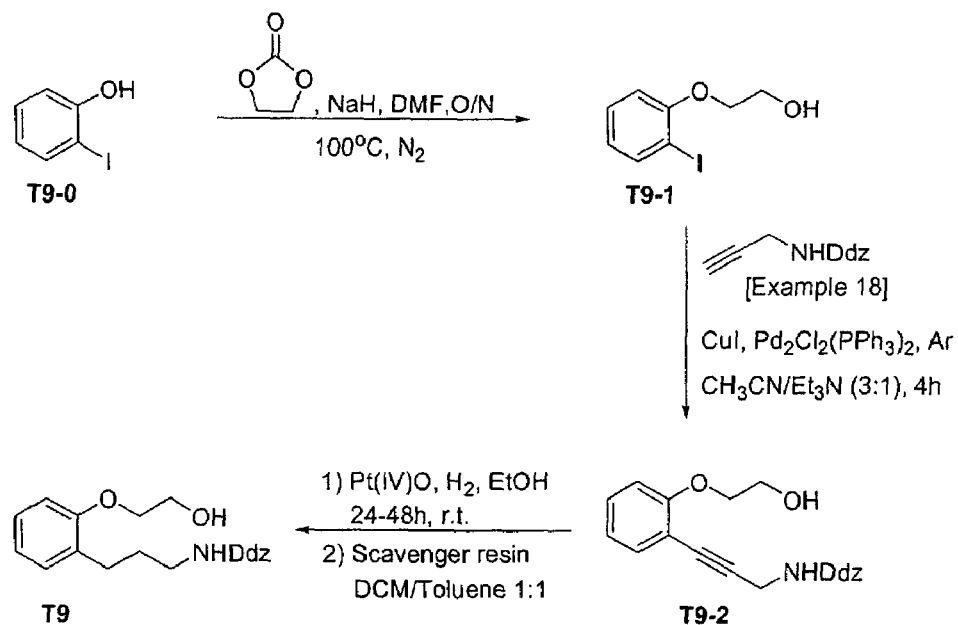
FIG. 3 depicts the standard procedure for the synthesis of tether T9.

A standard procedure for the synthesis of tether T9 is shown in FIG. 3.

Tether T9 can also be synthesized from T8 by reduction as in step T9-3 or with other appropriate hydrogenation catalysts known to those in the art.

Figure 4:
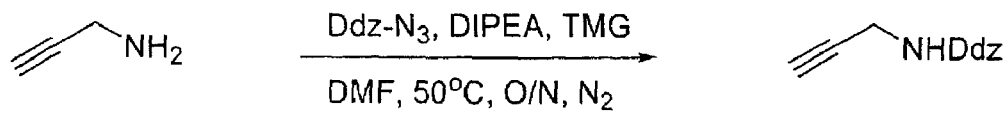
FIG. 4 depicts the standard procedure for the synthesis of Ddz-propargylamine.

A standard procedure for the synthesis of Ddz propargylamine is shown in FIG. 4.

In a dried three-neck flask, a solution of propargylamine (53.7 g, 0.975 mol, 1.5 eq) in degassed DMF (Drisolv, 388 mL) was treated with Ddz-N$_3$ (170.9 g, 0.65 mol, 1.0 eq), tetramethylguanidine (TMG, 81.4 mL, 0.65 mol, 1.0 eq) and DIPEA (113.1 mL, 0.65 mol, 1.0 eq) and stirred at 50° C. O/N. The reaction was monitored by TLC (conditions:25/75 EtOAc/hex. $R_f$: 0.25; detection: UV, ninhydrin). Upon completion, DMF was evaporated under reduced pressure until dryness and the residue dissolved in $Et_2O$ (1 L). The organic solution was washed sequentially with citrate buffer (pH 4.5, 3×), saturated aqueous sodium bicarbonate (2×), and brine (2×), then dried with $MgSO_4$, filtered and the filtrate evaporated under reduced pressure. A pale orange solid was obtained. This solid was triturated with 1% EtOAc in hex, then collected by filtration and dried under vacuum (oil pump) to provide the desired product (153.4 g, 85.2%).

Figure 5A:
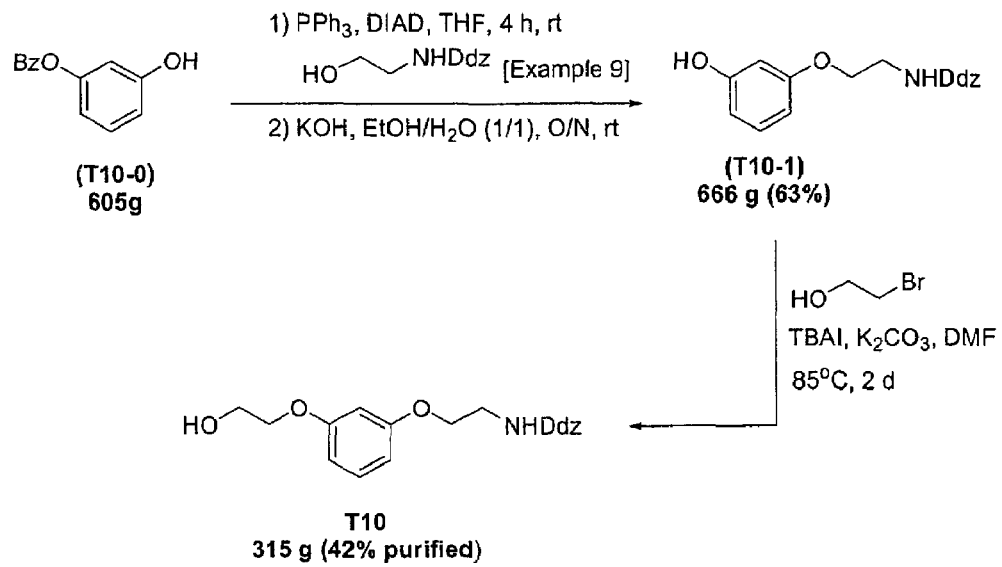
FIG. 5A depicts the standard procedure for the synthesis of tether T10.

A standard procedure for the synthesis of tether T10 is shown in FIG. 5A.

Two alternative routes to this tether have been developed. The first synthetic approach proceeded starting from the commercially available monobenzoate of resorcinol (T10-0). Mitsunobu reaction under standard conditions with the protected amino alcohol from Example 9, followed by saponification of the benzoate provided T10-1 in good yield after recrystallization. Alkylation of the phenol with 2-bromoethanol using the optimized conditions shown permitted the desired product Ddz-T10 to be obtained after dry pack purification in 42% yield.

Figure 5B:
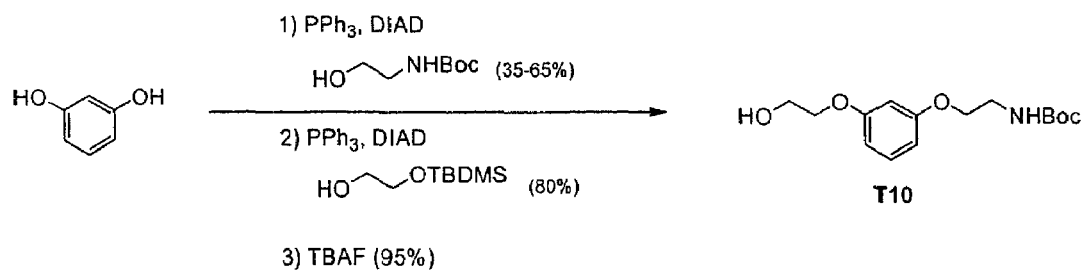
FIG. 5B depicts the second synthetic route to tether T10.

A second synthetic route to T10 is shown in FIG. 5B.

From resorcinol, two successive Mitsunobu reactions are conducted with the appropriate two carbon synthons illustrated, themselves derived from 2-aminoethanol and ethylene glycol, respectively, through known protection methodologies. Lastly, deprotection of the silyl ether, also under standard conditions provided Boc-T10.

Although the yields in the two methods are comparable, the first required less mechanical manipulation and is preferred for larger scales.

Figure 6:
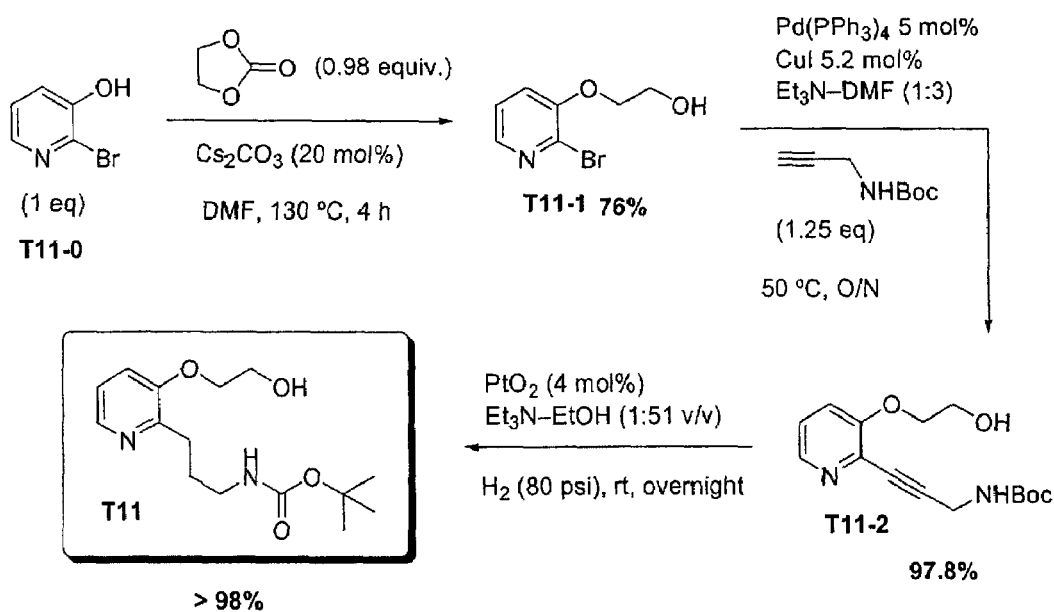
FIG. 6 depicts the standard procedure for the synthesis of Tether T11.

A standard procedure for the synthesis of tether T11 is shown in FIG. 6.

Figure 7:
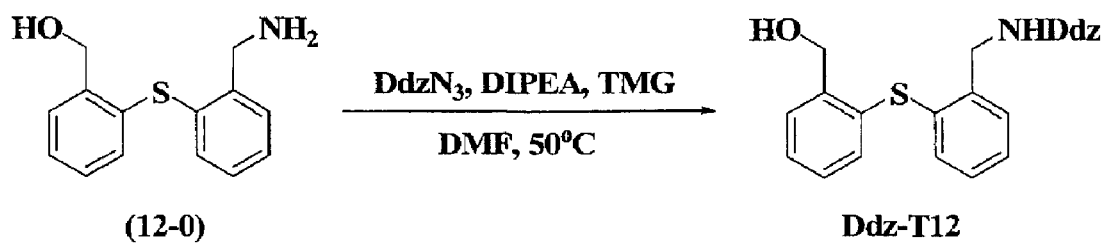
FIG. 7 depicts the standard procedure for the synthesis of tether T12.

A standard procedure for the synthesis of tether T12 is shown in FIG. 7.

In a 3-L flame-dried three-neck flask, a solution of (aminomethyl)phenylthiobenzyl alcohol (12-0, 96 g, 0.39 mol) in degassed DMF (1 L, 0.4 M) was prepared. To this was added $DdzN_3$ (0.95 eq), followed by TMG (0.39 mol, 49 mL). The reaction was stirred for 10 min, then DIPEA (68 mL, 0.39 mol) added. The mixture was heated at 50° C. under $N_2$ until TLC indicated no $DdzN_3$ remained (48 h typically). (TLC eluent: EtOAc:Hex 50:50; detection: ninhydrin). Upon completion, to the reaction mixture was added 3 L citrate buffer and the separated aqueous layer extracted with $Et_2O$ (3×1500 mL). The combined organic phase was washed sequentially with citrate buffer (2×200 mL), water (2×200 mL) and brine (2×200 mL). The organic layer was dried over $MgSO_4$, filtered and the filtrate evaporated under reduced pressure. A dark orange oil was obtained, which was purified by dry-pack. For this procedure, the oil was first dissolved in EtOAc:Hex:DCM:TEA (20:80:1:0.5, v/v/v/v). At this point, a little extra DCM was sometimes required to ensure complete dissolution. The solution was loaded onto the column, then the column eluted with EtOAc:Hex:DCM:$Et_3N$ (20:80:1:0.5) until all the impurities were separated out as indicated by TLC, paying particular attention to that closest to the desired product. The elution was then continued with EtOAc:Hex:$Et_3N$ 30:70:0.5 (v/v/v) and finally with EtOAc:hexanes:$Et_3N$ (50:50:0.5) to elute the desired product. After removal of the solvent from the fractions containing the product under reduced pressure, the residue was dissolved in the minimum amount of DCM, a three-fold larger volume of hexanes added, then the solvents again evaporated under reduced pressure. This treatment was repeated until an off-white foam was obtained. The latter solidified while drying under vacuum (oil pump). Alternatively, the material yielded a solid after sequential concentration with DCM (1×) and hexanes (2×). Tether Ddz-T12 was obtained as an off-white solid (85-90% yield).

Example 29

Standard Procedure for Attachment of Tethers Utilizing the Mitsunobu Reaction

Example 29-A

Using $PPh_3$-DIAD Isolated Adduct

To a 0.2 M solution of the appropriate tether (1.5 eq) in THF or THF-toluene (1:1) was added the $PPh_3$-DIAD (preformed by mixing equivalent amounts of the reagents and isolated by evaporation of solvent, see Example 29-C) adduct (1.0 eq.). The resultant mixture was manually agitated for 10 sec (the solution remained turbid), then added to the resin. Alternatively, the resin was added to the solution. The reaction suspension was agitated O/N (after ~5 min the mixture becomes limpid). The resin was filtered and washed 2×DCM, 1× toluene, 1×EtOH, 1× toluene, 1×(DCM/MeOH), 1×(THF/MeOH), 1×(DCM/MeOH), 1×(THF/MeOH), 2×DCM, then dried in the standard manner.

Example 29-B

Using "$PPh_3$-DIAD In Situ Procedure"

To a 0.2 M solution of the appropriate tether (4 eq) in THF or THF-toluene (1:1) was added triphenylphosphine (4 eq). The resultant mixture was manually shaken until a homogenous solution was obtained, then added to the resin. Alternatively, the resin (or IRORI™ MiniKans® (NEXUS Biosystems, Poway, Calif.), miniaturized microreactors, containing resin) was added to the solution. To this suspension was then added DIAD (3.9 eq) and the reaction agitated O/N. Note: Since the reaction is exothermic, for larger scales, the reaction should be cooled in an ice bath. In addition, an appropriate vent must be supplied to allow any pressure build-up to be released. The resin was filtered and washed DCM (2×), toluene (1×), EtOH (1×), toluene (1×), DCM/MeOH (1×), 1×THF/MeOH (1×), DCM/MeOH (1×), THF/MeOH (1×), 2×DCM, then dried in the standard manner.

Figure 8:
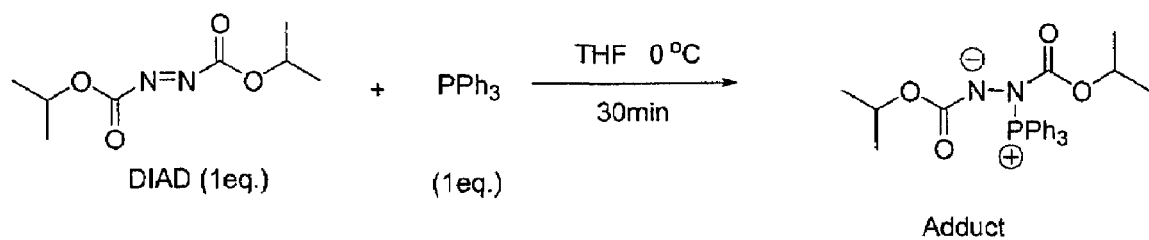
FIG. 8 depicts the procedure for synthesis of PPh$_3$-DIAD adduct of Example 29-C.

A procedure for the synthesis of $PPh_3$-DIAD adduct is shown in FIG. 8.

DIAD (1 eq) was added dropwise to a well-stirred solution of triphenylphosphine (1 eq) in THF (0.4 M) at 0° C. under nitrogen. The mixture was then maintained at 0° C. with stirring for 30 min. The white solid obtained was collected by filtration (use medium sized fritted filters), washed with cold anhydrous THF until the washes were colorless, and lastly washed once with anhydrous $Et_2O$. The white solid product was then vacuum-dried (oil pump) and stored under nitrogen. (Note: The $PPh_3$-DIAD adduct can be made in larger than immediately required quantity and stored under nitrogen; it is very important to store this reagent under anhydrous conditions.)

Example 30

Figure 9:
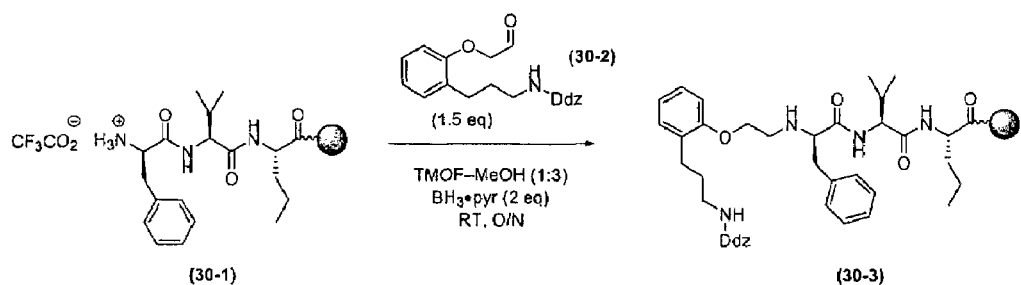
FIG. 9 depicts the standard procedure for attachment of tethers via reductive amination of Example 30.

Standard Procedure for Attachment of Tethers via Reductive Amination as Shown in FIG. 9

In certain instances, the Mitsunobu process of Example 29 cannot be applied or is not efficient for incorporation of the tether. Hence, reductive amination has been developed as an alternative that can be employed for tether incorporation as illustrated hereinbelow for one of the preferred tethers. Similar chemistry can be used to incorporate other tethers of the present invention.

The Tether (30-2) with the amine protected as its Ddz derivative was efficiently oxidized to the corresponding aldehyde 30-2 using $SO_3$.pyr in DMSO-$Et_3$N-DCM. This aldehyde (0.14 mmol, 56 mg, 1.5 eq based upon loading of resin support) was dissolved in a 1:3 mixture of TMOF-MeOH (DriSolv, 4 mL) at rt. To this was added the resin containing the tripeptide (30-1, as its trifluoroacetic acid salt from the deprotection of the terminal amine), the mixture was agitated briefly to wet the resin, and then borane-pyridine complex (as the commercially available 8 M solution, 23 µL, 2 eq) was introduced to the suspension. The reaction was agitated O/N, then the resin filtered, washed with DCM (2×), THF (1×), DCM/MeOH [3:1] (1×), THF/MeOH [3:1] (1×), DCM (2×) and dried in the standard manner. Care must be taken to ensure that the desired resin bound product 30-3 is not contaminated with the dialkylated material. However, even if the reaction does not proceed to completion or if a small amount of the dialkylation side product is present, the material is of sufficient purity for the macrocyclization reaction.

Figure 10:
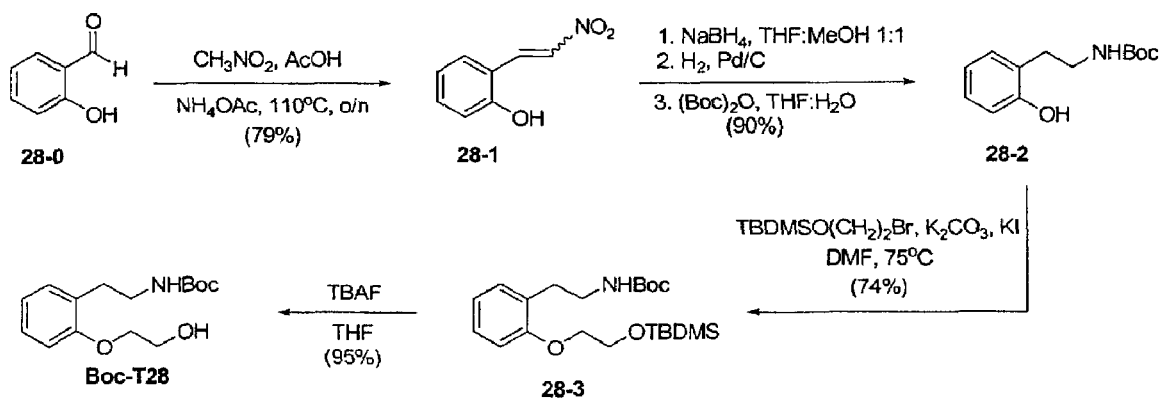
FIG. 10 depicts the standard procedure for the synthesis of tether T28.

A standard procedure for the synthesis of tether T28 is shown in FIG. 10.

Henry reaction of 2-hydroxybenzaldehyde 28-0 provided 28-1 in 79% yield. This was followed by reduction first with sodium borohydride, then with catalytic hydrogenation, to give the amine, which was then protected as its Boc derivative, 28-2. Yields of these first two steps were lower on larger scales. Alkylation of 28-2 with the TBDMS ether of 2-bromoethanol, itself synthesized by standard methods, gave 28-3 in 74% yield. Deprotection of the silyl ether under standard conditions yielded the desired protected tether, Boc-T28. Alternative use of ethylene carbonate for the phenol alkylation to avoid the protection/deprotection steps, gave 73% yield.

Figure 11:
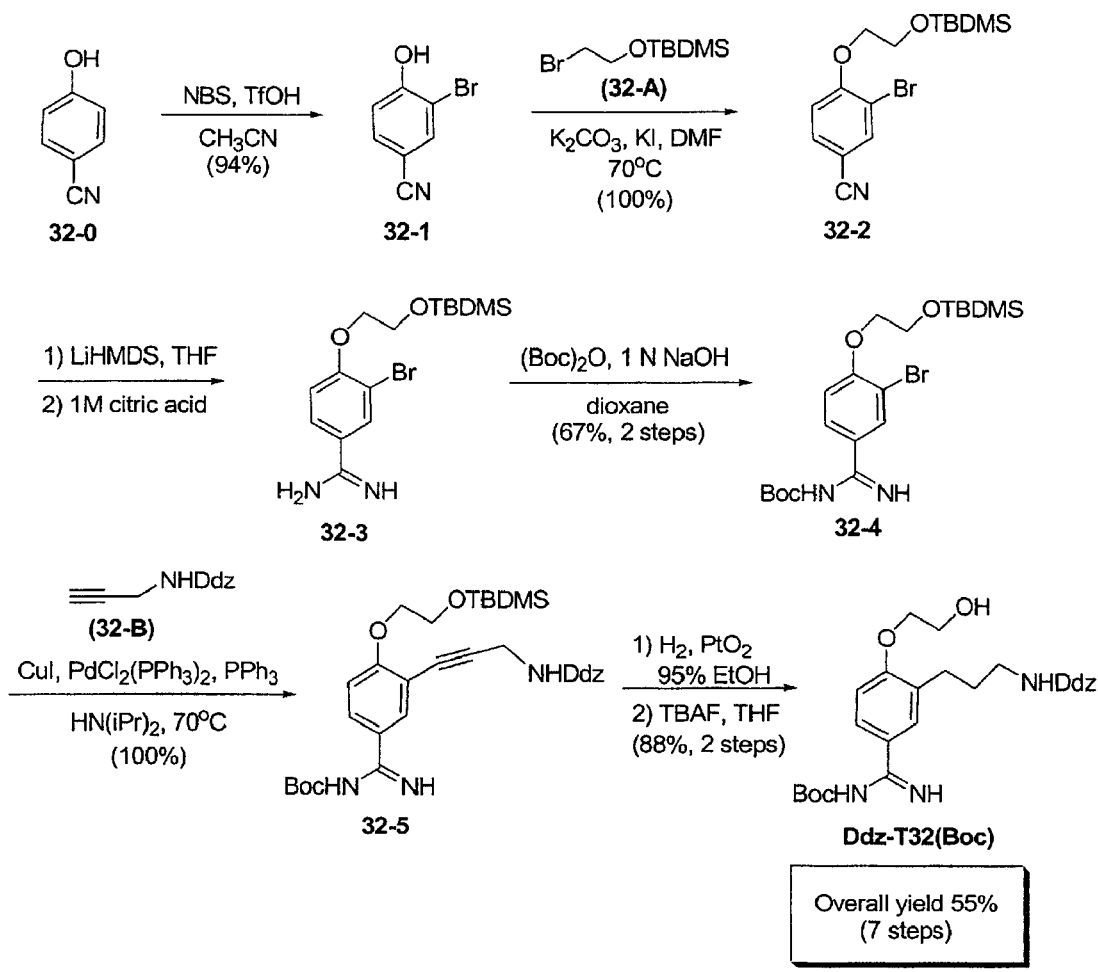
FIG. 11 the standard procedure for the synthesis of tether T32.

A standard procedure for the synthesis of tether T32 is shown in FIG. 11.

Figure 12A:
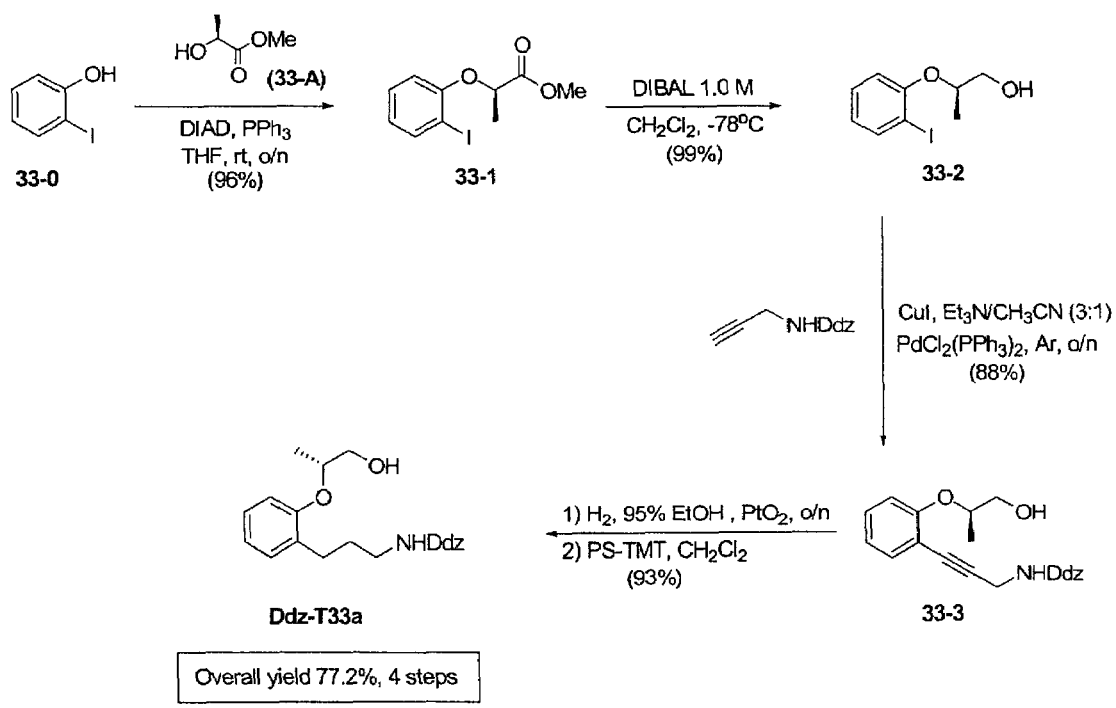
FIGS. 12A, 12B depict the standard procedure for the synthesis of tether T33a and T33b.
Figure 12B:
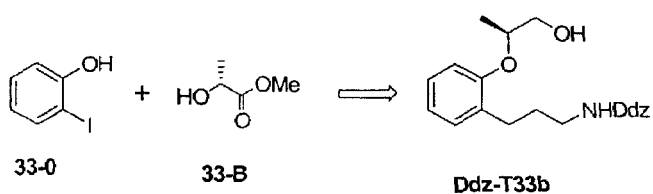

A standard procedure for the synthesis of tether T33a and T33b is shown in FIGS. 12A and 12B.

The construction to the (R)-isomer of this tether (T33a) was accomplished from 2-iodophenol (33-0) and (S)-methyl lactate (33-A). Mitsunobu reaction of 33-0 and 33-A proceeded with inversion of configuration in excellent yield to give 33-1. Reduction of the ester to the corresponding alcohol (33-2) also occurred in high yield and was followed by Sonagashira reaction with Ddz-propargylamine. The alkyne in the resulting coupling product, 33-3, was reduced with catalytic hydrogenation. Workup with scavenger resin provided the desired product, Ddz-T33a.

The synthesis of the (S)-enantiomer (Ddz-T33b) was carried out in an identical manner in comparable yield starting from (R)-methyl lactate (33-B). See FIG. 12B.

Figure 13:
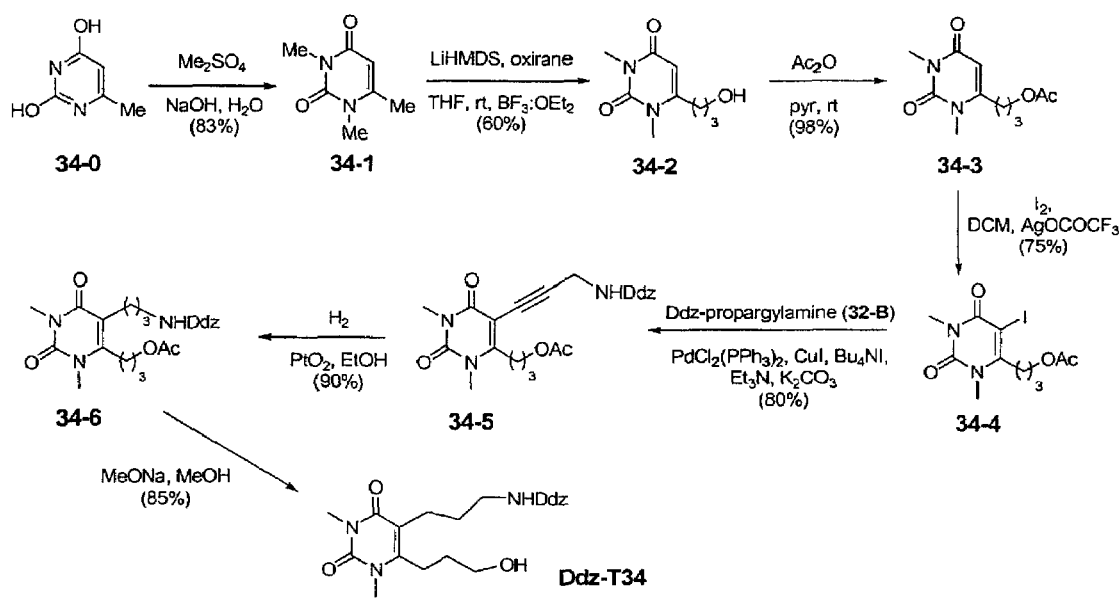
FIG. 13 depicts the standard procedure for the synthesis of tether T34.
Figure 14:
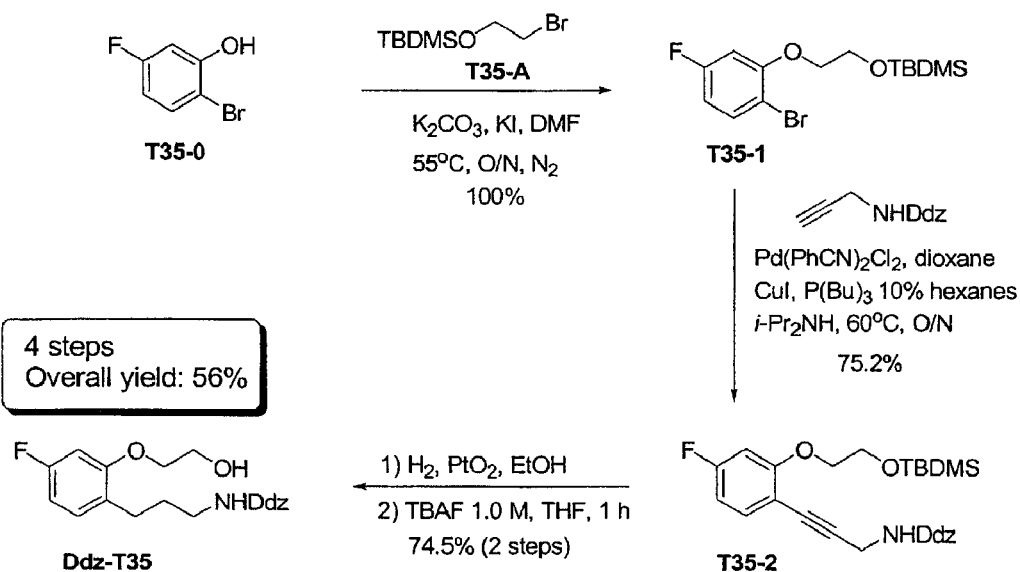
FIG. 14 depicts the standard procedure for the synthesis of tether T35.
Figure 15:
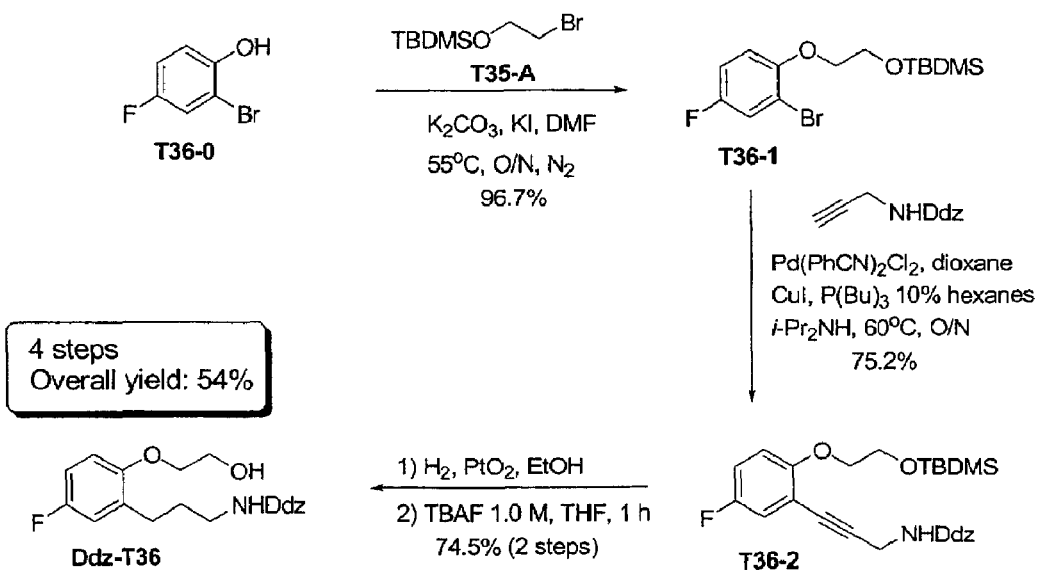
FIG. 15 depicts the standard procedure for the synthesis of tether T36.
Figure 16:
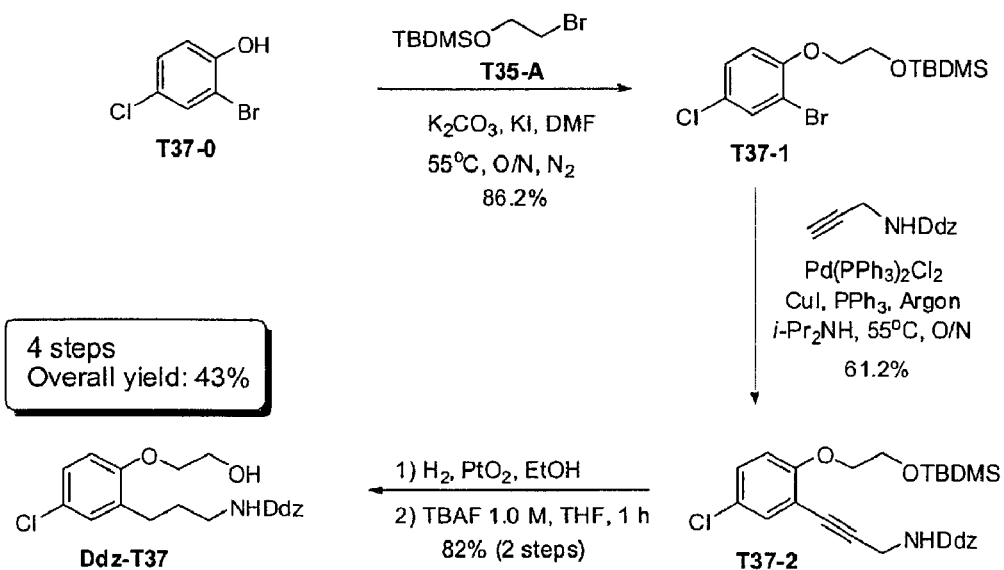
FIG. 16 depicts the standard procedure for the synthesis of tether T37.
Figure 17:
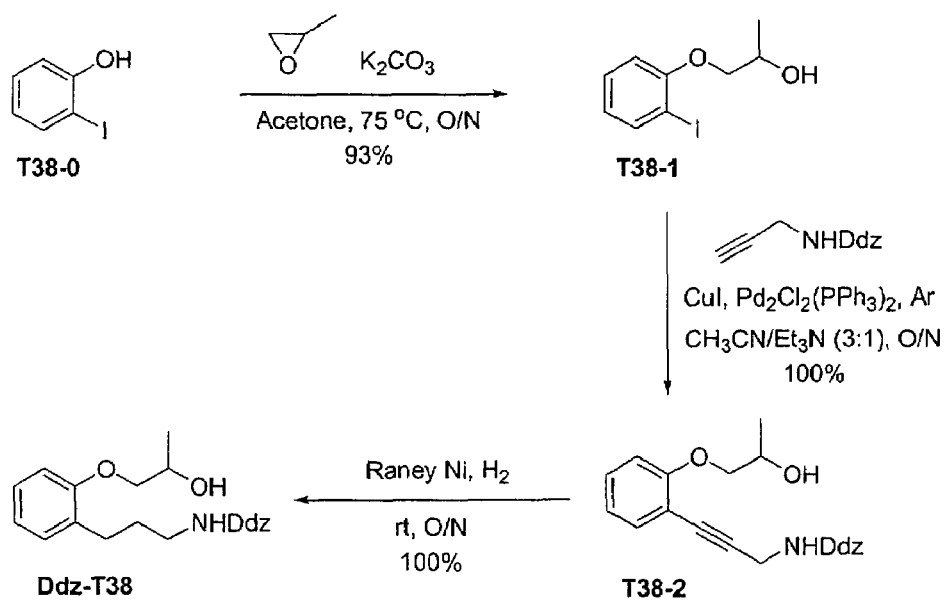
FIG. 17 depicts the standard procedure for the synthesis of tether T38. Chiral T38 can be accessed through the use of asymmetric synthesis methods, resolution or chiral chromatography techniques available in the literature.

Standard procedures for the synthesis of various tethers are shown in the figures: tether T34 (FIG. 13), tether T35 (FIG. 14), tether T36 (FIG. 15), tether T37 (FIG. 16), tether T38 (FIG. 17), tether T39 (FIG. 18), tether T40 (FIG. 19), tether T41 (FIG. 20) and tether T42 (FIG. 21).

E. Examples of Synthetic Strategies for the Macrocyclic Compounds of the Invention FIG. 22 presents a scheme depicting a thioester strategy for macrocyclic compounds of the present invention.

It should be noted that one or more of the amino acids indicated can be replaced by corresponding hydroxy acids and coupled to the next building block utilizing methods known to those in the art.

Example 47

Standard Procedure for Macrocyclization with Thioester Linker

The resin containing the cyclization precursor is combined in an appropriate vessel with pre-washed MP-carbonate resin [Argonaut Technologies, Foster City, Calif., commercially supplied MP-carbonate resin was treated with 3×THF (1 L per 400 g) and dried O/N at 30° C. in a vacuum oven] (1.4 to 1.6 eq relative to the initial loading of the synthesis resin). A 0.2 M DIPEA solution in THF was then added to the combined resins (1 mL/60 mg MP-carbonate resin) and the suspension agitated O/N at rt. Subsequently, the resin was filtered and rinsed 2×THF. The combined filtrates are collected together in an appropriate vessel, then the volatile contents evaporated under reduced pressure [in addition to the standard methods, solvent can also be removed in vacuo using centrifugal evaporation (ThermoSavant Discovery®, Speed-Vac® or comparable) (Thermo Electron Corporation, Waltham, Mass.)] to provide the crude macrocycles.

Example 48

Standard Procedure for Silver-Assisted Macrocyclization with Thioester Linker Except for the cyclization itself and subsequent work-up, this procedure is identical to that of Example 47. The resin containing the cyclization precursor was combined in an appropriate vessel with pre-washed MP-carbonate resin [Argonaut Technologies, commercially supplied MP-carbonate resin was treated with THF (3×, 1 L per 400 g) and dried O/N at 30° C. in a vacuum oven] (1.4 to 1.6 eq relative to the initial loading of the synthesis resin). To this was added THF (1 mL per 100 mg resin) and silver trifluoroacetate (1 eq relative to the initial loading of the resin). Finally, an amount of DIPEA sufficient to obtain a 0.2 M solution was added. The reaction mixture was agitated at rt O/N. The solution was then filtered and the resins washed 2×THF. The filtrates are collected together in an appropriate vessel, then evaporated under reduced pressure [(the volatile contents could also be removed in vacuo using centrifugal evaporation (ThermoSavant Discovery®, SpeedVac® or comparable)] to provide the crude macrocycles. For this procedure, silver trifluoroacetate should be stored in a dessicator between uses. In addition, it is recommended to use a new bottle of THF (or a bottle that has been recently opened under $N_2$ or Ar) to minimize formation of silver oxide.

Additionally, a ring-closing metathesis (RCM) strategy, as developed by Grubbs et al. can also be used to access some of the macrocyclic compounds of the invention (see for example U.S. Pat. No. 5,811,515; Grubbs, R. H. et al. *J. Org. Chem.* 2001, 66,5291-5300; Fürstner, A. Angew. Chem. Int. Ed. 2000, 39, 3012-3043).

To access certain derivatives of compounds of the present invention, additional reactions from those in the general scheme were required. For some, it was advantageous to react the functionality to be derivatized prior to the formation of the macrocyclic ring. The cyclic structure can restrict access of reagents to that functionality. For example, in the synthesis of N-methyl and N-acyl derivatives of macrocycles, where the secondary nitrogen atom of the ring is the site of derivatization, the reaction is preferred to be performed prior to the application of the appropriate cyclization protocol.

In other cases, for example the derivatization of side chain functionality, the reaction was best performed after formation of the macrocyclic ring. For example, further reaction of amino moieties on side chains examples was typically efficiently done by reaction of the partially protected macrocycle. In this manner, acylation, sulfonylation, alkylation (via reductive amination), guanidine and urea formation were performed via standard methods.

Table 1, hereinbelow, shows a representative, but by no means exclusive, summary of the chemical synthesis of several representative compounds of the invention.

TABLE 1

Synthesis of Representative Compounds of the Present Invention

| | $AA_1$ | $AA_2$ | $AA_3$ | Tether | Tether Attachment | Additional Steps |
|---|---|---|---|---|---|---|
| 1 | Bts-D-Tyr(tBu) | Boc-D-Val | Boc-Nva | Ddz-T8 | Example 29 | none |
| 2 | Bts-D-Phe | Boc-D-Val | Boc-Nva | Boc-T8 | Example 29 | none |
| 3 | Bts-D-Phe | Boc-D-Val | Boc-Nva | Boc-T9 | Example 29 | none |
| 4 | Bts-D-Tyr(tBu) | Boc-D-Val | Boc-Nva | Ddz-T9 | Example 29 | none |
| 5 | Bts-D-Tyr(tBu) | Boc-D-Ala | Boc-Nva | Ddz-T8 | Example 29 | none |
| 6 | Bts-D-Tyr(tBu) | Boc-D-Val | Boc-Met | Ddz-T8 | Example 29 | none |
| 7 | Bts-D-Tyr(tBu) | Boc-D-Val | Boc-Nle | Ddz-T8 | Example 29 | none |
| 8 | Bts-D-Tyr(tBu) | Boc-D-Val | Boc-Phe | Ddz-T8 | Example 29 | none |
| 9 | Bts-D-Tyr(tBu) | Boc-D-Val | Boc-Val | Ddz-T8 | Example 29 | none |
| 10 | Bts-D-Tyr(tBu) | Boc-D-Val | Boc-Leu | Ddz-T9 | Example29 | none |
| 11 | Bts-D-2-Nal | Boc-D-Val | Boc-Nva | Boc-T8 | Example 29 | none |
| 12 | Bts-D-Tyr(tBu) | Boc-D-Val | Boc-Abu | Ddz-T8 | Example 29 | none |
| 13 | Bts-D-Phe | Boc-D-Val | Boc-Leu | Boc-T9 | Example 29 | none |
| 14 | Bts-D-2-Nal | Boc-D-Val | Boc-Leu | Boc-T9 | Example 29 | none |
| 15 | Bts-D-Phe(3Cl) | Boc-D-Val | Boc-Nva | Boc-T9 | Example 29 | none |
| 16 | Bts-D-Phe(4Cl) | Boc-D-Val | Boc-Nva | Boc-T9 | Example 29 | none |
| 17 | Bts-D-Trp(Boc) | Boc-D-Val | Boc-Nva | Ddz-T9 | Example 29 | none |
| 18 | Bts-D-Tyr(tBu) | Boc-D-2-Abu | Boc-Nva | Ddz-T9 | Example 29 | none |
| 19 | Bts-D-Phe(4F) | Boc-D-Val | Boc-Nva | Boc-T9 | Example 29 | none |
| 20 | Bts-D-Phe | Boc-D-Val | Boc-Leu | Boc-T8 | Example 29 | none |
| 21 | Bts-D-2-Nal | Boc-D-Val | Boc-Leu | Boc-T8 | Example 29 | none |
| 22 | Bts-D-Tyr(OMe) | Boc-D-Val | Boc-Nva | Boc-T9 | Example 29 | none |
| 23 | Bts-D-1-Nal | Boc-D-Val | Boc-Nva | Boc-T9 | Example 29 | none |
| 24 | Bts-D-2-Thi | Boc-D-Val | Boc-Nva | Boc-T9 | Example 29 | none |
| 25 | Bts-D-Phe(2Cl) | Boc-D-Val | Boc-Nva | Boc-T9 | Example 29 | none |
| 26 | Bts-D-Tyr(tBu) | Boc-D-Val | Boc-Cpa | Ddz-T9 | Example 29 | none |
| 27 | Bts-D-4-Thz | Boc-D-Val | Boc-Nva | Boc-T9 | Example 29 | none |
| 28 | Bts-D-3-Pal | Boc-D-Val | Boc-Nva | Boc-T9 | Example 29 | none |
| 29 | Bts-D-Tyr(tBu) | Boc-D-Val | Ddz-Dap(Boc) | Ddz-T9 | Example 29 | none |
| 30 | Bts-D-Tyr(tBu) | Hnva(THP) | Boc-Nva | Ddz-T9 | Example 29 | none |
| 34 | Bts-D-Tyr(tBu) | Ddz-D-Tyr(tBu) | Boc-Nva | Ddz-T8 | Example 29 | None |

TABLE 1-continued

Synthesis of Representative Compounds of the Present Invention

| | AA₁ | AA₂ | AA₃ | Tether | Tether Attachment | Additional Steps |
|---|---|---|---|---|---|---|
| 38 | Bts-D-Tyr(tBu) | Boc-D-Val | Boc-Ala | Ddz-T8 | Example 29 | none |
| 39 | Bts-D-Tyr(tBu) | Boc-D-Val | Boc-□-Ala | Ddz-T8 | Example 29 | none |
| 40 | Bts-D-Tyr(tBu) | Boc-D-Val | Boc-Gly | Ddz-T8 | Example 29 | none |
| 41 | Bts-D-Tyr(tBu) | Boc-DPhe | Boc-Nva | Ddz-T8 | Example 29 | none |
| 52 | Bts-D-Tyr(tBu) | Boc-D-Val | Boc-Phg | Ddz-T8 | Example 29 | none |
| 55 | Bts-D-Tyr(tBu) | Ddz-D-Val | Ddz-Lys(Boc) | Ddz-T8 | Example 29 | none |
| 56 | Bts-D-Tyr(tBu) | Ddz-D-Val | Ddz-Orn(Boc) | Ddz-T8 | Example 29 | none |
| 57 | Bts-D-Tyr(tBu) | Ddz-D-Val | Ddz-Ser(tBu) | Ddz-T8 | Example 29 | none |
| 58 | Bts-D-Tyr(tBu) | Ddz-D-Val | Ddz-Tyr(tBu) | Ddz-T8 | Example 29 | none |
| 59 | Bts-D-Tyr(tBu) | Ddz--D-Val | Ddz-Trp(Boc) | Ddz-T8 | Example 29 | none |
| 60 | Bts-D-Tyr(tBu) | Boc-D-Val | Boc-Tyr(OMe) | Ddz-T8 | Example 29 | none |
| 65 | Bts-D-Tyr(tBu) | Boc-D-Val | Boc-Nva | Ddz-T2 | Example 29 | none |
| 71 | Bts-D-Tyr(tBu) | Boc-D-Val | Boc-Nva | Ddz-T10 | Example 29 | none |
| 72 | Bts-D-Tyr(tBu) | Boc-D-Val | Boc-2-Nal | Ddz-T8 | Example 29 | none |
| 76 | Bts-D-Tyr(tBu) | Boc-D-2-Nal | Boc-Nva | Ddz-T8 | Example 29 | none |
| 77 | Bts-D-Tyr(tBu) | Boc-D-Nle | Boc-Nva | Ddz-T8 | Example 29 | none |
| 80 | Bts-D-Tyr(tBu) | Boc-D-Val | Boc-Ile | Ddz-T8 | Example 29 | none |
| 85 | Bts-D-Tyr(tBu) | Boc-D-Val | Boc-D-Nva | Ddz-T8 | Example 29 | none |
| 87 | Bts-D-Bip | Boc-D-Val | Boc-Nva | Boc-T9 | Example 29 | none |
| 88 | Bts-D-Tyr(tBu) | Boc-D-Val | Boc-Nva | Ddz-T9 | Example 29 | none |
| 89 | Bts-D-Hfe | Boc-D-Val | Boc-Nva | Boc-T9 | Example 29 | none |
| 90 | Bts-D-Dip | Boc-D-Val | Boc-Nva | Boc-T9 | Example 29 | none |
| 91 | Bts-D-Tyr(tBu) | Boc-D-Nva | Boc-Nva | Ddz-T9 | Example 29 | none |
| 92 | Bts-D-Tyr(tBu) | Boc-D-Tle | Boc-Nva | Ddz-T9 | Example 29 | none |
| 96 | Bts-D-Tyr(tBu) | Boc-β-Ala | Boc-Nva | Ddz-T9 | Example 29 | none |
| 97 | Bts-D-Tyr(tBu) | Boc-D-Chg | Boc-Nva | Ddz-T9 | Example 29 | none |
| 98 | Bts-D-Tyr(tBu) | Boc-D-Val | Boc-Nva | Ddz-T18 | Example 29 | none |
| 99 | Bts-D-Tyr(tBu) | Boc-D-Val | Boc-Nva | Ddz-T15 | Example 29 | none |
| 109 | Bts-D-Tyr(tBu) | Boc-D-Val | Ddz-Dab(Boc) | Ddz-T9 | Example 29 | none |
| 110 | Bts-D-Tyr(tBu) | Boc-D-Val | Boc-Nva | Ddz-T11 | Example 29 | none |
| 111 | Bts-D-Tyr(tBu) | Boc-D-Val | Hval(THP) | Ddz-T9 | Example 29 | none |
| 112 | Bts-D-Tyr(tBu) | Boc-D-Val | Boc-Nva | Ddz-T9 | Example 29 | none |
| 120 | Bts-D-Tyr(tBu) | Boc-D-Pro | Boc-Nva | Ddz-T8 | Example 29 | none |
| 121 | Bts-D-Tyr(tBu) | Boc-D-Val | Boc-Nva | Ac-T8-NH2 | Example 29 | none |
| 122 | Boc-D-3-Pal | Boc-D-Val | Boc-Nva | Boc-T9 | Example 30 | none |
| 123 | Boc-D-2-Pal | Boc-D-Val | Boc-Nva | Boc-T9 | Example 30 | none |
| 124 | Boc-D-4-Pal | Boc-D-Val | Boc-Nva | Boc-T9 | Example 30 | none |

TABLE 1-continued

Synthesis of Representative Compounds of the Present Invention

| | AA₁ | AA₂ | AA₃ | Tether | Tether Attachment | Additional Steps |
|---|---|---|---|---|---|---|
| 125 | Bts-D-Tyr(tBu) | Boc-D-Cpg | Boc-Nva | Boc-T9 | Example 29 | none |
| 126 | Bts-D-Tyr(tBu) | Boc-D-Val | Boc-NMeLeu | Boc-T9 | Example 29 | none |
| 127 | Boc-D-His(Mts) | Boc-D-Val | Boc-Nva | Boc-T12 | Example 30 | none |
| 128 | Bts-D-Tyr(OMe) | Boc-D-Val | Boc-Leu | Boc-T9 | Example 29 | none |
| 129 | Bts-D-1-Nal | Boc-D-Val | Boc-Leu | Boc-T9 | Example 29 | none |
| 130 | Bts-D-2-Thi | Boc-D-Val | Boc-Leu | Boc-T9 | Example 29 | none |
| 131 | Bts-D-Phe(3Cl) | Boc-D-Val | Boc-Leu | Boc-T9 | Example 29 | none |
| 132 | Bts-D-Phe(4Cl) | Boc-D-Val | Boc-Leu | Boc-T9 | Example 29 | none |
| 133 | Bts-D-Phe(4F) | Boc-D-Val | Boc-Leu | Boc-T9 | Example 29 | none |
| 134 | Bts-D-Phe(3Cl) | Boc-D-Val | Boc-Leu | Boc-T2 | Example 29 | none |
| 135 | Bts-D-Tyr(OMe) | Boc-D-Val | Boc-Leu | Boc-T11 | Example 29 | none |
| 136 | Bts-D-1Nal | Boc-D-Val | Boc-Leu | Boc-T11 | Example 29 | none |
| 137 | Bts-D-2-Thi | Boc-D-Val | Boc-Leu | Boc-T11 | Example 29 | none |
| 138 | Bts-D-Phe(3Cl) | Boc-D-Val | Boc-Leu | Boc-T11 | Example 29 | none |
| 139 | Bts-D-Phe(4Cl) | Boc-D-Val | Boc-Leu | Boc-T11 | Example 29 | none |
| 140 | Bts-D-Phe(4F) | Boc-D-Val | Boc-Leu | Boc-T11 | Example 29 | none |
| 141 | Bts-D-Tyr(OMe) | Boc-D-Val | Boc-Cpa | Boc-T9 | Example 29 | none |
| 142 | Bts-D-1-Nal | Boc-D-Val | Boc-Cpa | Boc-T9 | Example 29 | none |
| 143 | Bts-D-2-Thi | Boc-D-Val | Boc-Cpa | Boc-T9 | Example 29 | none |
| 144 | Bts-D-Phe(3Cl) | Boc-D-Val | Boc-Cpa | Boc-T9 | Example 29 | none |
| 145 | Bts-D-Phe(4Cl) | Boc-D-Val | Boc-Cpa | Boc-T9 | Example 29 | none |
| 146 | Bts-D-Phe(4F) | Boc-D-Val | Boc-Cpa | Boc-T9 | Example 29 | none |
| 147 | Bts-D-Tyr(OMe) | Boc-D-Val | Boc-Cpa | Boc-T11 | Example 29 | none |
| 148 | Bts-D-1-Nal | Boc-D-Val | Boc-Cpa | Boc-T11 | Example 29 | none |
| 149 | Bts-D-Phe(3Cl) | Boc-D-Val | Boc-Cpa | Boc-T11 | Example 29 | none |
| 150 | Bts-D-Phe(4Cl) | Boc-D-Val | Boc-Cpa | Boc-T11 | Example 29 | none |
| 151 | Bts-D-Phe(4F) | Boc-D-Val | Boc-Cpa | Boc-T11 | Example 29 | none |
| 152 | Bts-D-Tyr(OMe) | Ddz-D-Val | Ddz-Dap(Boc) | Ddz-T9 | Example 29 | none |
| 153 | Bts-D-1-Nal | Ddz-D-Val | Ddz-Dap(Boc) | Ddz-T9 | Example 29 | none |
| 154 | Bts-D-2-Thi | Ddz-D-Val | Ddz-Dap(Boc) | Ddz-T9 | Example 29 | none |
| 155 | Bts-D-Phe(3Cl) | Ddz-D-Val | Ddz-Dap(Boc) | Ddz-T9 | Example 29 | none |
| 156 | Bts-D-Phe(4Cl) | Ddz-D-Val | Ddz-Dap(Boc) | Ddz-T9 | Example 29 | none |
| 157 | Bts-D-Phe(4F) | Ddz-D-Val | Ddz-Dap(Boc) | Ddz-T9 | Example 29 | none |
| 158 | Bts-D-Phe(3Cl) | Ddz-D-Val | Ddz-Dap(Boc) | Ddz-T11 | Example 29 | none |
| 159 | Bts-D-Tyr(But) | Boc-D-Ile | Boc-Nva | Boc-T9 | Example 29 | none |
| 160 | Bts-D-Tyr(But) | Boc-D-alloIle | Boc-Nva | Boc-T9 | Example 29 | none |

TABLE 1-continued

Synthesis of Representative Compounds of the Present Invention

| | AA₁ | AA₂ | AA₃ | Tether | Tether Attachment | Additional Steps |
|---|---|---|---|---|---|---|
| 161 | Boc-D-Phe(4CH2NHFmoc) | Boc-D-Val | Boc-Nva | Boc-T9 | Example 30 | none |
| 162 | Bts-D-Phe(2Me) | Boc-D-Val | Boc-Nva | Boc-T9 | Example 29 | none |
| 163 | Bts-D-Phe(3Me) | Boc-D-Val | Boc-Nva | Boc-T9 | Example 29 | none |
| 164 | Bts-D-Phe(4Me) | Boc-D-Val | Boc-Nva | Boc-T9 | Example 29 | none |
| 165 | Bts-D-Phe(3OMe) | Boc-D-Val | Boc-Nva | Boc-T9 | Example 29 | none |
| 166 | Bts-D-Phe(2OMe) | Boc-D-Val | Boc-Nva | Boc-T9 | Example 29 | none |
| 167 | Bts-D-3-benzothienyl | Boc-D-Val | Boc-Nva | Boc-T9 | Example 29 | none |
| 168 | Bts-D-3-Thi | Boc-D-Val | Boc-Nva | Boc-T9 | Example 29 | none |
| 169 | Bts-D-□-HomoPhe(3Cl) | Boc-D-Val | Boc-Nva | Boc-T9 | Example 29 | none |
| 170 | Bts-D-Phe(3,4diCl) | Boc-D-Val | Boc-Nva | Boc-T9 | Example 29 | none |
| 171 | Bts-D-Phe(3,4diF) | Boc-D-Val | Boc-Nva | Boc-T9 | Example 29 | none |
| 172 | Bts-D-Phe(3,4diOMe) | Boc-D-Val | Boc-Nva | Boc-T9 | Example 29 | none |
| 173 | Bts-D-1Nal | Hnva(THP) | Boc-Nva | Boc-T9 | Example 29 | none |
| 174 | Bts-D-Tyr(OMe) | Hnva(THP) | Boc-Nva | Boc-T9 | Example 29 | none |
| 175 | Bts-D-Tyr(tBu) | Boc-D-Val | Boc-Nva | Boc-T33b | Example 29 | none |
| 176 | Bts-D-Tyr(tBu) | Boc-D-Val | Boc-Nva | Boc-T33a | Example 29 | none |
| 177 | Bts-D-Tyr(tBu) | Boc-D-Val | Boc-Nva | Boc-T28 | Example 29 | none |
| 178 | Bts-D-Tyr(OMe) | Ddz-D-Val | Ddz-Ser(tBu) | Ddz-T9 | Example 29 | none |
| 179 | Bts-D-1-Nal | Ddz-D-Val | Ddz-Ser(tBu) | Ddz-T9 | Example 29 | none |
| 180 | Bts-D-2-Thi | Ddz-D-Val | Ddz-Ser(tBu) | Ddz-T9 | Example 29 | none |
| 181 | Bts-D-Phe(3Cl) | Ddz-D-Val | Ddz-Ser(tBu) | Ddz-T9 | Example 29 | none |
| 182 | Bts-D-Phe(4Cl) | Ddz-D-Val | Ddz-Ser(tBu) | Ddz-T9 | Example 29 | none |
| 183 | Bts-D-Phe(4F) | Ddz-D-Val | Ddz-Ser(tBu) | Ddz-T9 | Example 29 | none |
| 184 | Bts-D-1-Nal | Ddz-D-Val | Ddz-Dap(Boc) | Ddz-T11 | Example 29 | none |
| 185 | Bts-D-Phe(4Cl) | Ddz-D-Val | Ddz-Dap(Boc) | Ddz-T11 | Example 29 | none |
| 186 | Ddz-D-Tyr(tBu) | Ddz-D-Val | Ddz-His(Mts) | Ddz-T9 | Example 30 | none |
| 187 | Bts-D-Phe(3CF3) | Boc-D-Val | Boc-Nva | Boc-T9 | Example 29 | none |
| 188 | Bts-D-Phe(3F) | Boc-D-Val | Boc-Nva | Boc-T9 | Example 29 | none |
| 189 | Bts-D-Phe(4NO2) | Boc-D-Val | Boc-Nva | Boc-T9 | Example 29 | none |
| 190 | Bts-D-3-benzothienyl | Boc-D-Val | Boc-Cpa | Boc-T9 | Example 29 | none |
| 191 | Bts-D-Phe(3OMe) | Boc-D-Val | Boc-Cpa | Boc-T9 | Example 29 | none |
| 192 | Bts-D-Phe(3,4diCl) | Boc-D-Val | Boc-Cpa | Boc-T9 | Example 29 | none |

TABLE 1-continued

Synthesis of Representative Compounds of the Present Invention

| | AA₁ | AA₂ | AA₃ | Tether | Tether Attachment | Additional Steps |
|---|---|---|---|---|---|---|
| 193 | Bts-D-Phe(3,4diF) | Boc-D-Val | Boc-Cpa | Boc-T9 | Example 29 | none |
| 194 | Bts-D-Tyr(OMe) | Boc-D-Val | Boc-Nva | Boc-T34 | Example 29 | none |
| 195 | Bts-D-Tyr(OMe) | Boc-D-Val | Boc-Nva | Boc-T38 | Example 29 | none |
| 196 | Bts-D-Phe(3Cl) | Boc-D-Val | Boc-Cpa | Ddz-T32(Boc) | Example 29 | none |
| 197 | Bts-D-Phe(3Cl) | Boc-D-Val | Boc-Cpa | Boc-T34 | Example 29 | none |
| 198 | Bts-D-Phe(3Cl) | Boc-D-Val | Boc-Cpa | Boc-T38 | Example 29 | none |
| 199 | Bts-D-Phe(3Cl) | Boc-D-Val | Boc-Cpa | Boc-T41 | Example 29 | none |
| 200 | Bts-D-Phe(3Cl) | Boc-D-Val | Boc-Cpa | Boc-T8 | Example 29 | none |
| 201 | Bts-D-1-Nal | Boc-D-Val | Boc-Nva | Boc-T8 | Example 29 | none |
| 202 | Bts-D-Phe(3OMe) | Boc-D-Val | Boc-Nva | Boc-T8 | Example 29 | none |
| 203 | Bts-D-Phe(4Cl) | Ddz-D-Val | Ddz-Dap(Boc) | Ddz-T9 | Example 29 | acetylation |
| 204 | Bts-D-Phe(4Cl) | Ddz-D-Val | Ddz-Dap(Boc) | Ddz-T9 | Example 29 | guanidinylation |
| 205 | Bts-D-Phe(3Cl) | Boc-D-Val | Boc-NMeLeu | Boc-T9 | Example 29 | none |
| 206 | Bts-D-Phe(4Cl) | Ddz-D-Val | Ddz-Dap(Boc) | Ddz-T9 | Example 29 | mesylation |
| 207 | Bts-D-Phe(4Cl) | Ddz-D-Val | Ddz-Dap(Boc) | Ddz-T9 | Example 29 | TMS-isocyanate followed by dilute acid |
| 208 | Bts-D-Tyr(tBu) | Ddz-D-Val | Ddz-Dap(Boc) | Ddz-T9 | Example 29 | guanidinylation |
| 209 | Bts-D-Tyr(tBu) | Ddz-D-Val | Ddz-Dap(Boc) | Ddz-T9 | Example 29 | acetylation |
| 210 | Bts-D-Tyr(tBu) | Ddz-D-Val | Ddz-Dap(Boc) | Ddz-T9 | Example 29 | reductive amination with acetone |
| 211 | Bts-D-Phe(4Cl) | Ddz-D-Val | Ddz-Dap(Boc) | Ddz-T9 | Example 29 | reductive amination with excess formaldehyde |
| 212 | Bts-D-Phe(4Cl) | Ddz-D-Val | Ddz-Dap(Boc) | Ddz-T9 | Example 29 | reductive amination with acetone |
| 213 | Bts-D-Tyr(3,5diI) | Boc-D-Val | Boc-Nva | Boc-T9 | Example 29 | none |
| 214 | Bts-D-Tyr(OMe) | Boc-D-Val | Boc-Hse(Bzl) | Boc-T9 | Example 29 | hydrogenolysis for protecting group removal |
| 215 | Bts-D-Tyr(tBu) | Ddz-D-Val | Ddz-Dap(Boc) | Ddz-T9 | Example 29 | reductive amination with excess formaldehyde |
| 216 | Bts-D-Phe(3Cl) | Boc-D-Val | Boc-Cpa | Boc-T40 | Example 29 | none |
| 217 | Bts-D-Phe(3Cl) | Boc-D-Val | Boc-Cpa | Boc-T36 | Example 29 | none |
| 218 | Bts-D-Phe(3Cl) | Boc-D-Val | Boc-Nva | Boc-T39 | Example 29 | none |
| 219 | Bts-D-Phe(3Cl) | Boc-D-Val | Boc-Nva | Boc-T37 | Example 29 | none |
| 220 | Bts-D-Phe(3Cl) | Boc-D-Val | Boc-Nva | Boc-T39 | Example 29 | none |
| 221 | Bts-D-Phe(3Cl) | Boc-D-Val | Boc-Nva | Boc-T35 | Example 29 | none |
| 222 | Bts-D-Tyr(3tBu) | Boc-D-Val | Boc-Nva | Boc-T9 | Example 29 | none |
| 223 | Bts-D-Tyr(But) | Boc-D-Val | Boc-Nva | Boc-T9 | Example 29 | acetylation |

TABLE 1-continued

Synthesis of Representative Compounds of the Present Invention

| | AA₁ | AA₂ | AA₃ | Tether | Tether Attachment | Additional Steps |
|---|---|---|---|---|---|---|
| 224 | Bts-D-1-Nal | Boc-D-Val | Boc-Leu | Boc-T9 | Example 29 | reductive amination with formaldehyde |
| 225 | Bts-D-1-Nal | Boc-D-Val | Boc-Leu | Boc-T9 | Example 29 | acetylation |
| 226 | Bts-D-1-Nal | Boc-D-Val | Boc-Leu | Boc-T9 | Example 29 | reductive amination with aldehyde |
| 227 | Bts-D-1-Nal | Boc-D-Val | Boc-Leu | Boc-T9 | Example 29 | reductive amination with benzaldehyde |

Notes
Any amino acid or tether designated as the Boc derivative could be substituted with the corresponding Ddz derivative.

D. Analytical Data for Selected Compounds of the Invention $^1$H and $^{13}$C NMR spectra were recorded on a Varian Mercury 300 MHz spectrometer (Varian, Inc., Palo Alto, Calif.) and are referenced internally with respect to the residual proton signals of the solvent. Information about the conformation of the molecules in solution can be determined utilizing appropriate two-dimensional NMR techniques known to those skilled in the art. HPLC purifications were run on a Waters Xterra® MS C18 column, using the Waters FractionLynx® system (Waters Corporation, Milford, Mass.). Automated medium pressure chromatographic purifications were performed on an Isco CombiFlash® 16× system with disposable silica or C18 cartridges that permitted up to sixteen (16) samples to be run simultaneously (Teledyne Isco, Inc., Lincoln, Nebr.). MS spectra were recorded on a Waters Micromass®) Platform II or ZQ™ system. HRMS spectra were recorded with a VG Micromass ZAB-ZF spectrometer. Chemical and biological information were stored and analyzed utilizing the ActivityBase® database software (ID Business Solutions Ltd., Guildford, Surrey, UK).

General Methods for Analytical HPLC Analyses

HPLC analyses are performed on a Waters Alliance® system 2695 running at 1 mL/min using an Xterra MS C18 column 4.6×50 mm (3.5 μm). A Waters 996 PDA provided UV data for purity assessment (Waters Corporation, Milford, Mass.). An LCPackings (Dionex Corporation, Sunnyvale, Calif.) splitter (50:40:10) allowed the flow to be separated in three parts. The first part (50%) went to a Micromass® Platform II MS equipped with an APCI probe for identity confirmation. The second part (40%) went to an evaporative light scattering detector (ELSD, Polymer Laboratories, now part of Varian, Inc., Palo Alto, Calif., PL-ELS-1000™) for purity assessment and the last portion (10%) to a chemiluminescence nitrogen detector (CLND, Antek® Model 8060, Antek Instruments, Houston, Tex., part of Roper Industries, Inc., Duluth, Ga.) for quantitation and purity assessment. Data was captured and processed utilizing the most recent version of the Waters Millenium® software package (Milford, Mass.).

An example LC method suitable for compounds of the present invention uses MeOH as solvent A, H₂O as solvent B and 1% TFA/H₂O as solvent D. Initial mobile-phase composition is 5% A, 85% B and 10% D. Details of the standard gradient method are shown below:

| Time | A % | B % | D % | Curve |
|---|---|---|---|---|
| 0.00 | 5 | 85 | 10 | 6 |
| 1.00 | 5 | 85 | 10 | 6 |
| 6.00 | 50 | 40 | 10 | 6 |
| 9.00 | 50 | 40 | 10 | 6 |
| 14.00 | 90 | 0 | 10 | 6 |
| 17.00 | 90 | 0 | 10 | 6 |
| 17.50 | 5 | 85 | 10 | 6 |
| 20.00 | 5 | 85 | 10 | 6 |

Compounds 2-6, 8-10, 56, 65 and 144 are as defined in Table (3), hereinbelow.

Compound 2

Yield: 12 mg pure macrocycle was obtained (CLND quantification).

$^1$H NMR (300 MHz, DMSO-d$_6$) δ 8.83 (m, 1H); 8.53 (m, 1H); 7.63 (m, 1H); 7.4-7.08 (m, 7H); 7.00-6.84 (m, 2H); 6.60 (d, 15 Hz, 1H); 6.41 (dt, 15 Hz, 5.4 Hz, 1H); 4.35 (m, 1H); 4.25-4.05 (m, 3H); 3.94 (dt, 1H, 6 Hz, 15 Hz); 3.79 (dd, 1H, 3.6 Hz, 8.4 Hz); 3.60 (m, 1H); 3.52-3.40 (bd, 1H); 3.22-3.06 (m, 4H); 1.88 (m, 2H); 1.54-1.28 (m, 2H); 1.25 (d, 3H, 4.8 Hz); 1.22 (d, 3H, 2.7 Hz); 0.92-0.80 (m, 6H).

HRMS calc. for $C_{30}H_{40}N_4O_4$: 520.3049; found 520.3057±0.0016

HPLC [standard gradient method (refers to that presented in General Methods for Analytical HPLC Analyses)] $t_R$=9.55 min.

Compound 4

Yield: 12 mg pure macrocycle was obtained (CLND quantification).

$^1$H NMR (300 MHz, DMSO-d$_6$) δ 9.35 (b, 1H); 8.98 (b, 1H); 5.52 (d, 1H, 8.4 Hz); 8.38 (b, 1H); 7.25 (b, 1H); 7.13-7.07 (m, 4H); 6.86 (t, 2H, 7.5 Hz); 6.57 (d, 2H, 8.7 Hz); 4.33 (b, 1H); 4.21-4.02 (m, 3H); 3.78 (dd, 1H, 3.3 Hz; 8.1 Hz); 3.65-3.54 (m, 1H); 3.31-3.23 (m, 1H); 3.13-3.02 (m, 4H); 2.78-2.2.28-2.18 (m, 1H); 2.0-1.80 (m, 2H); 1.50-1.30 (m, 3H); 1.25 (d, 3H, 4.5 Hz); 1.22 (d, 3H, 4.5 Hz); 1.01 (d, 3H, 6.6 Hz); 0.90 (d, 3H, 6.6 Hz); (t, 3H, 7.5 Hz).

$^{13}$C NMR (75.5 MHz, DMSO-d$_6$) δ 172.22; 171.37; 157.77; 157.44; 156.04; 131.76; 130.80; 130.70; 127.88;

121.82; 115.83; 111.71; 62.13; 60.62; 54.21; 52.81; 47.13; 42.47; 33.31; 29.69; 29.30; 28.61; 20.36; 19.44; 18.72; 17.60; 13.97.

HRMS calc. for $C_{30}H_{42}N_4O_5$: 538.3155; found: 538.3145±0.0016

HPLC (standard gradient) $t_R$=8.12 min.

Compound 5

Yield: 17 mg pure macrocycle was obtained (CLND quantification).

$^1$H NMR (300 MHz, DMSO-$d_6$) δ 9.02 (b, 1H); 8.47 (d, 1H, 8.4 Hz); 7.7 (b, 1H); 7.58 (d, 1H, 5.4 Hz); 7.28 (dd, 1H, 7.8 Hz, 0.8 Hz); 7.20 (t, 1H, 9.0 Hz, 0.8 Hz); 7.14 (d, 2H, 8.4 Hz); 6.98-6.91 (m, 3H); 6.66 (d, 8.7 Hz); 6.63 (d, 1H, 15.0 Hz); 6.43 (dt, 1H, 6.0 Hz, 15.0 Hz); 4.28-3.86 (m, 6H); 3.60-3.40 (m, 2H); 3.22-3.12 (m, 1HO); 3.05 (d, 2H, 5.4 Hz); 1.92-1.80 (m, 1H); 1.56-1.40 (m, 1H); 1.36-1.20 (m, 2H); 1.25 (d, 3H, 6.6 Hz); 0.84 (t, 3H, 7.2 Hz).

$^{13}$C NMR (75.5 MHz, DMSO-$d_6$) δ 172.54; 171.86; 158.97; 158.56; 127.39; 155.84; 131.62; 129.73; 129.20; 129.02; 128.43; 126.30; 124.51; 122.01; 115.85; 112.88; 61.23; 52.90; 51.23; 47.08; 42.66; 36.13; 33.30; 21.14; 19.57; 17.07; 14.14; 11.49.

HRMS calc. for $C_{28}H_{36}N_4O_5$: 508.2685; found: 508.2681±0.0015

HPLC (standard gradient) $t_R$=7.67 min.

Compound 6

Yield: 16 mg pure macrocycle was obtained (CLND quantification).

$^1$H NMR (300 MHz, DMSO-$d_6$) δ 9.37 (b, 1H); 8.87 (b, 1H); 8.61 (d, 1H, 8.7 Hz); 7.62 (b, 1H); 7.27 (d, 1H, 7.8 Hz); 7.21 (t, 1H, 8.4 Hz); 7.14 (d, 2H, 8.4 Hz); 6.98-6.87 (m, 3H); 6.64 (d, 2H, 8.1 Hz); 6.70 (d, 1H, 15.6 Hz); 6.39 (dt, 1H, 6.3 Hz, 15.6 Hz); 4.44-4.36 (m, 1H); 4.34-4.08 (m, 2 Hz); 4.45-3.92 (dt, 1H, 6.9 Hz, 15.6 Hz); 3.74 (dd, 1H, 3.6 Hz, 8.4 Hz); 3.54-3.26 (m, 3H); 3.22-3.02 (m, 3H); 2.60-2.36 (m, 4H); 2.24-2.14 (m, 1H); 2.02 (s, 3H); 1.96-1.89 (m, 1H); 1.80-1.66 (m, 1H); 1.01 (d, 3H, 6.3 Hz); 0.90 (d, 3H, 6.6 Hz).

$^{13}$C NMR (75.5 MHz, DMSO-$d_6$) δ 171.51; 171.26; 158.90; 158.49; 157.38; 155.86; 131.63; 129.82; 129.21; 128.86; 128.63; 126.21; 121.98; 115.83; 112.83; 62.11; 61.06; 51.97; 47.10; 42.78; 30.91; 30.67; 29.34; 20.37; 19.39; 15.06.

HRMS calc. for $C_{30}H_{40}N_4O_5S$: 568.2719; found: 568.2711±0.0017

HPLC $R_t$ (general method) 7.92 min.

Compound 8

Yield: 27 mg pure macrocycle was obtained (CLND quantification).

$^1$H NMR (300 MHz, DMSO-$d_6$) δ 9.05 (b, 1H); 8.43 (b, 1H); 8.34 (d, 1H, 9.3 Hz); 7.40 (b, 1H); 6.97 (d, 1H, 7.5 Hz); 6.92-6.74 (m, 9H); 6.67-6.54 (m, 2H); 6.33-6.25 (m, 3H); 6.10 (dt, 1H, 5.7 Hz, 16.2 Hz); 4.22 (dt, 1H, 0.9 Hz, 12 Hz); 3.94-6.66 (m, 4H); 3.30 (dd, 1H, 3.6 Hz, 7.8 Hz); 3.24 (m, 1H); 3.18 (m, 1H); 2.85-2.68 (m, 3H); 2.44-2.23 (m, 2H); 1.32 (o, 1H, 7.5 Hz); 0.97-0.89 (m, 2H); 0.42 (d, 3H, 6.6 Hz); 0.01 (d, 3H, 6.6 Hz).

$^{13}$C NMR (75.5 MHz, DMSO-$d_6$) δ 171.20; 157.35; 155.88; 139.12; 131.61; 130.87; 129.74; 129.21; 128.77; 128.88; 126.85; 126.19; 121.97; 115.82; 112.84; 62.04; 61.10; 55.07; 50.01; 47.09; 42.85; 37.42; 29.11.

HRMS calc. For $C_{34}H_{42}N_4O_5$: 586.3155; found: 586.3145±0.0017

HPLC $R_t$ (general method) 9.34 min.

Compound 9

Yield: 17 mg pure macrocycle was obtained (CLND quantification).

$^1$H NMR (300 MHz, DMSO-$d_6$) δ 9.39 (b, 1H); 8.83 (b, 1H); 8.29 (d, 1H, 9.3 Hz); 7.62 (b, 1H); 7.28 (d, 1H, 6.6 Hz); 7.20 (t, 1H, 6.9 Hz); 7.12 (d, 2H, 7.8 Hz); 6.98-6.91 (m, 2H); 6.63 (d, 2H, 8.4 Hz); 6.58 (d, 1H, 16.2 Hz); 6.40 (dt, 1H, 5.7 Hz, 16.2 Hz); 4.29-4.13 (m, 3H); 4.03-3.92 (m, 2H); 3.52 (m, 1H); 3.15-3.05 (m, 3H); 2.45-2.37 (m, 1H); 1.96-1.88 (m, 1H); 1.25 (dd, 2H, 4.5 Hz; 6 Hz); 1.01 (d, 3H, 6.3 Hz); 0.91 (d, 3H, 6.6 Hz); 0.86 (d, 3H, 7.2 Hz); 0.81 (d, 3H, 6.6 Hz).

$^{13}$C NMR (75.5 MHz, DMSO-$d_6$) δ 171.85; 171.17; 157.37; 155.87; 131.59; 129.88; 129.18; 128.97; 128.78; 128.51; 126.16; 121.97; 115.83; 112.85; 61.55; 61.18; 58.15; 54.22; 47.08; 42.89; 36.32; 29.35; 29.00; 20.34; 19.56; 18.73; 17.44.

HRMS calc. for $C_{30}H_{40}N_4O_5$ 536.2998; found: 536.2990±0.0017.

HPLC (standard gradient) $t_R$=8.15 min.

Compound 10

Yield: 24 mg pure macrocycle was obtained (CLND quantification).

$^1$H NMR (300 MHz, DMSO-$d_6$) δ 9.33 (b, 1H); 8.82 (b, 1H); 8.56 (d, 1H, 8.3 Hz); 7.60 (b, 1H); 7.27 (d, 2H, 7.8 Hz); 7.20 (t, 1H, 7.8 Hz); 7.13 (d, 2H, 8.4 Hz); 6.95 (t, 2H, 7.8 Hz); 6.64 (d, 2H, 8.4 Hz); 6.57 (d, 1H, 15.4 Hz); 6.38 (dt, 1H, 15.4 Hz, 5.8 Hz); 4.26-4.10 (m, 3H); 3.96 (dt, 1H, 5.4 Hz, 8.4 Hz); 3.77 (dd, 1H, 3.7 Hz, 7.8 Hz); 3.51-3.24 (m, 3H); 3.18-3.02 (m, 3H); 1.90 (h, 1H, 6.4 Hz); 1.73-1.54 (m, 2H); 1.45 (dt, 1H, 6.7 Hz, 0.9 Hz); 0.99 (d, 3H, 6.6 Hz); 0.89 (d, 3H, 6.3 Hz); 0.87 (d, 3H, 6.0 Hz); 0.80 (d, 3H, 6.3 Hz).

$^{13}$C NMR (75.5 MHz, DMSO-$d_6$) δ 172.23; 171.17; 157.37; 155.88; 131.62; 129.82; 129.19; 128.95; 128.59; 126.24; 121.99; 115.84; 112.88; 64.23; 61.98; 61.14; 51.43; 61.14; 51.43; 47.07; 42.81; 29.38; 24.85; 24.11; 21.00; 20.32; 19.30.

HRMS calc. for $C_{31}H_{42}N_4O_5$ 550.3155; found: 550.3150±0.0016.

HPLC (standard gradient) $t_R$=8.91 min.

Compound 56

Yield: 16 mg pure macrocycle was obtained (CLND quantification).

$^1$H NMR (300 MHz, DMSO-$d_6$) δ 9.39 (b, 1H); 8.90 (b, 1H); 8.67 (d, 1H, 8.4 Hz); 7.74 (b, 4H); 7.29-7.08 (m, 4H); 6.99-6.87 (m, 2H); 6.64 (d, 2H, 8.1 Hz); 6.61 (d, 1H, 16.5 Hz); 6.40 (dt, 1H, 5.7 Hz, 16.5 Hz); 4.40-4.06 (m, 4H); 4.02-3.95 (m, 1H); 3.79 (dd, 1H, 3.6 Hz, 7.8 Hz); 3.55-3.30 (m, 2H); 3.16-3.05 (m, 3H); 2.82-2.69 (m, 2H); 2.02-1.85 (m, 2H); 1.64-1.43 (m, 3H); 1.29-1.23 (m, 1H); 1.01 (d, 3H, 6.3 Hz); 0.91 (d, 3H, 6.3 Hz); 0.86-0.84 (m, 2H).

HPLC (standard gradient) $t_R$=5.71 min.

Compound 65

Yield: 17 mg pure macrocycle was obtained (CLND quantification).

$^1$H NMR (300 MHz, DMSO-$d_6$) δ 9.60 (b, 1H); 9.39 (b, 1H); 8.88 (b, 1H); 8.70 (d, 1H, 7.5 Hz); 8.57 (d, 1H, 4.2 Hz); 7.27 (t, 6 Hz); 6.96 (d, 2H, 8.4 Hz); 6.66 (d, 2H, 8.4 Hz); 5.78-5.68 (m, 1H); 5.42-5.33 (m, 1H); 3.96-3.89 (m, 1H); 3.80-3.57 (m, 5H); 3.41-3.34 (m, 1H); 3.10-2.90 (m, 1H); 2.78-2.66 (m, 1H); 2.21-2.10 (m, 1H); 2.06-1.93 (m, 1H); 1.70-1.60 (m, 1H); 1.52-1.41 (m, 1H); 1.39-1.26 (m, 1H); 1.25 (d, 3H, 4.8 Hz); 1.23 (d, 3H, 4.5 Hz); 0.83 (dd, 3H, 3 Hz, 4.5 Hz).

$^{13}$C NMR (75.5 MHz, DMSO-d$_6$) δ 172.68; 172.63; 159.15; 158.73; 157.38; 157.25; 130.89; 124.99; 116.03; 62.51; 62.12; 54.29; 49.27; 42.47; 32.77; 30.43; 28.85; 20.46; 19.59; 18.72; 17.39; 13.90; 13.09.

HRMS calc. for C$_{24}$H$_{36}$N$_4$O$_4$: 444.2736; found: 444.2726±0.0013

HPLC (standard gradient) t$_R$=6.80 min.

Compound 144

$^1$H NMR (300 MHz, CD$_3$OD) δ 7.4 (m, 1H); 7.27 (dt, 1H, 1.5 Hz, 6.6 Hz); 7.22-7.14 (m, 2H); 7.08-6.98 (m, 2H); 6.78 9t, 2H, 6.6 Hz); 4.45-4.39 (m, 2H); 4.15 (d, 2H, 8.1 Hz); 7.74 (d, 1H, 9.3 Hz); 3.54 (d, 1H, 10.8 Hz); 3.35-3.22 (m, 2H); 3.20 (q, 1H, 1.5 Hz); 2.82-2.71 (m, 1H); 2.61-2.55 (m, 1H); 2.21-2.11 (m, 1h); 2.02-1.94 (m, 1H); 1.74-1.40 (m, 5H); 1.04 (d, 3H, 6.6 Hz); 0.93 (d, 3H, 6.6 Hz); 0.74-0.64 9m, 1H); 0.45-0.28 (m, 2H); 0.15-0.08 (m, 1H); 0.06-0.02 (m, 1H).

$^{13}$C NMR (75.5 MHz, CD$_3$OD) δ 173.29; 172.14; 167.51; 155.47; 134.86; 134.81; 130.38; 130.31; 128.81; 128.25; 127.44; 121.63; 110.39; 107.71; 105.02; 67.10; 66.66; 62.81; 62.06; 60.10; 53.99; 41.44; 36.07; 31.91; 30.01; 29.18; 28.94; 27.79; 23.68; 23.15; 19.08; 18.25; 8.17; 4.98; 3.16.

HRMS: calc. for C$_{31}$H$_{41}$N$_4$O$_4$Cl 568.2816; found 568.2802±0.0017

F. Mass Spectral Data for Selected Compounds of the Invention

TABLE 2

Analysis of selected compounds of the invention

|  | Molecular Formula | Molecular Weight (calculated) | Monoisotopic Mass | M + H Found |
|---|---|---|---|---|
| 1 | C30H40N4O5 | 536.7 | 536 | 537 |
| 2 | C30H40N4O4 | 520.7 | 520 | 521 |
| 3 | C30H42N4O4 | 522.7 | 522 | 523 |
| 4 | C30H42N4O5 | 538.7 | 538 | 539 |
| 5 | C28H36N4O5 | 508.6 | 508 | 509 |
| 6 | C30H40N4O5S | 568.7 | 568 | 569 |
| 7 | C31H42N4O5 | 550.7 | 550 | 551 |
| 8 | C34H42N4O5 | 586.7 | 586 | 587 |
| 9 | C30H40N4O5 | 536.7 | 536 | 537 |
| 10 | C31H42N4O5 | 550.7 | 550 | 551 |
| 11 | C34H44N4O4 | 572.7 | 572 | 573 |
| 12 | C29H38N4O5 | 522.6 | 522 | 523 |
| 13 | C31H44N4O4 | 536.7 | 536 | 537 |
| 14 | C35H46N4O4 | 586.8 | 586 | 587 |
| 15 | C30H41N4O4Cl | 557.1 | 556 | 557 |
| 16 | C30H41N4O4Cl | 557.1 | 556 | 557 |
| 17 | C32H43N5O4 | 561.7 | 561 | 562 |
| 18 | C29H40N4O5 | 524.7 | 524 | 525 |
| 19 | C30H41N4O4F | 540.7 | 540 | 541 |
| 20 | C31H42N4O4 | 534.7 | 534 | 535 |
| 21 | C35H44N4O4 | 584.7 | 584 | 585 |
| 22 | C31H44N4O5 | 552.7 | 552 | 553 |
| 23 | C34H44N4O4 | 572.7 | 572 | 573 |
| 24 | C28H40N4O4S | 528.7 | 528 | 529 |
| 25 | C30H41N4O4Cl | 557.1 | 556 | 557 |
| 26 | C31H42N4O5 | 550.7 | 550 | 551 |
| 27 | C27H39N5O4S | 529.7 | 529 | 530 |
| 28 | C29H41N5O4 | 523.7 | 523 | 524 |
| 29 | C28H39N5O5 | 525.6 | 525 | 526 |
| 30 | C30H41N3O6 | 539.7 | 539 | 540 |
| 34 | C34H40N4O6 | 600.7 | 600 | 601 |
| 38 | C28H36N4O5 | 508.6 | 508 | 509 |
| 39 | C28H36N4O5 | 508.6 | 508 | 509 |
| 40 | C27H34N4O5 | 494.6 | 494 | 495 |
| 41 | C34H40N4O5 | 584.7 | 584 | 585 |
| 52 | C33H38N4O5 | 570.7 | 570 | 571 |
| 55 | C31H43N5O5 | 565.7 | 565 | 566 |
| 56 | C30H41N5O5 | 551.7 | 551 | 552 |
| 57 | C28H36N4O6 | 524.6 | 524 | 525 |
| 58 | C34H40N4O6 | 600.7 | 600 | 601 |
| 59 | C36H41N5O5 | 623.7 | 623 | 624 |

TABLE 2-continued

Analysis of selected compounds of the invention

|  | Molecular Formula | Molecular Weight (calculated) | Monoisotopic Mass | M + H Found |
|---|---|---|---|---|
| 60 | C35H42N4O6 | 614.7 | 614 | 615 |
| 65 | C24H36N4O4 | 444.6 | 444 | 445 |
| 71 | C29H40N4O6 | 540.7 | 540 | 541 |
| 72 | C38H42N4O5 | 634.8 | 634 | 635 |
| 76 | C38H42N4O5 | 634.8 | 634 | 635 |
| 77 | C31H42N4O5 | 550.7 | 550 | 551 |
| 80 | C31H42N4O5 | 550.7 | 550 | 551 |
| 85 | C30H40N4O5 | 536.7 | 536 | 537 |
| 87 | C36H46N4O4 | 598.8 | 598 | 599 |
| 88 | C34H50N4O5 | 594.8 | 594 | 595 |
| 89 | C31H44N4O4 | 536.7 | 536 | 537 |
| 90 | C36H46N4O4 | 598.8 | 598 | 599 |
| 91 | C30H42N4O5 | 538.7 | 538 | 539 |
| 92 | C31H44N4O5 | 552.7 | 552 | 553 |
| 96 | C28H38N4O5 | 510.6 | 510 | 511 |
| 97 | C33H46N4O5 | 578.7 | 578 | 579 |
| 98 | C24H39N5O4 | 461.6 | 461 | 462 |
| 99 | C24H39N5O4 | 461.6 | 461 | 462 |
| 109 | C29H41N5O5 | 539.7 | 539 | 540 |
| 110 | C29H41N5O5 | 539.7 | 539 | 540 |
| 111 | C30H41N3O6 | 539.7 | 539 | 540 |
| 112 | C31H44N4O5 | 552.7 | 552 | 553 |
| 120 | C30H38N4O5 | 534.6 | 534 | 535 |
| 121 | C32H45N5O6 | 595.7 | 595 | 596 |
| 122 | C31H43N4O4Cl | 571.2 | 570 | 571 |
| 123 | C29H41N5O4 | 523.7 | 523 | 524 |
| 124 | C29H41N5O4 | 523.7 | 523 | 524 |
| 125 | C30H40N4O5 | 536.7 | 536 | 537 |
| 126 | C32H46N4O5 | 566.7 | 566 | 567 |
| 127 | C30H38N6O3S | 562.7 | 562 | 563 |
| 128 | C32H46N4O5 | 566.7 | 566 | 567 |
| 129 | C35H46N4O4 | 586.8 | 586 | 587 |
| 130 | C29H42N4O4S | 542.7 | 542 | 543 |
| 131 | C31H43N4O4Cl | 571.2 | 570 | 571 |
| 132 | C31H43N4O4Cl | 571.2 | 570 | 571 |
| 133 | C31H43N4O4F | 554.7 | 554 | 555 |
| 134 | C25H37N4O3Cl | 477.0 | 476 | 477 |
| 135 | C31H45N5O5 | 567.7 | 567 | 568 |
| 136 | C34H45N5O4 | 587.8 | 587 | 588 |
| 137 | C28H41N5O4S | 543.7 | 543 | 544 |
| 138 | C30H42N5O4Cl | 572.1 | 571 | 572 |
| 139 | C30H42N5O4Cl | 572.1 | 571 | 572 |
| 140 | C30H42N5O4F | 555.7 | 555 | 556 |
| 141 | C32H44N4O5 | 564.7 | 564 | 565 |
| 142 | C35H44N4O4 | 584.7 | 584 | 585 |
| 143 | C29H40N4O4S | 540.7 | 540 | 541 |
| 144 | C31H41N4O4Cl | 569.1 | 568 | 569 |
| 145 | C31H41N4O4Cl | 569.1 | 568 | 569 |
| 146 | C31H41N4O4F | 552.7 | 552 | 553 |
| 147 | C31H43N5O5 | 565.7 | 565 | 566 |
| 148 | C34H43N5O4 | 585.7 | 585 | 586 |
| 149 | C30H40N5O4Cl | 570.1 | 569 | 570 |
| 150 | C30H40N5O4Cl | 570.1 | 569 | 570 |
| 151 | C30H40N5O4F | 553.7 | 553 | 554 |
| 152 | C29H41N5O5 | 539.7 | 539 | 540 |
| 153 | C32H41N5O4 | 559.7 | 559 | 560 |
| 154 | C26H37N4O4S | 515.7 | 515 | 516 |
| 155 | C28H38N5O4Cl | 544.1 | 543 | 544 |
| 156 | C28H38N5O4Cl | 544.1 | 543 | 544 |
| 157 | C28H38N5O4F | 527.6 | 527 | 528 |
| 158 | C27H37N6O4Cl | 545.1 | 544 | 545 |
| 159 | C31H44N4O5 | 552.7 | 552 | 553 |
| 160 | C31H44N4O5 | 552.7 | 552 | 553 |
| 161 | C31H45N5O4 | 551.7 | 551 | 552 |
| 162 | C31H44N4O4 | 536.7 | 536 | 537 |
| 163 | C31H44N4O4 | 536.7 | 536 | 537 |
| 164 | C31H44N4O4 | 536.7 | 536 | 537 |
| 165 | C31H44N4O5 | 552.7 | 552 | 553 |
| 166 | C31H44N4O5 | 552.7 | 552 | 553 |
| 167 | C32H42N4O4S | 578.8 | 578 | 579 |
| 168 | C28H40N4O4S | 528.7 | 528 | 529 |
| 169 | C31H43N4O4Cl | 571.2 | 570 | 571 |
| 170 | C30H40N4O4Cl2 | 591.6 | 590 | 591 |
| 171 | C30H40N4O4F2 | 558.7 | 558 | 559 |

TABLE 2-continued

Analysis of selected compounds of the invention

| | Molecular Formula | Molecular Weight (calculated) | Monoisotopic Mass | M + H Found |
|---|---|---|---|---|
| 172 | C32H46N4O6 | 582.7 | 582 | 583 |
| 173 | C34H43N3O5 | 573.7 | 573 | 574 |
| 174 | C31H43N3O6 | 553.7 | 553 | 554 |
| 175 | C31H44N4O5 | 552.7 | 552 | 553 |
| 176 | C31H44N4O5 | 552.7 | 552 | 553 |
| 177 | C29H40N4O5 | 524.7 | 524 | 525 |
| 178 | C29H40N4O6 | 540.7 | 540 | 541 |
| 179 | C32H40N4O5 | 560.7 | 560 | 561 |
| 180 | C26H36N4O5S | 516.7 | 516 | 517 |
| 181 | C28H37N4O5Cl | 545.1 | 544 | 545 |
| 182 | C28H37N4O5Cl | 545.1 | 544 | 545 |
| 183 | C28H37N4O5F | 528.6 | 528 | 529 |
| 184 | C31H40N6O4 | 560.7 | 560 | 561 |
| 185 | C27H37N6O4Cl | 545.1 | 544 | 545 |
| 186 | C31H40N6O5 | 576.7 | 576 | 577 |
| 187 | C31H41N4O4F3 | 590.7 | 590 | 591 |
| 188 | C30H41N4O4F | 540.7 | 540 | 541 |
| 189 | C30H41N5O6 | 567.7 | 567 | 568 |
| 190 | C33H42N4O4S | 590.8 | 590 | 591 |
| 191 | C32H44N4O5 | 564.7 | 564 | 565 |
| 192 | C31H40N4O4Cl2 | 603.6 | 602 | 603 |
| 193 | C31H40N4O4F2 | 570.7 | 570 | 571 |
| 194 | C32H48N6O6 | 612.8 | 612 | 613 |
| 195 | C32H46N4O5 | 566.7 | 566 | 567 |
| 196 | C32H43N6O4Cl | 611.2 | 610 | 611 |
| 197 | C32H45N6O5Cl | 629.2 | 628 | 629 |
| 198 | C32H43N4O4Cl | 583.2 | 582 | 583 |
| 199 | C27H39N4O6Cl | 551.1 | 550 | 551 |
| 200 | C31H39N4O4Cl | 567.1 | 566 | 567 |
| 201 | C34H42N4O4 | 570.7 | 570 | 571 |
| 202 | C31H42N4O5 | 550.7 | 550 | 551 |
| 203 | C30H40N5O5Cl | 586.1 | 585 | 586 |
| 204 | C29H40N7O4Cl | 586.1 | 585 | 586 |
| 205 | C32H45N4O4Cl | 585.2 | 584 | 585 |
| 206 | C29H40N5O6SCl | 622.2 | 621 | 622 |
| 207 | C29H39N6O5Cl | 587.1 | 586 | 587 |
| 208 | C29H41N7O5 | 567.7 | 567 | 568 |
| 209 | C30H41N5O6 | 567.7 | 567 | 568 |
| 210 | C31H45N5O5 | 567.7 | 567 | 568 |
| 211 | C30H42N5O4Cl | 572.1 | 571 | 572 |
| 212 | C31H44N5O4Cl | 586.2 | 585 | 586 |
| 213 | C30H40N4O5I2 | 790.5 | 790 | 791 |
| 214 | C30H42N4O6 | 554.7 | 554 | 555 |
| 215 | C30H43N5O5 | 553.7 | 553 | 554 |
| 216 | C32H43N4O4Cl | 583.2 | 582 | 583 |
| 217 | C31H40N4O4FCl | 587.1 | 586 | 587 |
| 218 | C31H43N4O4Cl | 571.2 | 570 | 571 |
| 219 | C30H40N4O4Cl2 | 591.6 | 590 | 591 |
| 220 | C31H43N4O4F | 554.7 | 554 | 555 |
| 221 | C30H40N4O4FCl | 575.1 | 574 | 575 |
| 222 | C34H50N4O5 | 594.8 | 594 | 595 |
| 223 | C32H44N4O6 | 580.7 | 580 | 581 |
| 224 | C36H48N4O4 | 600.8 | 600 | 601 |
| 225 | C37H48N4O5 | 628.8 | 628 | 629 |
| 226 | C39H49N5O4S | 683.9 | 683 | 684 |
| 227 | C42H52N4O4 | 676.9 | 676 | 677 |

Notes
1. Molecular formulas and molecular weights (MW) are calculated automatically from the structure via ActivityBase software (IDBS, Guildford, Surrey, UK) or, for MW only, from the freeware program Molecular Weight Calculator v. 6.32
2. M + H obtained from LC-MS analysis using the General Method as described
3. All analyses conducted on material after preparative HPLC purification Biological Methods and Results The compounds of the present invention were evaluated for their ability to interact at the human motilin receptor utilizing a competitive radioligand binding assay as described in Method B1. Further characterization of the interaction can be performed utilizing the functional assays described in Methods B2, B3 and B4. Some of these methods can be conducted, if so desired, in a high throughput manner to permit the simultaneous evaluation of many compounds. Other assays have also been described that are suitable for HTS, such as that based upon the stable expression of a synthetic gene for the human motilin receptor.

Results for the examination of representative compounds of the present invention using Method B1 are presented in Table 3. The binding activity is listed as ranges with the following levels: A=0.001-0.10 µM; B=0.10-1.0 µM; C=1.0-10.0 µM. In addition, the assay results of two additional compounds using this Method are shown below. As can be observed, this demonstrates the activity of a representative bicyclic compound of Formula IV of the invention, which resulted from incorporation of D-proline as the second recognition building block. Significantly, the lack of binding activity obtained with compound 121, which is the linear analogue of compound 1 ($K_i$=level B), illustrates the critical importance of the cyclic structure to attaining the desired interaction.

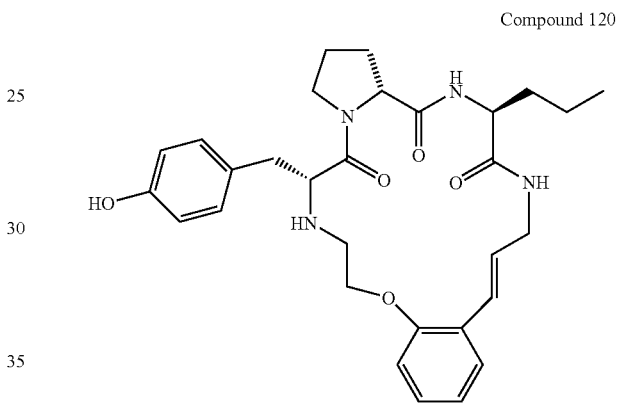

Compound 120

$K_i$ = level B

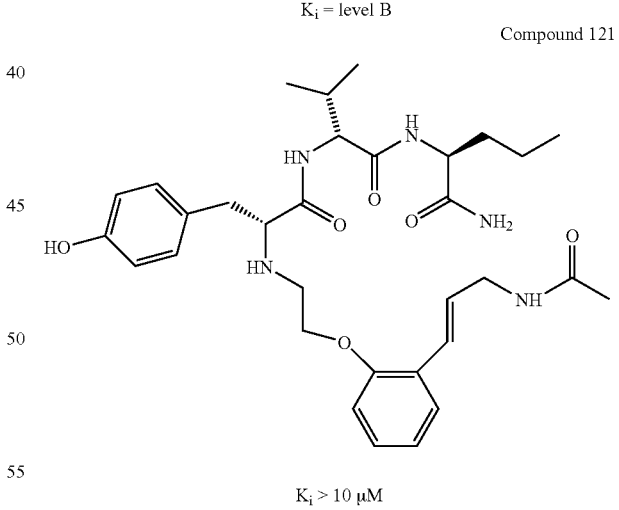

Compound 121

$K_i > 10$ µM

Competitive binding curves for two representative compounds of the invention (Compounds 8 and 11) are presented in FIG. 23 and FIG. 24, respectively.

For determination of functional significance of the binding, the compounds are preferably tested in the Aequorin assay as described in Method B2, although the procedure of Method B3 is also applicable. As can be seen from the data presented in Table 4, the representative compounds examined act as antagonists at the motilin receptor and are devoid of agonist activity at the concentrations studied. The functional activity is listed as ranges with the following levels: A=0.001-0.10 μM; B=0.10-1.0 μM. The higher sensitivity of the assay of Method B2, almost 100 times that of Method C, makes it the preferred one for this assessment. This is evident in the $EC_{50}$ values obtained in each for the positive agonist standard, motilin. Additionally, Method B2 measures, the actual signaling event, which makes it more relevant to the effect that is desired, whereas the assay of Method B3 simply measures GTP turnover.

TABLE 4

Demonstration of Antagonist Activity at the Motilin Receptor

| Compound | Aequorin (Method B2)[1] | |
|---|---|---|
| | Binding ($K_i$) | $IC_{50}$ |
| 142 | A | B |
| 149 | A | B |
| 167 | A | A |
| 168 | A | A |
| 212 | A | A |
| Motilin (human, porcine)[2] | 0.6 | not applicable |

[1] Activity is listed as ranges with the following levels: A = 0.001-0.10 μM; B = 0.10-1.0 μM
[2] Human and porcine motilin are the same peptide.

In addition, a common and scientifically-accepted ex vivo assay for the measurement of agonist or antagonist activity at the motilin receptor is the contraction of rabbit duodenum or other gastrointestinal smooth muscle tissue.[42-44] Agonists are defined as compounds that induce >50% contraction relative to the motilin peptide, whereas antagonists are defined as compounds that cause >50% inhibition of the response to motilin. Compounds of the present invention have shown significant antagonist activity in this assay. For example, compound 144 exhibited a $pA_2$=6.95, while compound 165 had a $pA_2$=7.17, as calculated from the Schild plots of the response obtained at various concentrations as described in Method B4.

Gastric motility is generally measured in the clinical setting as the time required for gastric emptying and subsequent transit time through the GI tract. Gastric emptying scans are well known to those skilled in the art an, briefly, comprise use of an oral contrast agent, such as barium, or a radiolabeled meal. Solid and liquids can be measured independently. A test food or liquid is radiolabeled with an isotope ($^{99m}Tc$) and after ingestion or administration, transit time through the GI tract and gastric emptying are measured by visualization using gamma cameras. These studies are performed before and after the administration of the therapeutic agent to quantify the efficacy of the compound.

Example Method B1

Competitive Radioligand Binding Assay (Motilin Receptor)

Materials:
Membranes were prepared from CHO cells stably transfected with the human motilin receptor and utilized at a quantity of 1.5 μg/assay point. [PerkinElmer™ SignalScreen® Product #6110544, PerkinElmer, Inc., Wellesley, Mass.]
[$^{125}I$]-Motilin (PerkinElmer, #NEX-378); final concentration: 0.04-0.06 nM Motilin (BacheM™, #H-4385, Bachem Bioscience Inc., King of Prussia, Pa.); final concentration: 1 μM
Multiscreen® Harvest plates-GF/B (Millipore™, #MAHFB1H60, Billerica, Mass.)
Deep-well polypropylene titer plate (Beckman Coulter™, #267006, Fullerton, Calif.)
TopSeal-A™ (PerkinElmer, #6005185, Wellesley, Mass.)
Bottom seal (Millipore™, #MATAHOP00, Billerica, Mass.)
MicroScint-0™ (PerkinElmer, #6013611, Wellesley, Mass.)
Binding Buffer: 50 mM Tris-HCl (pH 7.4), 10 mM $MgCl_2$, 1 mM EDTA, 0.1% BSA Assay Volumes:
150 μL of membranes diluted in binding buffer
10 μL of compound diluted in binding buffer
10 μL of radioligand ([$^{125}I$]-Motilin) diluted in binding buffer
Final Test Concentrations (N=11) for Compounds:
10, 5, 2, 1, 0.5, 0.2, 0.1, 0.05, 0.02, 0.01, 0.005 μM.

Compound Handling:
Compounds were provided frozen on dry ice at a stock concentration of 10 mM diluted in 100% DMSO and stored at −20° C. until the day of testing. On the test day, compounds were allowed to thaw at room temperature and than diluted in assay buffer according to the desired test concentrations. Under these conditions, the maximum final DMSO concentration in the assay was 0.5%.

Assay Protocol:
In deep-well plates, diluted cell membranes (1.5 μg/mL) are combined with 10 μL of either binding buffer (total binding, N=5), 1 μM motilin (non-specific binding, N=3) or the appropriate concentration of test compound. The reaction is initiated by addition of 10 μl of [$^{125}I$]-motilin (final conc. 0.04-0.06 nM) to each well. Plates are sealed with TopSeal-A, vortexed gently and incubated at room temperature for 2 hours. The reaction is arrested by filtering samples through pre-soaked (0.3% polyethyleneimine, 2 h) Multiscreen Harvest plates using a Tomtec® Harvester (Tomtec, Hamden, Conn.)), washed 9 times with 500 μL of cold 50 mM Tris-HCl (pH 7.4), and than plates are air-dried in a fumehood for 30 minutes. A bottom seal is applied to the plates prior to the addition of 25 μL of MicroScint-0™ to each well. Plates are then sealed with TopSeal-A® and counted for 30 sec per well on a TopCount® Microplate Scintillation and Luminescence Counter (PerkinElmer, Wellesley, Mass.) where results are expressed as counts per minute (cpm).

Data are analyzed by GraphPad™ Prism (GraphPad Software, San Diego, Calif.) using a variable slope non-linear regression analysis. $K_i$ values were calculated using a $K_d$ value of 0.16 nM for [$^{125}I$]-motilin (previously determined during membrane characterization).

$$D_{max} = 1 - \frac{\text{test concentration with maximal displacement} - \text{non-specific binding}}{\text{total binding} - \text{non-specific binding}} \times 100$$

where total and non-specific binding represent the cpm obtained in the absence or presence of 1 μM motilin, respectively.

Example Method B2

Aequorin Functional Assay (Motilin Receptor)

Materials:
Membranes were prepared using AequoScreen™ (EURO-SCREEN, Belgium) cell lines expressing the human motilin receptor (cell line ES-380-A; receptor accession #AF034632). This cell line is constructed by transfection of the human motilin receptor into CHO-K1 cells co-expressing $G_{\alpha 16}$ and the mitochondrially targeted Aequorin (Ref #ES_WT-A5).
Motilin (Bachem™, #H-4385, Bachem Bioscience Inc., King of Prussia, Pa.)
Assay buffer: DMEM-F12 (Dulbeccoe's Modified Eagles Medium) with 15 mM HEPES and 0.1% BSA (pH 7.0)
Coelenterazine (Molecular Probes™, Leiden, The Netherlands)

Final Test Concentrations (N=5) for Compounds:
10, 3.16, 1, 0.316, 0.1 µM.

Compound Handling:
Compounds were provided as dry films at a quantity of approximately 1.2 µmol in pre-formatted 96-well plates. Compounds were dissolved in 100% DMSO at a concentration of 10 mM and stored at −20° C. until further use. Daughter plates were prepared at a concentration of 500 µM in 30% DMSO with 0.1% BSA and stored at −20° C. until testing. On the test day, compounds were allowed to thaw at room temperature and than diluted in assay buffer according to the desired test concentrations. Under these conditions, the maximum final DMSO concentration in the assay was 0.6%.

Cell Preparation:
Cells are collected from culture plates with $Ca^{2+}$ and $Mg^{2+}$-free phosphate buffered saline (PBS) supplemented with 5 mM EDTA, pelleted for 2 minutes at 1000×g, resuspended in assay buffer (see above) at a density of $5×10^6$ cells/mL and incubated overnight in the presence of 5 µM coelenterazine. After loading, cells were diluted with assay buffer to a concentration of $5×10^5$ cells/mL.

Assay Protocol:
For agonist testing, 50 µl of the cell suspension was mixed with 50 µl of the appropriate concentration of test compound or motilin (reference agonist) in 96-well plates (duplicate samples). The emission of light resulting from receptor activation was recorded using the Functional Drug Screening System 6000 'FDSS 6000' (Hamamatsu Photonics K.K., Japan).

For antagonist testing, an approximate EC80 concentration of motilin (i.e. 0.5 nM; 100 µL) was injected onto the cell suspension containing the test compounds (duplicate samples) 15-30 minutes after the end of agonist testing and the consequent emission of light resulting from receptor activation was measured as described in the paragraph above.

Results are expressed as Relative Light Units (RLU). Concentration response curves were analyzed using GraphPad™ Prism® (GraphPad Software, San Diego, Calif.) by non-linear regression analysis (sigmoidal dose-response) based on the equation $E=E_{max}/(1+EC_{50}/C)n$ where E is the measured RLU value at a given agonist concentration (C), $E_{max}$ is the maximal response, $EC_{50}$ is the concentration producing 50% stimulation and n is the slope index. For agonist testing, results for each concentration of test compound were expressed as percent activation relative to the signal induced by motilin at a concentration equal to the $EC_{80}$ (i.e. 0.5 nM).

For antagonist testing, results for each concentration of test compound were expressed as percent inhibition relative to the signal induced by motilin at a concentration equal to the $EC_{80}$ (i.e. 0.5 nM).

Example Method B3

FlashPlate® Motilin [$^{35}$S]-GTPγS Functional Assay

Materials:
Membranes were prepared from CHO cells stably transfected with the human motilin receptor and utilized at a quantity of 1.5 µg/assay point.
[PerkinElmer™ SignalScreen® Product #6110544, PerkinElmer, Inc. Wellesley, Mass.]
GTPγS Guanosine 5'-[y-thio]triphosphate tetralithium salt (Sigma, #G-8634, Sigma-Aldrich, St. Louis, Mo.)
[$^{35}$S]-GTPγS (PerkinElmer, #NEX-030H)
Motilin (Bachem™, #H-4385, Bachem Bioscience Inc., King of Prussia, Pa.)
96-well FlashPlate® white polystyrene microplates (PerkinElmer, #SMP200, Wellesley, Mass.)
Deep-well polypropylene titer plate (Beckman Coulter™, #267006, Fullerton, Calif.)
TopSeal-A™ (PerkinElmer, #6005185, Wellesley, Mass.)
Assay Buffer: 50 mM Tris (pH 7.4), 100 mM NaCl, 10 mM $MgCl_2$, 1 mM EDTA, 1 µM GDP, 0.1% BSA Assay Volumes:
25 µL of compound diluted in assay buffer
25 µL of assay buffer (agonist assay) or 0.6 µM motilin (0.1 µM final concentration) diluted in assay buffer (antagonist assay)
100 µL of [$^{35}$S]-GTPγS diluted in assay buffer Final Test Concentrations (N=12) for Compounds:
50, 20, 10, 5, 2, 1, 0.5, 0.2, 0.1, 0.05, 0.02, 0.01 µM.

Compound Handling:
Compounds were provided frozen on dry ice at a stock concentration of 10 mM diluted in 100% DMSO and stored at −20° C. until the day of testing. On the test day, compounds were allowed to thaw at room temperature and than diluted in assay buffer according to the desired test concentrations. Under these conditions, the maximum final DMSO concentration in the assay was 0.5%.

Assay Protocol:
CHO membranes were immobilized into 96-well FlashPlate® microplates. Test compound, GTPγS, motilin and [$^{35}$S]-GTPγS were combined in each well according to the Assay Volumes described above.

For the assay to measure agonist activity, an additional 25 µl of buffer was added to each well in addition to 25 µL of either buffer (basal value, N=4), 1 µM (final conc.) motilin ($E_{max}$ value, N=3), 25 µM (final conc.) GTPγS (non-specific value, N=4), or the appropriate concentration of test compound (N=3).

For the assay to measure antagonist activity, an additional 25 µL of either buffer (unstimulated control) or motilin (0.1 µM final conc.) is added to each well, in addition to either 25 µL of buffer (basal value, N=3), 1 µM (final conc.) motilin ($E_{max}$ value, N=3), 25 µM (final conc.) GTPγS (non-specific value, N=4), or the appropriate concentration of test compound (N=3).

The reaction is initiated by addition of 100 mL of [$^{35}$S]-GTPγS to each well. Each plate is sealed (TopSeal-A™) and incubated in the dark at room temperature for 150 min. Then, plates are counted for 30 seconds per well on the TopCount® NXT.

Data were analyzed by GraphPad™ Prism® 3.0 (GraphPad Software, San Diego, Calif.) using non-linear regression analysis (sigmoidal dose-response) for the calculation of $IC_{50}/EC_{50}$ values.

$$E_{max}(\text{agonist}) \text{ or } D_{max}(\text{antagonist}) = \frac{\text{Top} - \text{Bottom}}{\text{Bottom}} \times 100$$

Where Top and Bottom correspond to the top and bottom values of the dose-response curve calculated by GraphPad™ Prism®).

Example Method B4

Rabbit Duodenum Contractility Assay

Duodenal segments were vertically suspended in organ chambers of 10 mL filled with Krebs buffer and connected to an isotonic force transducer, with a preload of 1 g. After a stabilization period, the muscle strips were challenged with $10^{-4}$ M acetylcholine and washed. This was repeated until a stable maximal contraction was obtained (2-3 times), with an interval of at least 20 minutes.

After a stable base line was reached, test compounds were added to the bath. After 15 min incubation, a dose response to motilin was recorded by adding logarithmically increasing concentrations of motilin to the bath (final concentration $10^{-9}$ to $10^{-6}$ M). A blank experiment (no test compound present) was also performed. At the end of the dose response curve, a supramaximal dose of acetylcholine ($10^{-4}$ M) was given and this response was used as a reference (100% contraction).

The results of experiments at different concentrations of test compound were combined and analyzed to derive the $pA_2$ value from the Schild plot.

It is appreciated that although specific experimental methods have been described herein for the purposes of illustration, various modifications to these experimental methods as well as alternate methods of experimentation may be used without departing from the scope of this invention.

TABLE 3

Binding activity of selected compounds

| # | $R_1$ | $R_3$ | $R_6$ | T | $K_i^{1,2}$ |
|---|---|---|---|---|---|
| 1 | 4-hydroxybenzyl | isopropyl | isobutyl | 2-(cinnamyl)phenyl-O-CH$_2$CH$_2$-X (with Z3) | B |
| 2 | benzyl | isopropyl | isobutyl | 2-(cinnamyl)phenyl-O-CH$_2$CH$_2$-X (with Z3) | A |
| 3 | benzyl | isopropyl | isobutyl | 2-(propyl)phenyl-O-CH$_2$CH$_2$-X (with Z3) | B |
| 4 | 4-hydroxybenzyl | isopropyl | isobutyl | 2-(propyl)phenyl-O-CH$_2$CH$_2$-X (with Z3) | A |
| 5 | 4-hydroxybenzyl | CH3 | isobutyl | 2-(cinnamyl)phenyl-O-CH$_2$CH$_2$-X (with Z3) | B |
| 6 | 4-hydroxybenzyl | isopropyl | -CH$_2$CH$_2$-S-CH$_3$ | 2-(cinnamyl)phenyl-O-CH$_2$CH$_2$-X (with Z3) | B |
| 7 | 4-hydroxybenzyl | isopropyl | n-butyl | 2-(cinnamyl)phenyl-O-CH$_2$CH$_2$-X (with Z3) | B |

TABLE 3-continued

Binding activity of selected compounds

| | R₁ | R₃ | R₆ | T | $K_i^{1,2}$ |
|---|---|---|---|---|---|
| 8 | 4-hydroxybenzyl | isopropyl | benzyl | 2-(CH=CH-CH₂-Z3)-phenyl-O-CH₂CH₂-X | B |
| 9 | 4-hydroxybenzyl | isopropyl | isopropyl | 2-(CH=CH-CH₂-Z3)-phenyl-O-CH₂CH₂-X | B |
| 10 | 4-hydroxybenzyl | isopropyl | isobutyl | 2-(CH=CH-CH₂-Z3)-phenyl-O-CH₂CH₂-X | A |
| 11 | naphthalen-2-ylmethyl | isopropyl | n-butyl | 2-(CH=CH-CH₂-Z3)-phenyl-O-CH₂CH₂-X | A |
| 12 | 4-hydroxybenzyl | isopropyl | ethyl | 2-(CH=CH-CH₂-Z3)-phenyl-O-CH₂CH₂-X | B |
| 13 | benzyl | isopropyl | isobutyl | 2-(CH₂CH₂CH₂-Z3)-phenyl-O-CH₂CH₂-X | B |
| 14 | naphthalen-2-ylmethyl | isopropyl | isobutyl | 2-(CH₂CH₂CH₂-Z3)-phenyl-O-CH₂CH₂-X | B |
| 15 | 3-chlorobenzyl | isopropyl | n-butyl | 2-(CH₂CH₂CH₂-Z3)-phenyl-O-CH₂CH₂-X | A |
| 16 | 4-chlorobenzyl | isopropyl | n-butyl | 2-(CH₂CH₂CH₂-Z3)-phenyl-O-CH₂CH₂-X | A |
| 17 | indol-3-ylmethyl | isopropyl | n-butyl | 2-(CH₂CH₂CH₂-Z3)-phenyl-O-CH₂CH₂-X | B |
| 18 | 4-hydroxybenzyl | ethyl | n-butyl | 2-(CH₂CH₂CH₂-Z3)-phenyl-O-CH₂CH₂-X | B |

TABLE 3-continued
Binding activity of selected compounds
| | R₁ | R₃ | R₆ | T | $K_i^{1,2}$ |
|---|---|---|---|---|---|
| 19 | 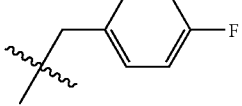 |  | 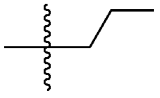 | 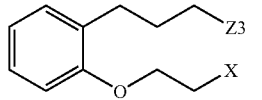 | A |
| 20 | 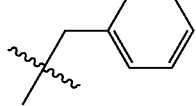 |  | 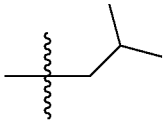 | 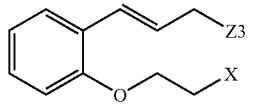 | B |
| 21 | 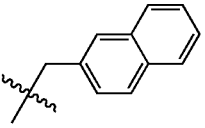 |  | 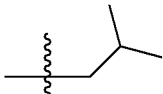 | 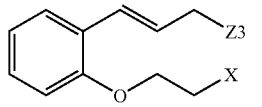 | A |
| 22 | 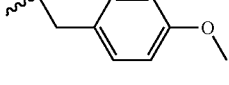 |  |  | 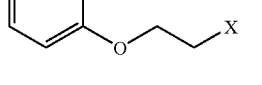 | A |
| 23 | 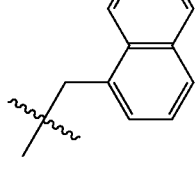 |  |  | 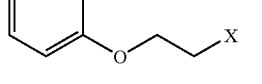 | A |
| 24 | 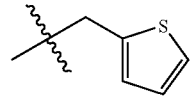 |  | 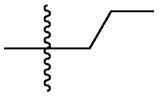 | 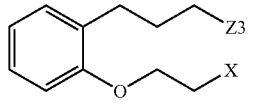 | A |
| 25 | 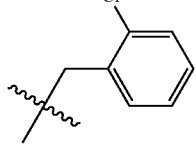 |  | 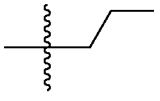 | 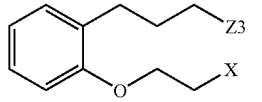 | B |
| 26 | 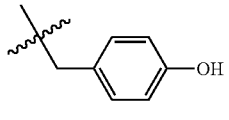 |  | 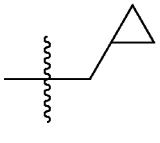 | 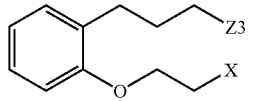 | A |
| 27 | 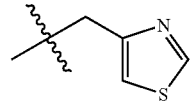 |  | 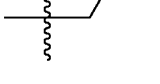 | 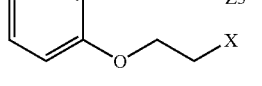 | B |
| 28 | 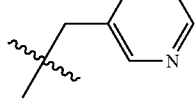 |  | 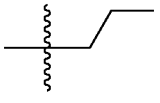 | 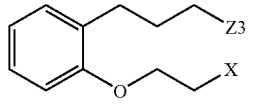 | B |

TABLE 3-continued

Binding activity of selected compounds

| | R₁ | R₃ | R₆ | T | $K_i^{1,2}$ |
|---|---|---|---|---|---|
| 29 | 4-hydroxybenzyl | isopropyl | n-butyl | 2-(propyl-Z3)phenyl-O-CH₂CH₂-X | B |
| 30 | 4-hydroxybenzyl | isopropyl | n-butyl | 2-(propyl-Z3)phenyl-O-CH₂CH₂-X | B |
| 34 | 4-hydroxybenzyl | 4-hydroxybenzyl | n-propyl | 2-(allyl-Z3)phenyl-O-CH₂CH₂-X | B |
| 38 | 4-hydroxybenzyl | isopropyl | CH3 | 2-(allyl-Z3)phenyl-O-CH₂CH₂-X | C |
| 39 | 4-hydroxybenzyl | isopropyl | H | 2-(allyl-Z3)phenyl-O-CH₂CH₂-X | B |
| 40 | 4-hydroxybenzyl | isopropyl | H | 2-(allyl-Z3)phenyl-O-CH₂CH₂-X | C |
| 41 | 4-hydroxybenzyl | benzyl | n-propyl | 2-(allyl-Z3)phenyl-O-CH₂CH₂-X | C |
| 52 | 4-hydroxybenzyl | isopropyl | phenyl | 2-(allyl-Z3)phenyl-O-CH₂CH₂-X | B |
| 55 | 4-hydroxybenzyl | isopropyl | -(CH₂)₄NH₂ | 2-(allyl-Z3)phenyl-O-CH₂CH₂-X | B |
| 56 | 4-hydroxybenzyl | isopropyl | -(CH₂)₃NH₂ | 2-(allyl-Z3)phenyl-O-CH₂CH₂-X | B |
| 57 | 4-hydroxybenzyl | isopropyl | -CH₂OH | 2-(allyl-Z3)phenyl-O-CH₂CH₂-X | B |
| 58 | 4-hydroxybenzyl | isopropyl | 4-hydroxybenzyl | 2-(allyl-Z3)phenyl-O-CH₂CH₂-X | B |

TABLE 3-continued

Binding activity of selected compounds

| | R₁ | R₃ | R₆ | T | $K_i^{1,2}$ |
|---|---|---|---|---|---|
| 59 | 4-hydroxybenzyl | isopropyl | (1H-indol-3-yl)methyl | 2-(2-(X)ethoxy)phenyl-CH=CH-CH₂-Z3 | B |
| 60 | 4-hydroxybenzyl | isopropyl | 4-methoxybenzyl | 2-(2-(X)ethoxy)phenyl-CH=CH-CH₂-Z3 | C |
| 65 | 4-hydroxybenzyl | isopropyl | n-propyl | X-CH₂-CH=CH-CH₂-CH₂-Z3 | B |
| 71 | 4-hydroxybenzyl | isopropyl | n-propyl | X-CH₂CH₂-O-(1,3-phenylene)-O-CH₂CH₂-Z3 | B |
| 72 | 4-hydroxybenzyl | isopropyl | (naphthalen-2-yl)methyl | 2-(2-(X)ethoxy)phenyl-CH=CH-CH₂-Z3 | B |
| 76 | 4-hydroxybenzyl | (naphthalen-2-yl)methyl | n-propyl | 2-(2-(X)ethoxy)phenyl-CH=CH-CH₂-Z3 | C |
| 77 | 4-hydroxybenzyl | n-butyl | n-propyl | 2-(2-(X)ethoxy)phenyl-CH=CH-CH₂-Z3 | C |
| 80 | 4-hydroxybenzyl | isopropyl | sec-butyl | 2-(2-(X)ethoxy)phenyl-CH=CH-CH₂-Z3 | B |
| 85 | 4-hydroxybenzyl | isopropyl | H | 2-(2-(X)ethoxy)phenyl-CH=CH-CH₂-Z3 | B |
| 87 | 4-biphenylmethyl | isopropyl | n-propyl | 2-(2-(X)ethoxy)phenyl-CH₂CH₂CH₂-Z3 | B |
| 88 | 4-(tert-butoxy)benzyl | isopropyl | n-propyl | 2-(2-(X)ethoxy)phenyl-CH₂CH₂CH₂-Z3 | C |

TABLE 3-continued

Binding activity of selected compounds

| | R₁ | R₃ | R₆ | T | $K_i^{1,2}$ |
|---|---|---|---|---|---|
| 89 | (CH₂)₂-phenyl | isopropyl | n-butyl | 2-substituted phenyl with propyl-Z3 and OCH₂CH₂-X | C |
| 90 | CH(phenyl)₂ | isopropyl | n-butyl | 2-substituted phenyl with propyl-Z3 and OCH₂CH₂-X | C |
| 91 | CH₂-C₆H₄-OH | sec-butyl | n-butyl | 2-substituted phenyl with propyl-Z3 and OCH₂CH₂-X | C |
| 92 | CH₂-C₆H₄-OH | tert-butyl | n-butyl | 2-substituted phenyl with propyl-Z3 and OCH₂CH₂-X | B |
| 96 | CH₂-C₆H₄-OH | H | n-butyl | 2-substituted phenyl with propyl-Z3 and OCH₂CH₂-X | C |
| 97 | CH₂-C₆H₄-OH | 1-cyclohexylethyl | n-butyl | 2-substituted phenyl with propyl-Z3 and OCH₂CH₂-X | C |
| 98 | CH₂-C₆H₄-OH | isopropyl | n-butyl | X-(CH₂)₃-NH-(CH₂)₂-Z3 | C |
| 99 | CH₂-C₆H₄-OH | isopropyl | n-butyl | X-(CH₂)₂-N(CH₃)-(CH₂)₂-Z3 | C |
| 109 | CH₂-C₆H₄-OH | isopropyl | CH₂CH₂-NH₂ | 2-substituted phenyl with propyl-Z3 and OCH₂CH₂-X | B |
| 110 | CH₂-C₆H₄-OH | isopropyl | n-butyl | 2,3-substituted pyridine with propyl-Z3 and OCH₂CH₂-X | B |
| 111 | CH₂-C₆H₄-OH | isopropyl | n-butyl | 2-substituted phenyl with propyl-Z3 and OCH₂CH₂-X | B |

TABLE 3-continued

Binding activity of selected compounds

| | R₁ | R₃ | R₆ | T | $K_i^{1,2}$ |
|---|---|---|---|---|---|
| 112 | 4-hydroxybenzyl | isopropyl | n-butyl | 2-(3-Z3-propyl)phenyl-O-CH₂CH₂-X | B |
| 122 | (pyridin-3-yl)methyl | isopropyl | n-butyl | 2-(3-Z3-propyl)phenyl-O-CH₂CH₂-X | B |
| 123 | (pyridin-2-yl)methyl | isopropyl | n-butyl | 2-(3-Z3-propyl)phenyl-O-CH₂CH₂-X | B |
| 124 | (pyridin-4-yl)methyl | isopropyl | n-butyl | 2-(3-Z3-propyl)phenyl-O-CH₂CH₂-X | B |
| 125 | 4-hydroxybenzyl | cyclopropyl | n-butyl | 2-(3-Z3-propyl)phenyl-O-CH₂CH₂-X | B |
| 126 | 4-hydroxybenzyl | isopropyl | isobutyl | 2-(3-Z3-propyl)phenyl-O-CH₂CH₂-X | B |
| 127 | (1H-imidazol-4-yl)-CMe₂- | isopropyl | n-butyl | bis(2-CH₂-phenyl) sulfide with X and Z3 | B |
| 128 | 4-methoxybenzyl | isopropyl | isobutyl | 2-(3-Z3-propyl)phenyl-O-CH₂CH₂-X | B |
| 129 | (naphthalen-1-yl)methyl | isopropyl | isobutyl | 2-(3-Z3-propyl)phenyl-O-CH₂CH₂-X | A |
| 130 | (thiophen-2-yl)-CMe₂- | isopropyl | isobutyl | 2-(3-Z3-propyl)phenyl-O-CH₂CH₂-X | B |

TABLE 3-continued
Binding activity of selected compounds
| | R₁ | R₃ | R₆ | T | $K_i^{1,2}$ |
|---|---|---|---|---|---|
| 131 | 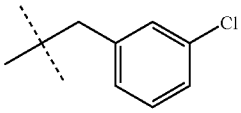 | 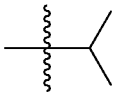 | 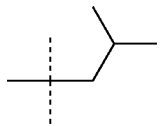 | 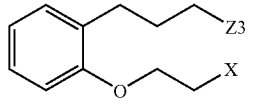 | A |
| 132 | 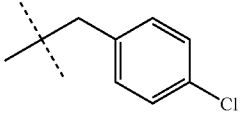 | 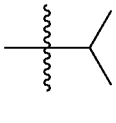 | 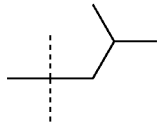 | 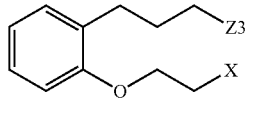 | A |
| 133 | 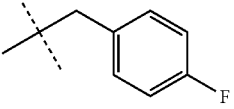 | 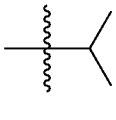 | 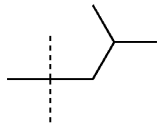 | 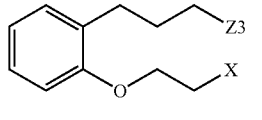 | A |
| 134 | 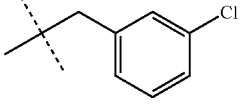 | 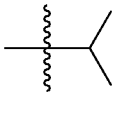 | 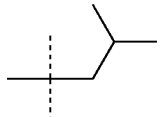 | 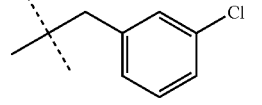 | C |
| 135 | 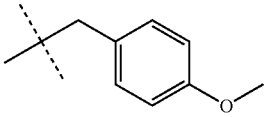 | 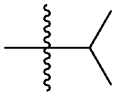 | 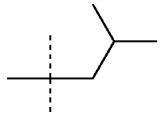 | 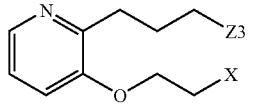 | B |
| 136 | 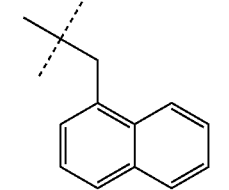 | 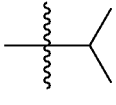 | 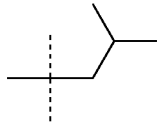 | 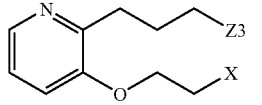 | B |
| 137 | 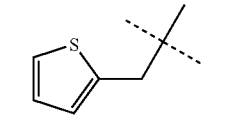 | 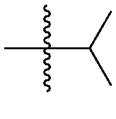 | 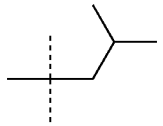 | 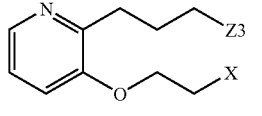 | B |
| 138 | 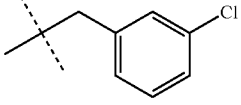 | 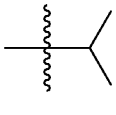 | 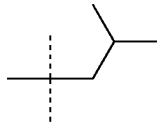 | 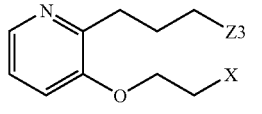 | B |
| 139 | 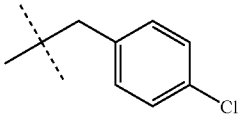 | 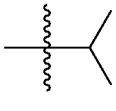 | 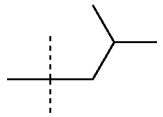 | 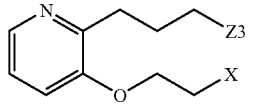 | B |
| 140 | 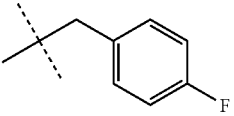 | 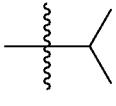 | 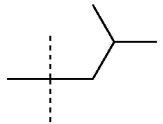 | 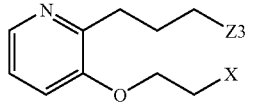 | B |

TABLE 3-continued

Binding activity of selected compounds

| | R₁ | R₃ | R₆ | T | $K_i^{1,2}$ |
|---|---|---|---|---|---|
| 141 | 4-methoxybenzyl (neopentyl) | isopropyl | cyclopropylmethyl | 2-(propyl-Z3)phenyl-O-CH₂CH₂-X | A |
| 142 | 1-naphthylmethyl (neopentyl) | isopropyl | cyclopropylmethyl | 2-(propyl-Z3)phenyl-O-CH₂CH₂-X | A |
| 143 | 1-naphthylmethyl (neopentyl) | isopropyl | cyclopropylmethyl | 2-(propyl-Z3)phenyl-O-CH₂CH₂-X | B |
| 144 | 2-thienylmethyl (neopentyl) | isopropyl | cyclopropylmethyl | 2-(propyl-Z3)phenyl-O-CH₂CH₂-X | A |
| 145 | | isopropyl | cyclopropylmethyl | 2-(propyl-Z3)phenyl-O-CH₂CH₂-X | A |
| 146 | 3-chlorobenzyl (neopentyl) | isopropyl | cyclopropylmethyl | 2-(propyl-Z3)phenyl-O-CH₂CH₂-X | A |
| 147 | 4-chlorobenzyl (neopentyl) | isopropyl | cyclopropylmethyl | pyridyl-(propyl-Z3)-O-CH₂CH₂-X | B |
| 148 | 4-fluorobenzyl (neopentyl) | isopropyl | cyclopropylmethyl | pyridyl-(propyl-Z3)-O-CH₂CH₂-X | B |
| 149 | 4-methoxybenzyl (neopentyl) | isopropyl | cyclopropylmethyl | pyridyl-(propyl-Z3)-O-CH₂CH₂-X | A |

TABLE 3-continued
Binding activity of selected compounds
| | R₁ | R₃ | R₆ | T | $K_i^{1,2}$ |
|---|---|---|---|---|---|
| 150 | 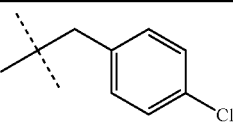 | 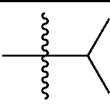 | 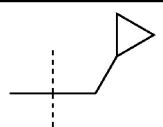 | 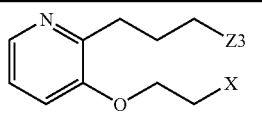 | B |
| 151 | 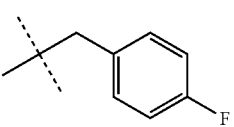 | 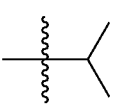 | 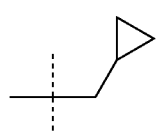 | 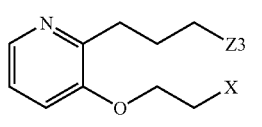 | B |
| 152 | 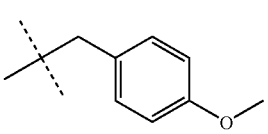 | 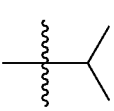 | 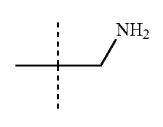 | 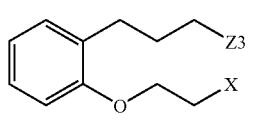 | B |
| 153 | 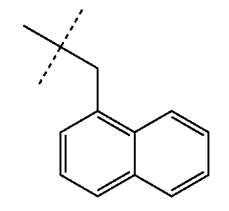 | 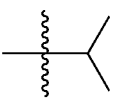 | 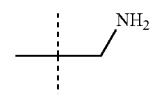 | 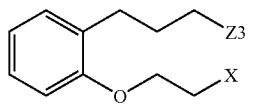 | B |
| 154 | 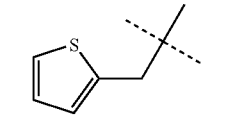 | 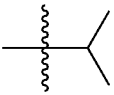 | 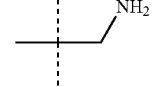 | 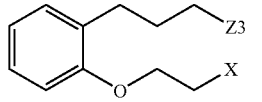 | B |
| 155 | 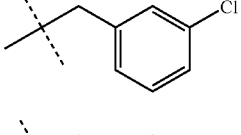 | 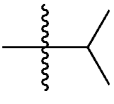 | 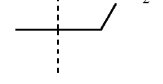 | 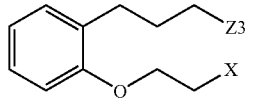 | A |
| 156 | 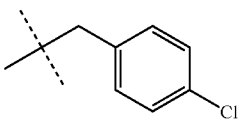 | 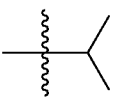 | 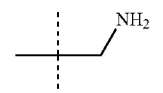 | 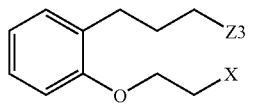 | A |
| 157 | 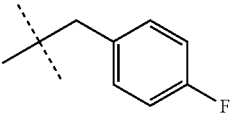 | 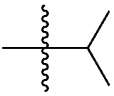 | 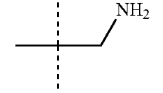 | 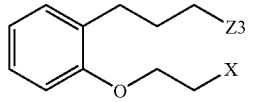 | B |
| 158 | 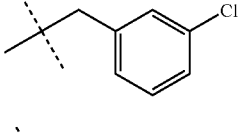 | 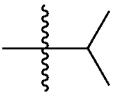 | 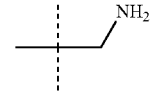 | 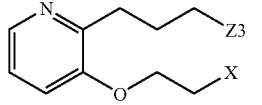 | A |
| 159 | 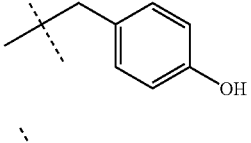 | 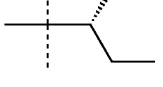 | 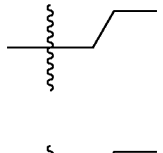 | 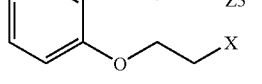 | B |
| 160 | 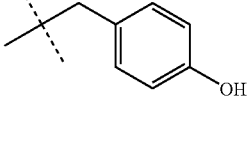 | 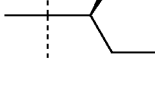 | 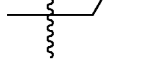 | 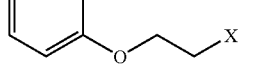 | B |

TABLE 3-continued

Binding activity of selected compounds

| # | R₁ | R₃ | R₆ | T | $K_i^{1,2}$ |
|---|---|---|---|---|---|
| 161 | 4-(aminomethyl)benzyl | isopropyl | n-propyl | 2-(2-(3-Z3-propyl)phenoxy)ethyl-X | B |
| 162 | 2-methylbenzyl | isopropyl | n-propyl | 2-(2-(3-Z3-propyl)phenoxy)ethyl-X | B |
| 163 | 3-methylbenzyl | isopropyl | n-propyl | 2-(2-(3-Z3-propyl)phenoxy)ethyl-X | A |
| 164 | 4-methylbenzyl | isopropyl | n-propyl | 2-(2-(3-Z3-propyl)phenoxy)ethyl-X | B |
| 165 | 3-methoxybenzyl | isopropyl | n-propyl | 2-(2-(3-Z3-propyl)phenoxy)ethyl-X | A |
| 166 | 2-methoxybenzyl | isopropyl | n-propyl | 2-(2-(3-Z3-propyl)phenoxy)ethyl-X | B |
| 167 | benzothiophen-3-ylmethyl | isopropyl | n-propyl | 2-(2-(3-Z3-propyl)phenoxy)ethyl-X | A |
| 168 | thiophen-3-ylmethyl | isopropyl | n-propyl | 2-(2-(3-Z3-propyl)phenoxy)ethyl-X | A |
| 169 | 3-chlorobenzyl | isopropyl | n-propyl | 2-(2-(3-Z3-propyl)phenoxy)ethyl-X | B |
| 170 | 3,4-dichlorobenzyl | isopropyl | n-propyl | 2-(2-(3-Z3-propyl)phenoxy)ethyl-X | A |
| 171 | 3,4-difluorobenzyl | isopropyl | n-propyl | 2-(2-(3-Z3-propyl)phenoxy)ethyl-X | A |

TABLE 3-continued

Binding activity of selected compounds

| | R₁ | R₃ | R₆ | T | $K_i^{1,2}$ |
|---|---|---|---|---|---|
| 172 | 3,4-dimethoxybenzyl | isopropyl | n-butyl | 2-(propyl-Z3)phenyl-O-CH₂CH₂-X | A |
| 173 | 1-naphthylmethyl | isopropyl | n-butyl | 2-(propyl-Z3)phenyl-O-CH₂CH₂-X | B |
| 174 | 4-methoxybenzyl | isopropyl | n-butyl | 2-(propyl-Z3)phenyl-O-CH₂CH₂-X | B |
| 175 | 4-hydroxybenzyl | isopropyl | n-butyl | chroman-type with Z3, X | B |
| 176 | 4-hydroxybenzyl | isopropyl | n-butyl | chroman-type with Z3, X | B |
| 177 | 4-hydroxybenzyl | isopropyl | n-butyl | 2-(ethyl-Z3)phenyl-O-CH₂CH₂-X | B |
| 178 | 4-methoxybenzyl | isopropyl | CH₂OH | 2-(propyl-Z3)phenyl-O-CH₂CH₂-X | B |
| 179 | 1-naphthylmethyl | isopropyl | CH₂OH | 2-(propyl-Z3)phenyl-O-CH₂CH₂-X | B |
| 180 | 2-thienylmethyl | isopropyl | CH₂OH | 2-(propyl-Z3)phenyl-O-CH₂CH₂-X | B |
| 181 | 3-chlorobenzyl | isopropyl | CH₂OH | 2-(propyl-Z3)phenyl-O-CH₂CH₂-X | A |

TABLE 3-continued

Binding activity of selected compounds

| | R₁ | R₃ | R₆ | T | $K_i^{1,2}$ |
|---|---|---|---|---|---|
| 182 | 4-Cl-benzyl (neopentyl-linked) | isopropyl | C(CH₃)₂OH | 2-(propyl-Z3)-phenyl-O-ethyl-X | A |
| 183 | 4-F-benzyl | isopropyl | CH₂OH | 2-(propyl-Z3)-phenyl-O-ethyl-X | B |
| 184 | 1-naphthyl-CH₂- (neopentyl) | isopropyl | CH₂NH₂ | 2-(propyl-Z3)-3-O-ethyl-X-pyridyl | B |
| 185 | 4-Cl-benzyl | isopropyl | CH₂NH₂ | 2-(propyl-Z3)-3-O-ethyl-X-pyridyl | B |
| 186 | 4-OH-benzyl | isopropyl | imidazol-4-yl-CH₂- | 2-(propyl-Z3)-phenyl-O-ethyl-X | B |
| 187 | 3-CF₃-benzyl | isopropyl | n-propyl | 2-(propyl-Z3)-phenyl-O-ethyl-X | A |
| 188 | 3-F-benzyl | isopropyl | n-propyl | 2-(propyl-Z3)-phenyl-O-ethyl-X | A |
| 189 | 4-NO₂-benzyl | isopropyl | n-propyl | 2-(propyl-Z3)-phenyl-O-ethyl-X | B |
| 190 | benzothiophen-3-yl-CH₂- | isopropyl | cyclopropyl-CH₂- | 2-(propyl-Z3)-phenyl-O-ethyl-X | A |
| 191 | 3-OMe-benzyl | isopropyl | cyclopropyl-CH₂- | 2-(propyl-Z3)-phenyl-O-ethyl-X | A |

TABLE 3-continued
Binding activity of selected compounds
| | R₁ | R₃ | R₆ | T | $K_i^{1,2}$ |
|---|---|---|---|---|---|
| 192 | 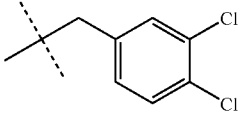 | 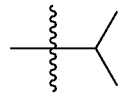 | 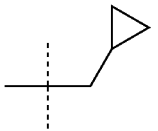 | 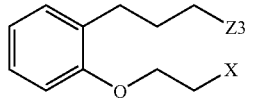 | A |
| 193 | 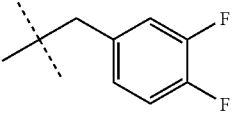 | 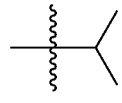 | 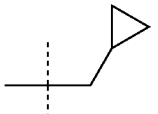 | 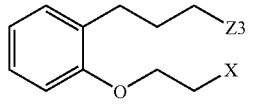 | A |
| 194 | 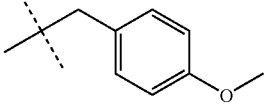 | 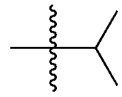 | 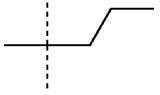 | 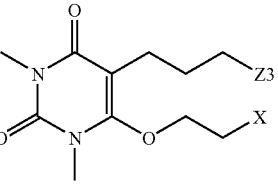 | B |
| 195 | 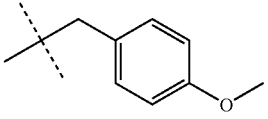 | 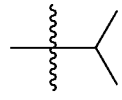 | 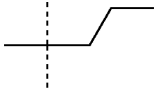 | 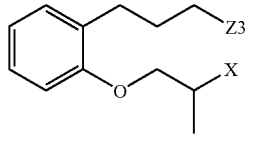 | A |
| 196 | 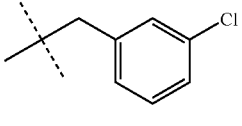 | 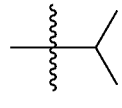 | 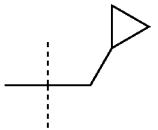 | 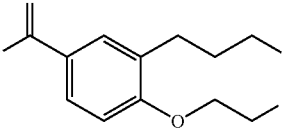 | |
| 197 | 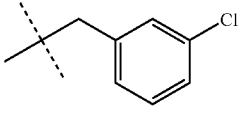 | 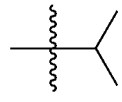 | 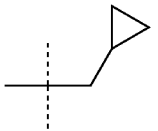 | 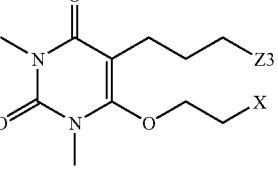 | |
| 198 | 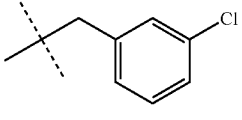 | 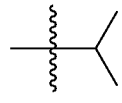 | 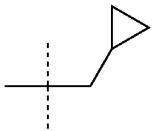 | 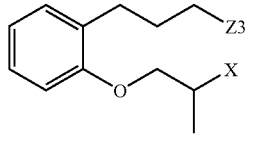 | A |
| 199 | 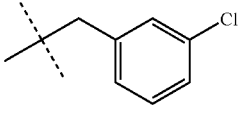 | 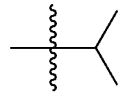 | 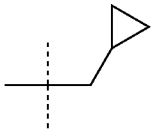 | 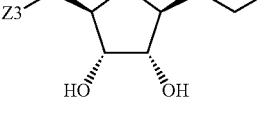 | B |
| 200 | 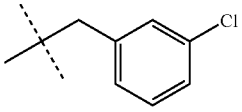 | 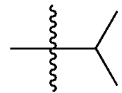 | 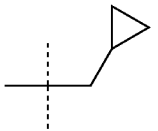 | 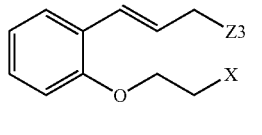 | A |

TABLE 3-continued

Binding activity of selected compounds

| | R₁ | R₃ | R₆ | T | $K_i^{1,2}$ |
|---|---|---|---|---|---|
| 201 | 1-naphthylmethyl | isopropyl | n-butyl | 2-(vinyl-Z3)phenyl-O-CH₂CH₂-X | B |
| 202 | 3-methoxybenzyl | isopropyl | n-butyl | 2-(vinyl-Z3)phenyl-O-CH₂CH₂-X | A |
| 203 | 4-chlorobenzyl | isopropyl | -CH₂CH₂-NHC(O)CH₃ | 2-(propyl-Z3)phenyl-O-CH₂CH₂-X | B |
| 204 | 4-chlorobenzyl | isopropyl | -CH₂CH₂-NHC(=NH)NH₂ | 2-(propyl-Z3)phenyl-O-CH₂CH₂-X | A |
| 205 | 3-chlorobenzyl | isopropyl | isobutyl | 2-(propyl-Z3)phenyl-O-CH₂CH₂-X | B |
| 206 | 4-chlorobenzyl | isopropyl | -CH₂CH₂-NHS(O)₂CH₃ | 2-(propyl-Z3)phenyl-O-CH₂CH₂-X | B |
| 207 | 4-chlorobenzyl | isopropyl | -CH₂CH₂-NHC(O)NH₂ | 2-(propyl-Z3)phenyl-O-CH₂CH₂-X | B |
| 208 | 4-hydroxybenzyl | isopropyl | -CH₂CH₂-NHC(=NH)NH₂ | 2-(propyl-Z3)phenyl-O-CH₂CH₂-X | B |
| 209 | 4-hydroxybenzyl | isopropyl | -CH₂CH₂-NHC(O)CH₃ | 2-(propyl-Z3)phenyl-O-CH₂CH₂-X | C |
| 210 | 4-hydroxybenzyl | isopropyl | -CH₂-NH-iPr | 2-(propyl-Z3)phenyl-O-CH₂CH₂-X | B |

TABLE 3-continued
Binding activity of selected compounds
| | R₁ | R₃ | R₆ | T | $K_i^{1,2}$ |
|---|---|---|---|---|---|
| 211 | 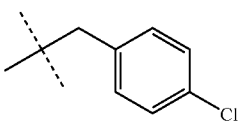 | 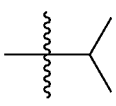 | 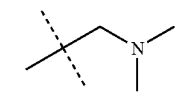 | 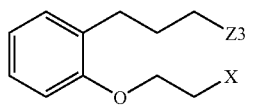 | A |
| 212 | 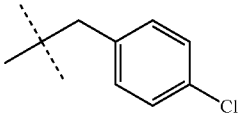 | 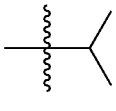 | 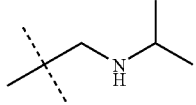 | 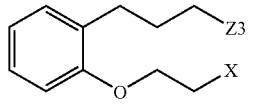 | A |
| 213 | 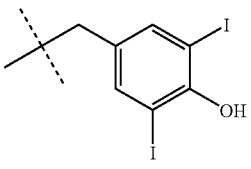 | 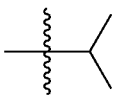 | 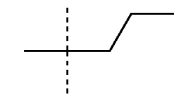 | 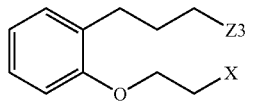 | B |
| 214 | 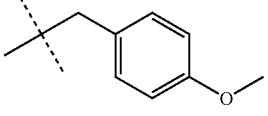 | 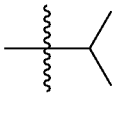 | 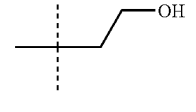 | 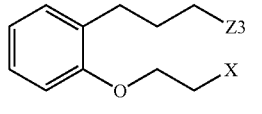 | B |
| 215 | 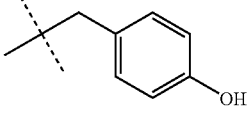 | 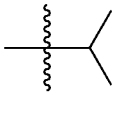 | 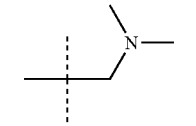 | 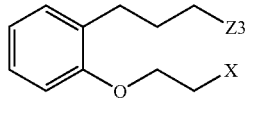 | B |
| 216 | 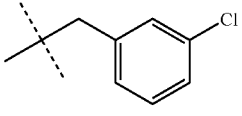 | 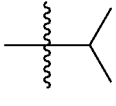 | 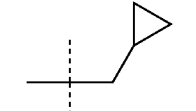 | 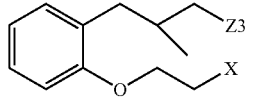 | A |
| 217 | 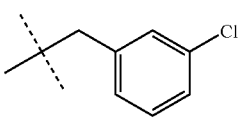 | 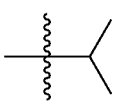 | 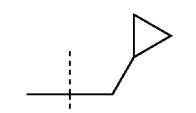 | 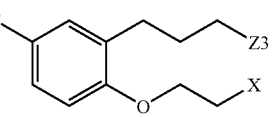 | B |
| 218 | 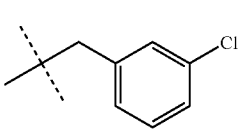 | 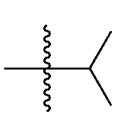 | 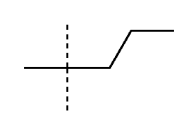 | 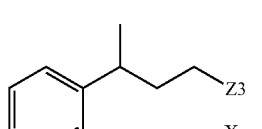 | A |
| 219 | 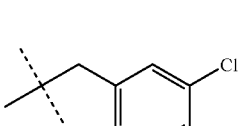 | 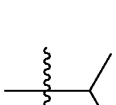 | 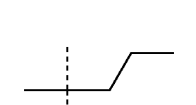 | 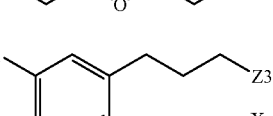 | B |
| 220 | 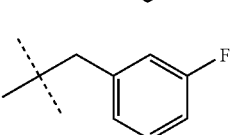 | 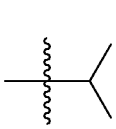 | 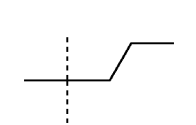 | 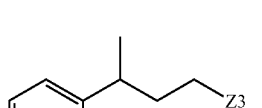 | A |

TABLE 3-continued

Binding activity of selected compounds

| | $R_1$ | $R_3$ | $R_6$ | T | $K_i^{1,2}$ |
|---|---|---|---|---|---|
| 221 | | isopropyl | propyl | 4-F-2-(OCH$_2$CH$_2$X)-phenyl with (CH$_2$)$_3$Z$_3$ | B |
| 222 | 2-tBu-4-(CH$_2$)-phenol | isopropyl | propyl | 2-(OCH$_2$CH$_2$X)-phenyl with (CH$_2$)$_3$Z$_3$ | A |
| 223 | 4-(CH$_2$)-phenol | isopropyl | propyl | 2-(OCH$_2$CH$_2$X)-phenyl with (CH$_2$)$_3$Z$_3$ | C |
| 224 | 1-naphthylmethyl | isopropyl | isobutyl | 2-(OCH$_2$CH$_2$X)-phenyl with (CH$_2$)$_3$Z$_3$ | B |
| 225 | 1-naphthylmethyl | isopropyl | isobutyl | 2-(OCH$_2$CH$_2$X)-phenyl with (CH$_2$)$_3$Z$_3$ | B |
| 226 | 1-naphthylmethyl | isopropyl | isobutyl | 2-(OCH$_2$CH$_2$X)-phenyl with (CH$_2$)$_3$Z$_3$ | C |
| 227 | 1-naphthylmethyl | isopropyl | isobutyl | 2-(OCH$_2$CH$_2$X)-phenyl with (CH$_2$)$_3$Z$_3$ | B |

Notes

Radioligand competitive binding assays performed using Method B1

Values reported as ranges: A = 0.001-0.100 μM; B = 0.100-1.0 μM; C = 1.0-10.0 μM X is NH except for:

Compound 223 and 225, X is:

Compound 224, X is NMe

Compound 226, X is:

Compound 227, X is $Z_1$, $Z_2$ and $Z_3$ are NH except for compounds 30, 173 and 174 and where Z1 is O and compound 111 where $Z_2$ is O.

$R_2$, $R_4$ and $R_5$ are hydrogen except for compound 85 where it is m, $n_1$ and p are zero.

What is claimed is:

1. A compound represented by the general formula (I):

(I)

or pharmaceutically acceptable salts thereof wherein:

$Z_1$, $Z_2$, and $Z_3$ are independently $NR_{10}$, wherein $R_{10}$ is selected from the group consisting of hydrogen and lower alkyl;

$R_1$ is —$(CH_2)_q R_{11}$, wherein q is 0, 1 or 2, and $R_{11}$ is selected from the group consisting of:

wherein $A_1$, $A_2$, $A_3$, $A_4$ and $A_5$ are each optionally present and are independently selected from the group consisting of halogen, alkyl, substituted alkyl, trifluoromethyl, hydroxy, alkoxy and nitro;

and;

$B_1$, $B_2$, $B_3$, $B_4$, $B_5$ and $B_7$ are independently $NR_{14a}$, S or O, wherein $R_{14a}$ is selected from the group consisting of hydrogen, alkyl, substituted alkyl, formyl, acyl, carboxyalkyl, carboxyaryl, amido, sulfonyl and sulfonamido;

$B_6$ and $B_8$ are independently N or CH;

$R_2$ is hydrogen,
$R_3$ is selected from the group consisting of: —$(CH_2)_sCH_3$, —$CH(CH_3)(CH_2)_tCH_3$, —$(CH_2)_uCH(CH_3)_2$, —$C(CH_3)_3$, and —$(CH_2)_y$—$R_{21}$, wherein:
  s is 0, 1, 2 or 3;
  t is 1 or 2;
  u is 0 or 1;
  y is 0, 1 or 2;
  $R_{21}$ is selected from the group consisting of:

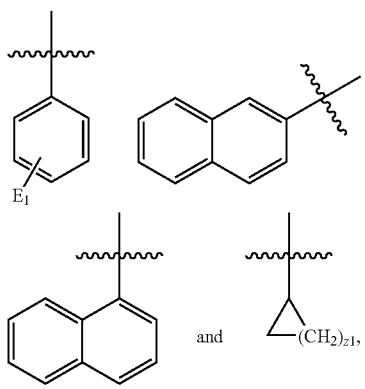

wherein z1 is 1, 2, 3 or 4; and
  $E_1$ is optionally present and selected from the group consisting of hydroxy and alkoxy;
$R_4$ and $R_5$ are each hydrogen;
$R_6$ is selected from the group consisting of hydrogen, —$(CH_2)_{aa}CH_3$, —$CH_2SCH_3$—$CH_2CH_2SCH_3$, —$(CH_2)_{bb}CH(CH_3)_2$, —$CH(CH_3)(CH_2)_{cc}CH_3$, —$(CH_2)_{dd}$—$NR_{22}R_{23}$, and —$(CH_2)_{ee}R_{24}$, wherein
  aa is 0, 1, 2 or 3;
  bb is 0 or 1;
  cc is 1 or 2;
  dd is 1, 2, 3 or 4;
  ee is 0, 1 or 2;
  $R_{22}$ and $R_{23}$ are independently selected from the group consisting of hydrogen, alkyl, substituted alkyl, formyl, acyl, amido, amidino, sulfonyl and sulfonamido;
  $R_{24}$ is selected from the group consisting of hydroxy, alkoxy

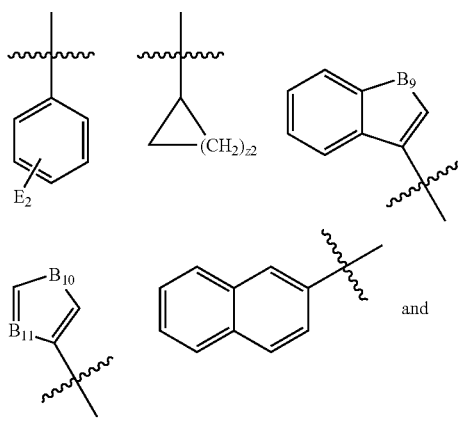

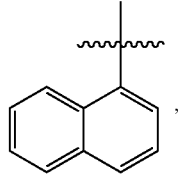

wherein $E_2$ is optionally present and is selected from the group consisting of hydroxy and alkoxy; $B_9$ and $B_{10}$ are independently selected from the group consisting of $NR_{14b}$, S and O, wherein $R_{14b}$ is selected from the group consisting of hydrogen, alkyl, substituted alkyl, formyl, acyl, carboxyalkyl, carboxyaryl, amido, sulfonyl and sulfonamido; $B_{11}$ is selected from N and CH; and z2 is 1, 2, 3 or 4; and
X is $NR_8$, wherein $R_8$ is selected from the group consisting of hydrogen, lower alkyl, substituted lower alkyl, formyl, acyl, carboxyalkyl, carboxyaryl, amido, sulfonyl, sulfonamido and amidino;
with the provisos that when $Z_1$, $Z_2$ and $Z_3$ are all NH, $R_1$ is:

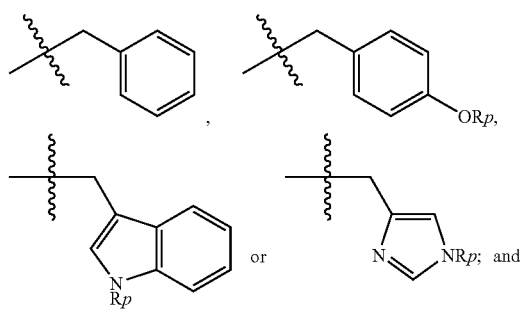

$R_2$ is:

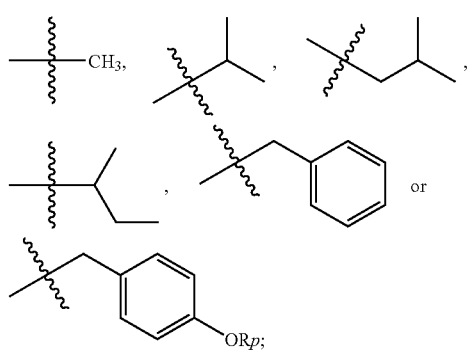

then $R_3$ is not:

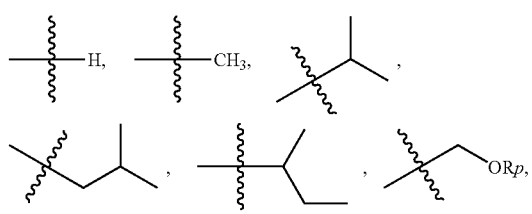

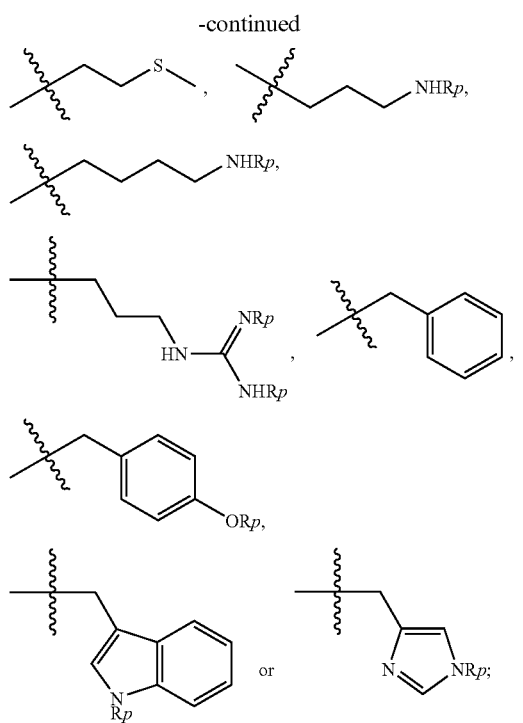
and when $Z_1$, $Z_2$ and $Z_3$ are all NH, $R_1$ is:
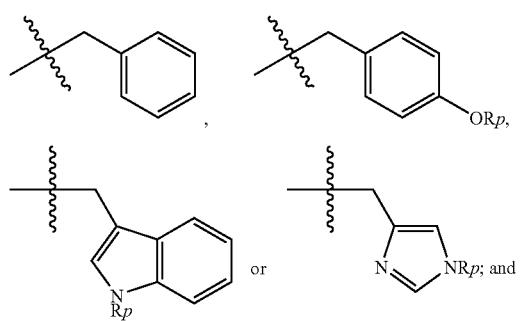
$R_3$ is:
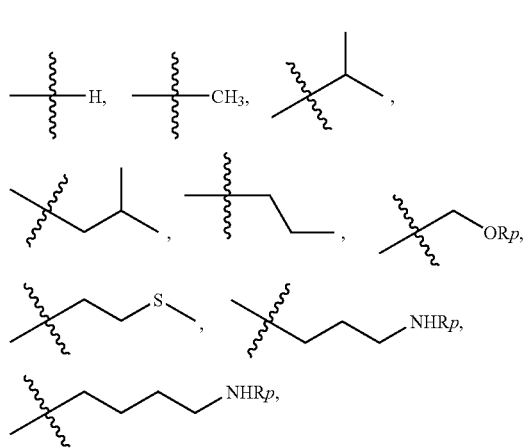
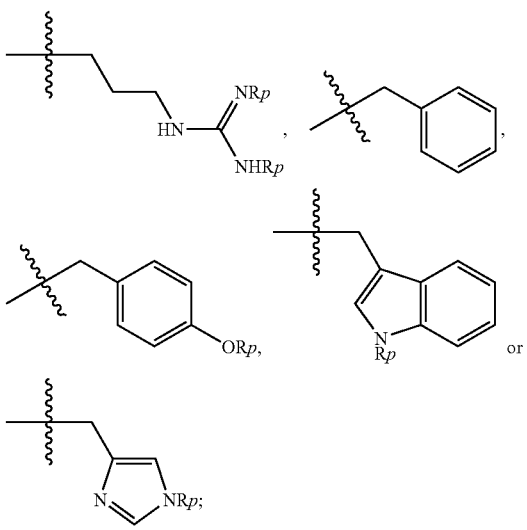
then $R_2$ is not:
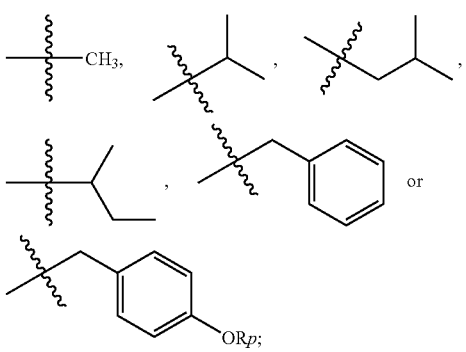
and when $Z_1$, $Z_2$ and $Z_3$ are all NH, $R_2$ is:
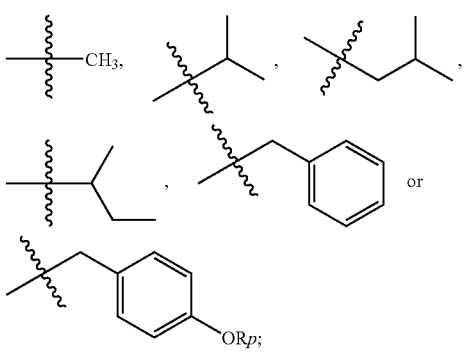
and $R_3$ is:
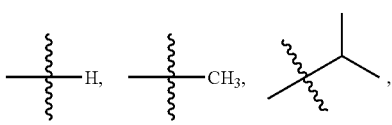

-continued

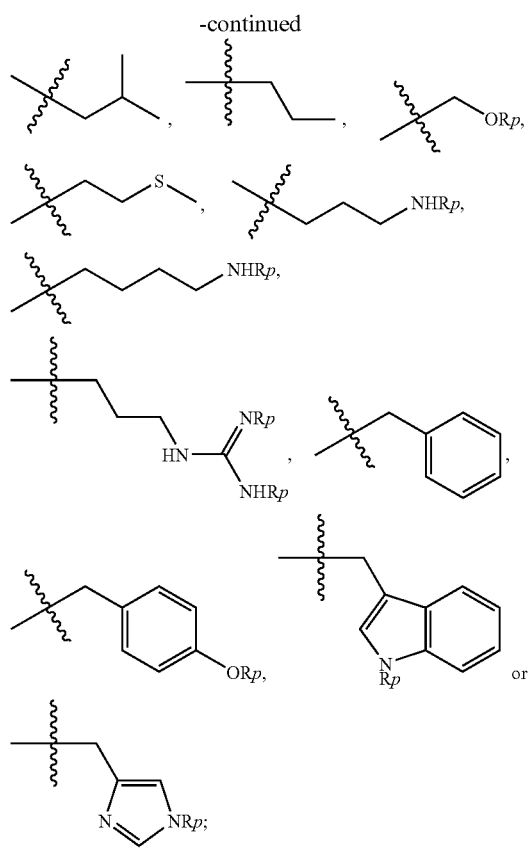

then R₁ is not:

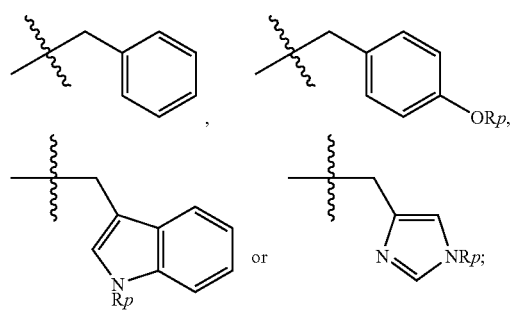

wherein Rp is hydrogen or a protecting group;
m, n₁ and p are 0; and
T is selected from the group consisting of:

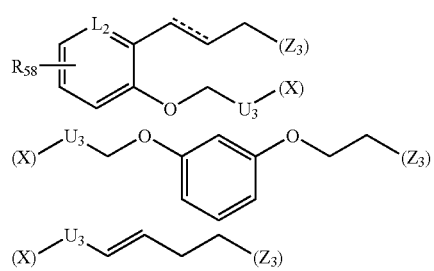

-continued

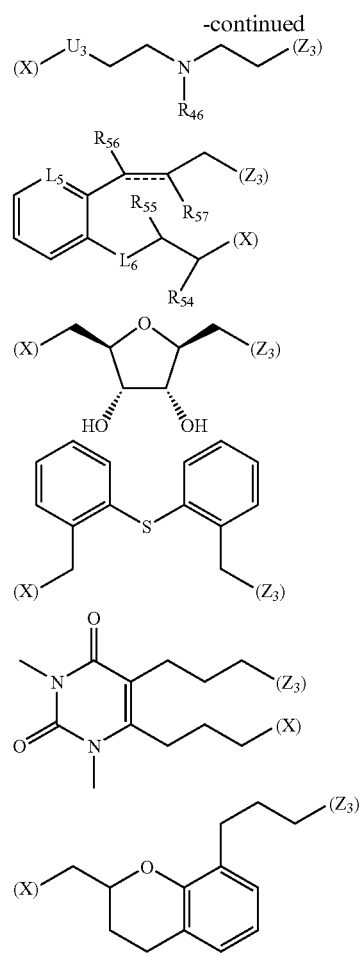

wherein
U₃ is CH₂;
L₂ is CH or N;
L₅ is CH or N;
L₆ is CR₅₂R₅₃ or O;
R₄₆ is H or CH₃;
R₅₄, R₅₅, R₅₆ and R₅₇ are independently selected from the group consisting of hydrogen and lower alkyl;
R₅₈ is selected from the group consisting of halogen and amidino; and
(X) is the site of a covalent bond to X in formula (I); and
(Z₃) is the site of a covalent bond to Z₃ in formula (I).

2. The compound of claim 1, wherein R₁₁ is selected from the group consisting of:

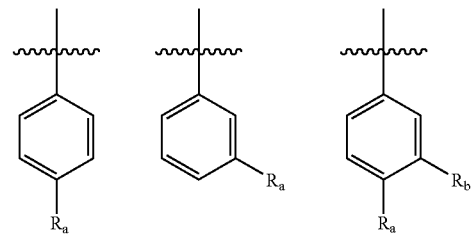

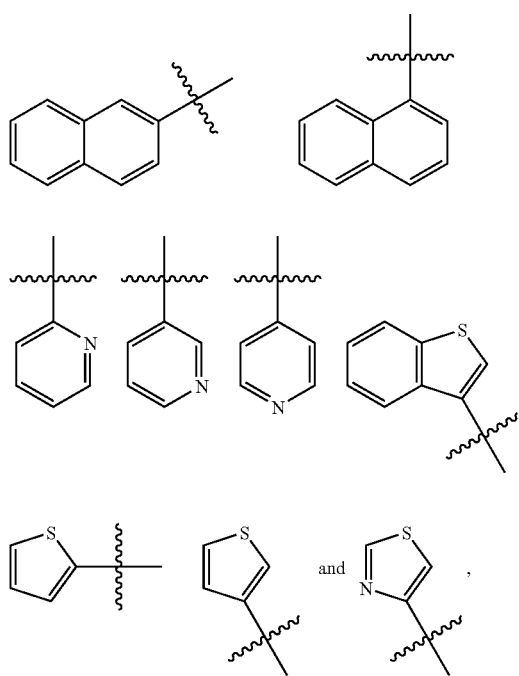
wherein $R_a$ and $R_b$ are independently selected from the group consisting of Cl, F, $CF_3$, $OCH_3$, OH, $CH_3$ and $C(CH_3)_3$.
3. The compound of claim 1 wherein m, n and p are 0; X, $Z_1$, $Z_2$ and $Z_3$ are NH; and $R_2$, $R_4$ and $R_5$ are hydrogen, represented by formula (III):
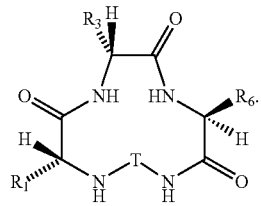
(III)
4. The compound of claim 1 selected from the group consisting of:
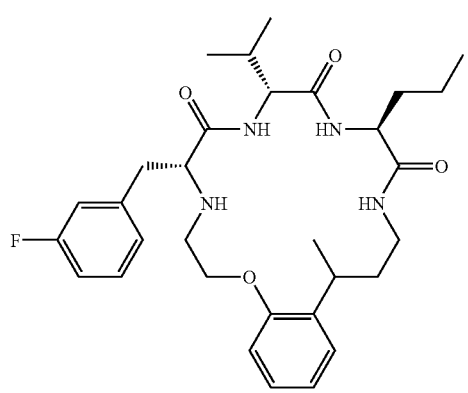
220
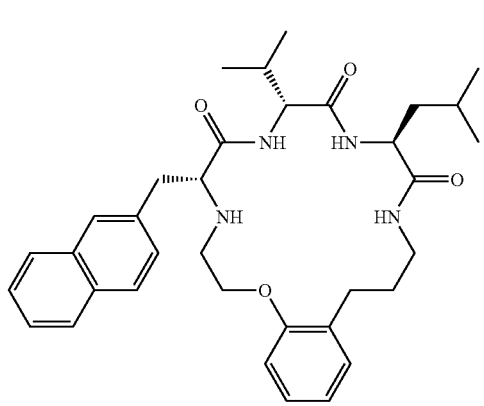
14
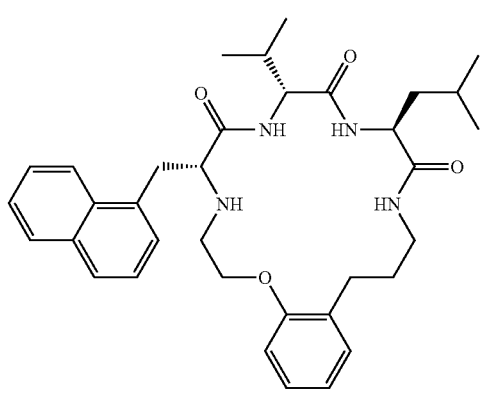
24
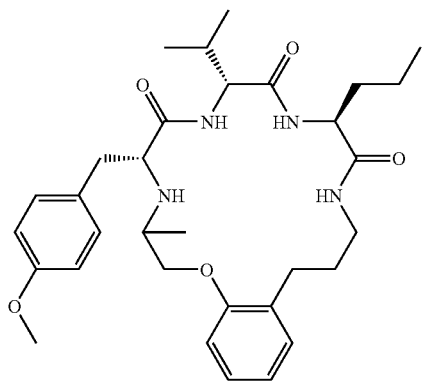
195
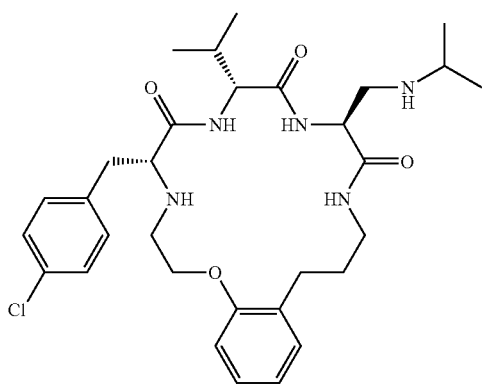
212

-continued
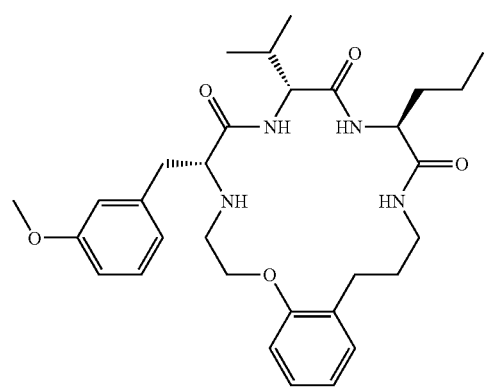
202
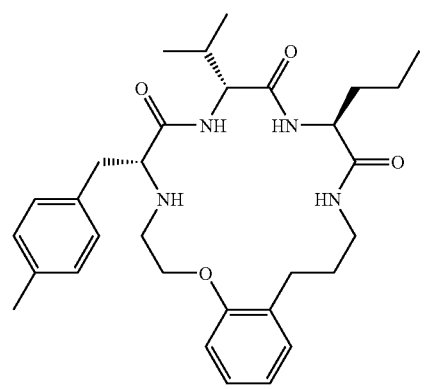
164
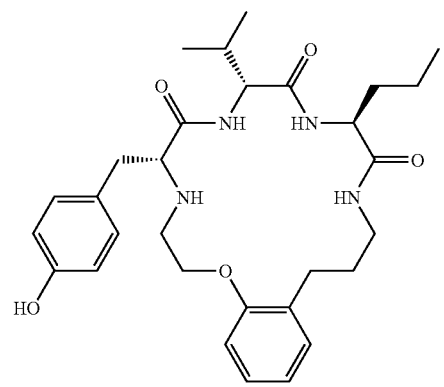
4
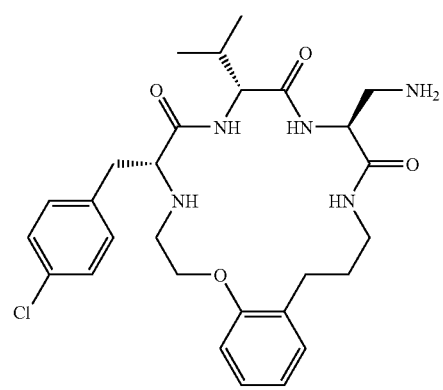
156
-continued
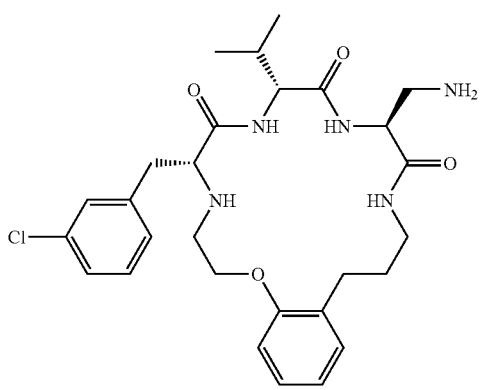
155
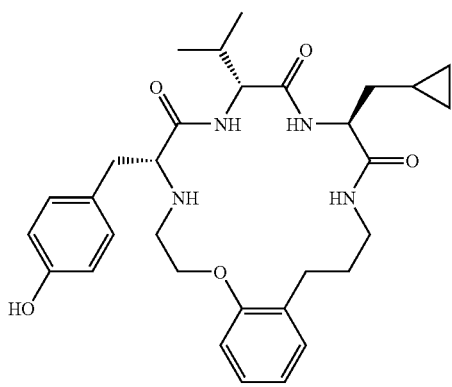
26
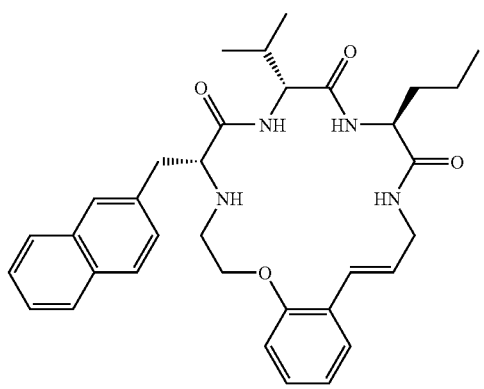
11
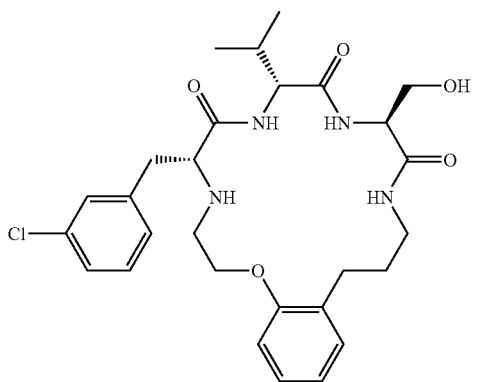
181

24
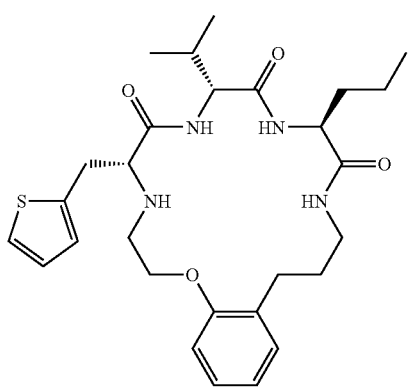
2
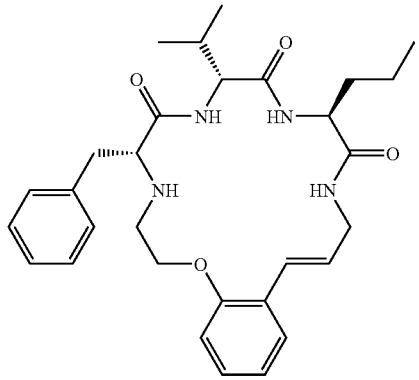
200
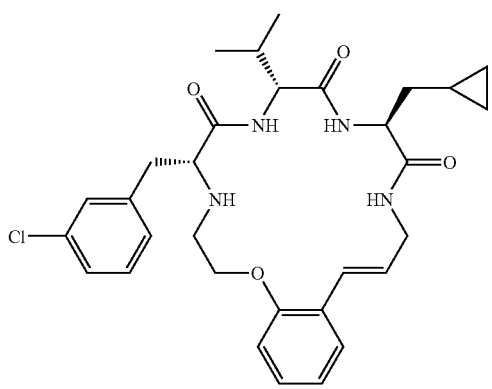
21
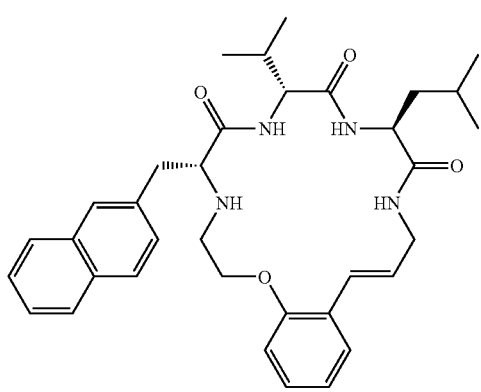
149
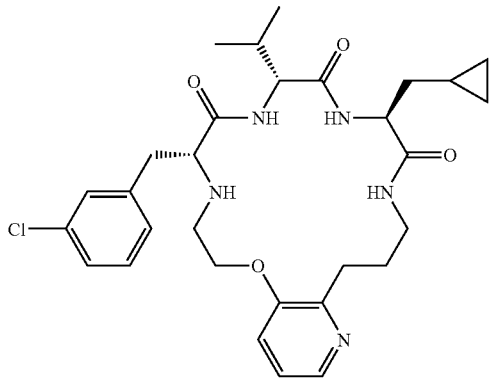
158
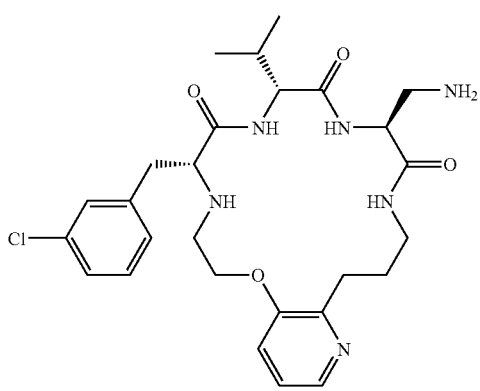
190
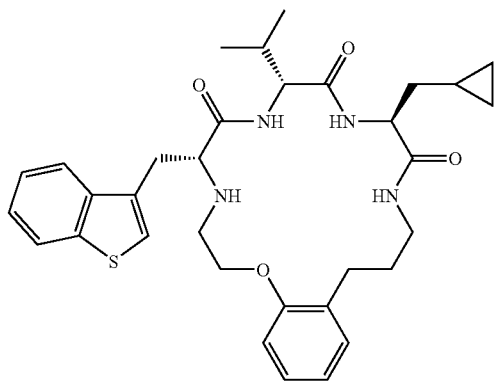
191
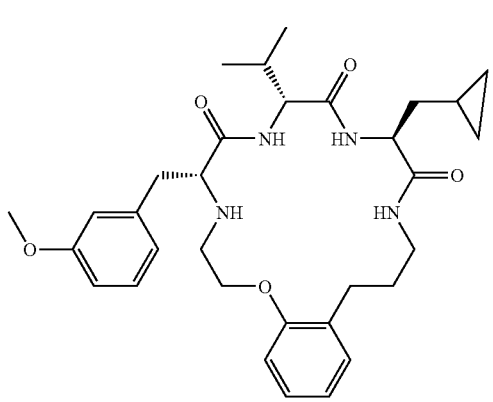

126
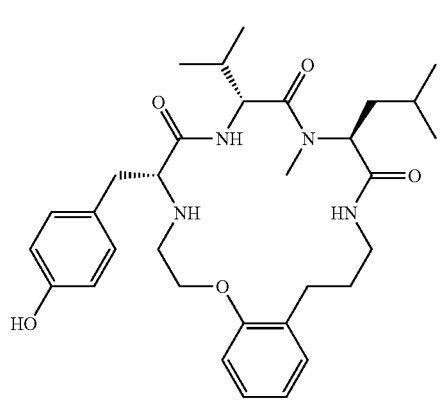
17
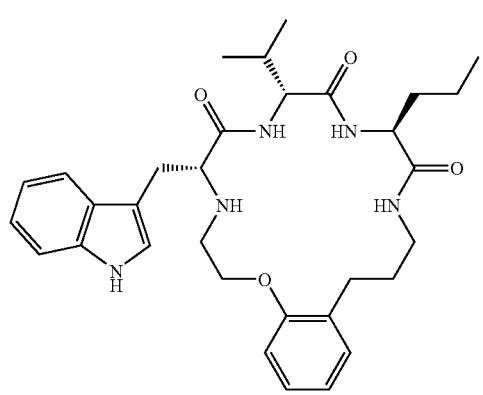
222
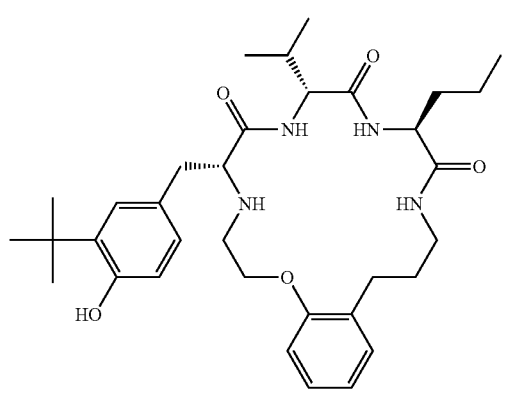
193
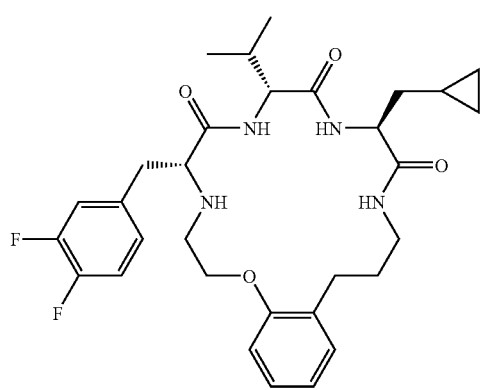
171
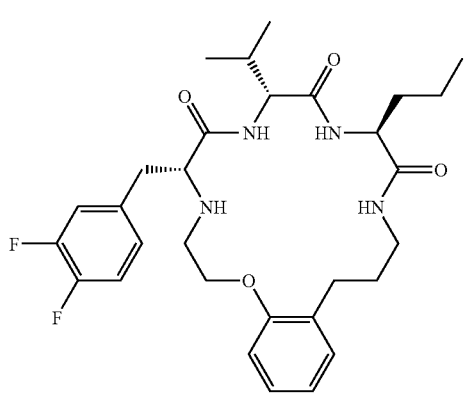
142
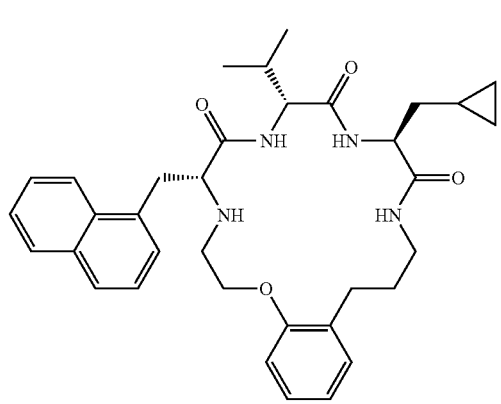
187
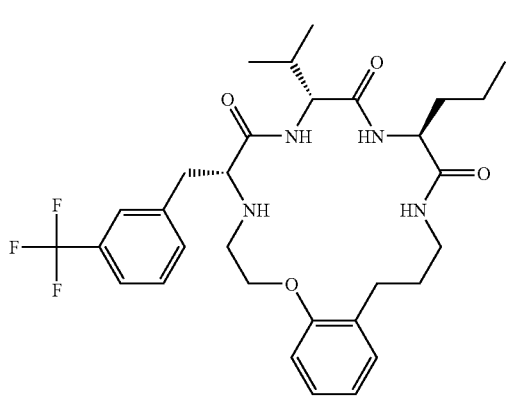
163
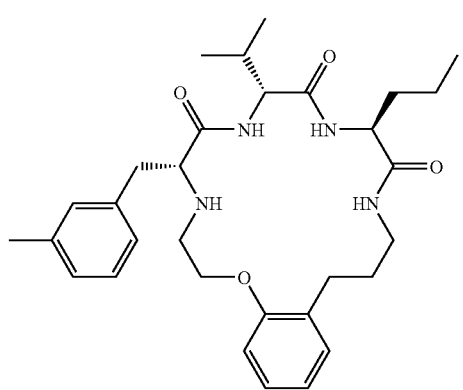

167
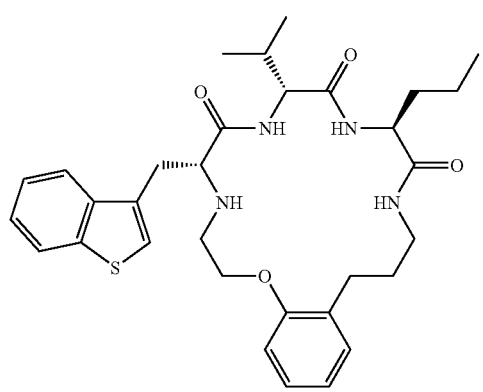
23
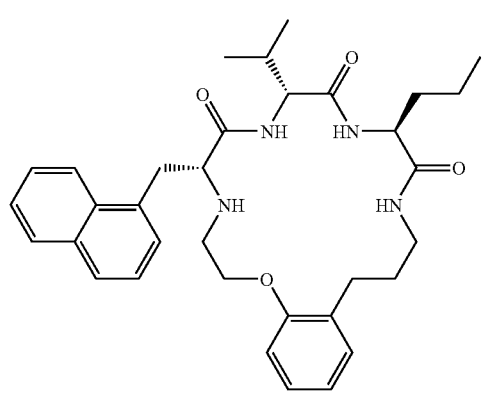
168
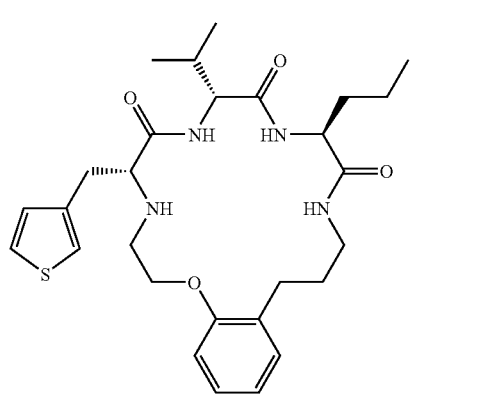
170
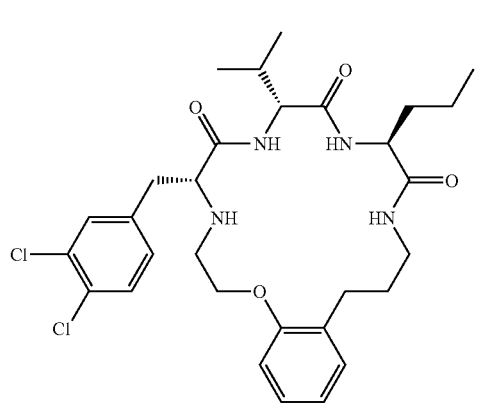
220
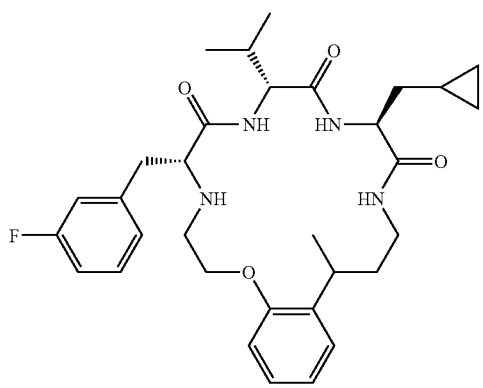
133
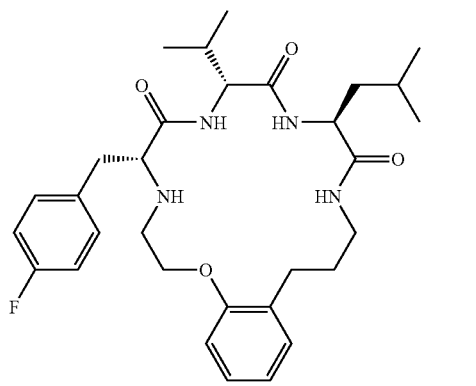
216
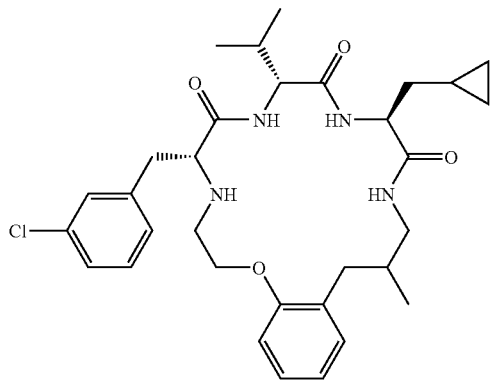
198
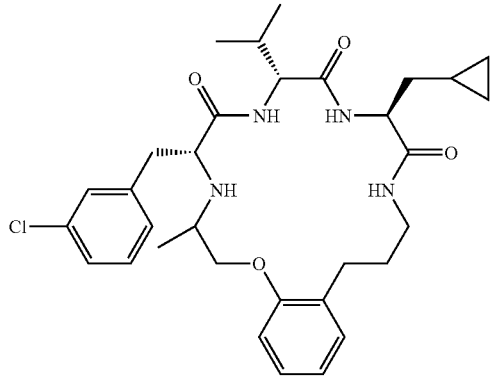

192
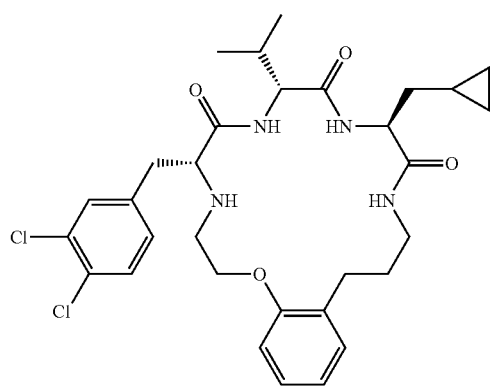
146
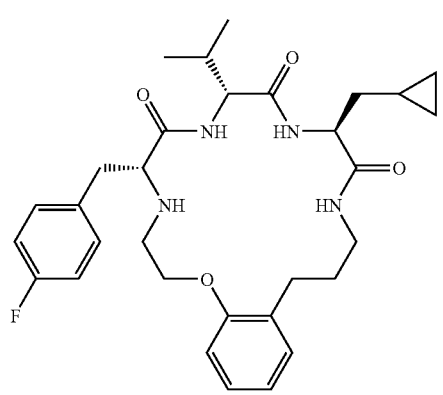
19
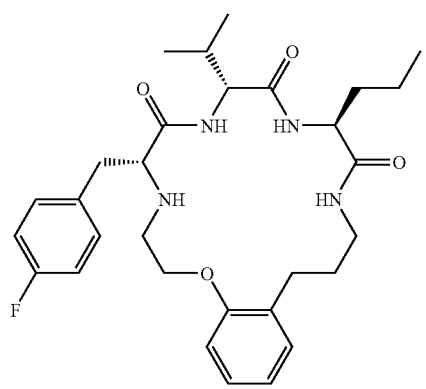
22
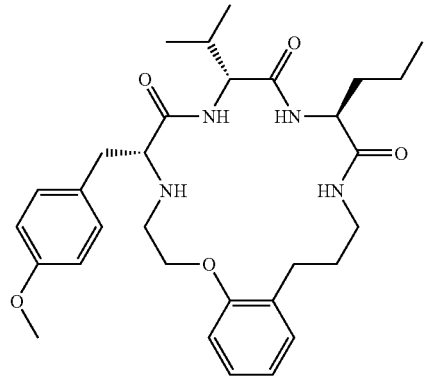
172
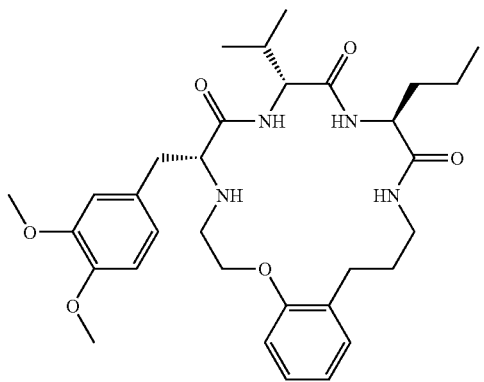
165
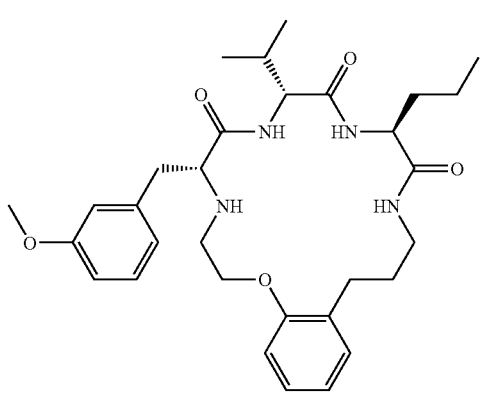
144
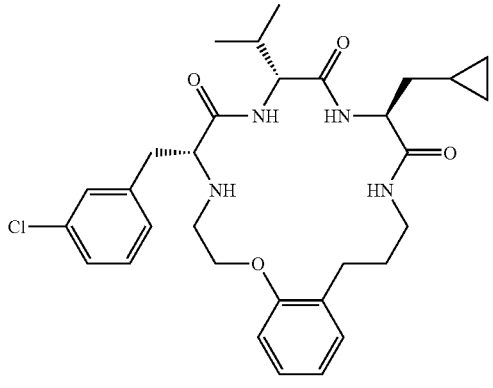
131
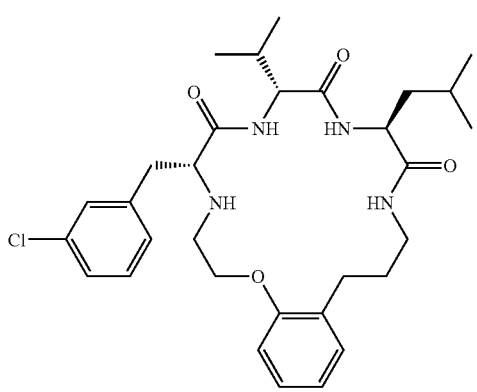

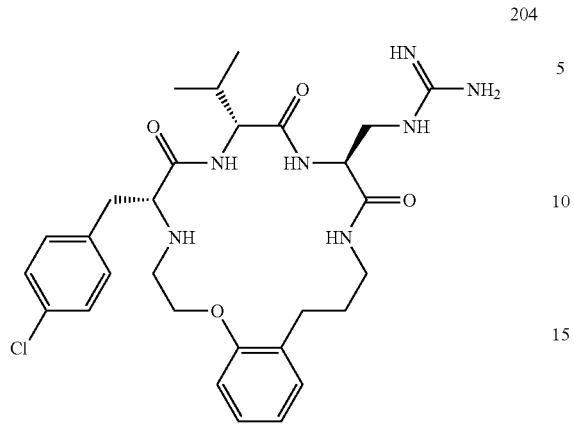
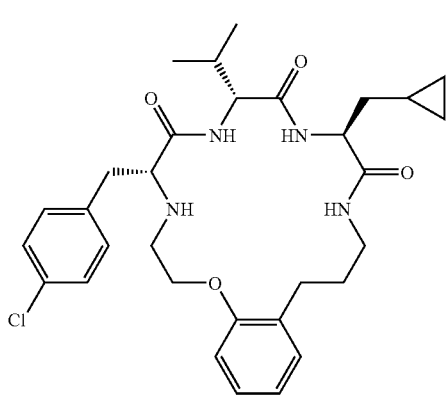

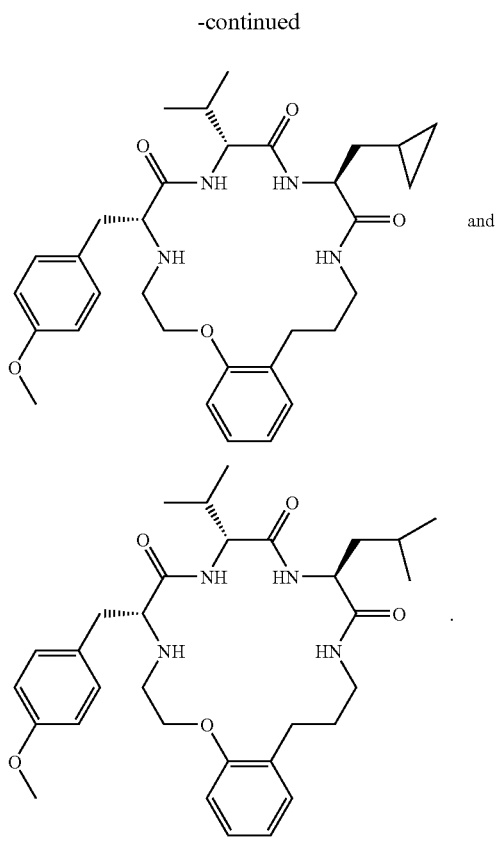

141 and

128

5. A compound represented by the general formula (I):

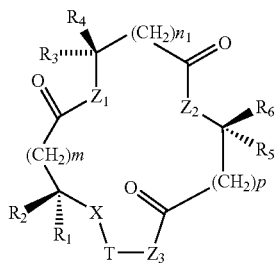
(I)

or pharmaceutically acceptable salts thereof wherein:

$Z_1$, $Z_2$, and $Z_3$ are independently $NR_{10}$, wherein $R_{10}$ is selected from the group consisting of hydrogen and lower alkyl;

$R_1$ is —$(CH_2)_q R_{11}$, wherein q is 0, 1 or 2, and $R_{11}$ is selected from the group consisting of:

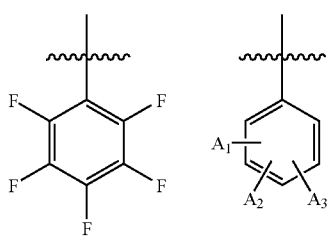

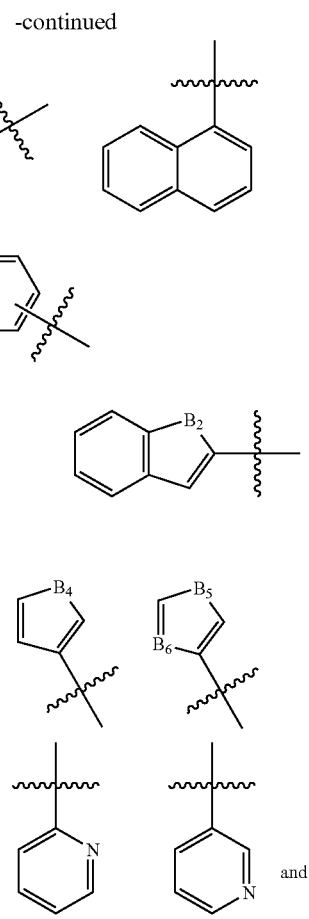

and wherein $A_1$, $A_2$ and $A_3$ are each optionally present and are independently selected from the group consisting of halogen, alkyl, substituted alkyl, trifluoromethyl, hydroxy, alkoxy and nitro;

$B_1$, $B_2$, $B_3$, $B_4$, $B_5$ and $B_7$ are independently $NR_{14a}$, S or O, wherein $R_{14a}$ is selected from the group consisting of hydrogen, alkyl, substituted alkyl, formyl, acyl, carboxyalkyl, carboxyaryl, amido, sulfonyl and sulfonamido;

$B_6$ and $B_8$ are independently N or CH;

$R_2$ is hydrogen;

$R_3$ is selected from the group consisting of: —$(CH_2)_s CH_3$, —$CH(CH_3)(CH_2)_t CH_3$, —$(CH_2)_u CH(CH_3)_2$, —$C(CH_3)_3$, and —$(CH_2)_y$—$R_{21}$, wherein:

s is 0, 1, 2 or 3;

t is 1 or 2;

u is 0 or 1;

y is 0, 1 or 2;

$R_{21}$ is selected from the group consisting of:

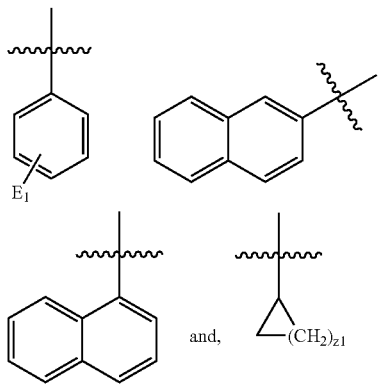

wherein z1 is 1, 2, 3 or 4; and
E₁ is optionally present and selected from the group consisting of hydroxy and alkoxy;

R₄ and R₅ are each hydrogen;

R₆ is each independently selected from the group consisting of hydrogen, —(CH₂)ₐₐCH₃, —CH₂SCH₃, —CH₂CH₂SCH₃, —(CH₂)ᵦᵦCH(CH₃)₂, —CH(CH₃)(CH₂)cccCH₃, —(CH₂)ddd—NR₂₂R₂₃, and —(CH₂)eeeR₂₄, wherein aa is 0, 1, 2 or 3;
bb is 0 or 1;
cc is 1 or 2;
dd is 1, 2, 3 or 4;
ee is 0, 1 or 2;

R₂₂ and R₂₃ are independently selected from the group consisting of hydrogen, alkyl, substituted alkyl, formyl, acyl, amido, amidino, sulfonyl and sulfonamido;

R₂₄ is selected from the group consisting of hydroxy, alkoxy

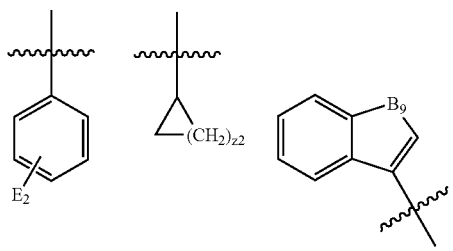

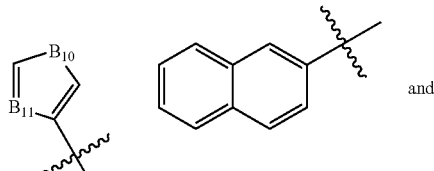

and

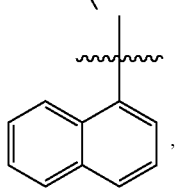

wherein E₂ is optionally present and is selected from the group consisting of hydroxy and alkoxy; B₉ and B₁₀ are independently selected from the group consisting of NR₁₄ᵦ, S and O, wherein R₁₄ᵦ is selected from the group consisting of hydrogen, alkyl, substituted alkyl, formyl, acyl, carboxyalkyl, carboxyaryl, amido, sulfonyl and sulfonamido; B₁₁ is selected from the group consisting of N and CH; and Z2 is 1, 2, 3 or 4; and X is NR₈, wherein R₈ is selected from the group consisting of hydrogen, lower alkyl, substituted lower alkyl, formyl, acyl, carboxyalkyl, carboxyaryl, amido, sulfonyl, sulfonamido and amidino;

with the provisos that when Z₁, Z₂ and Z₃ are all NH, R₁ is:

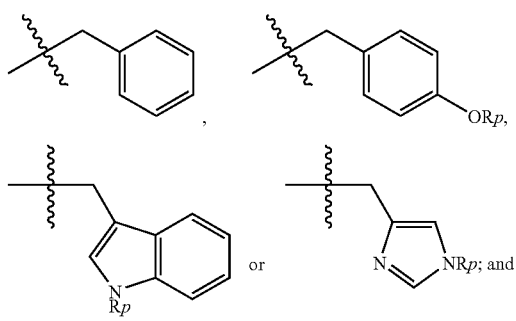

R₂ is:

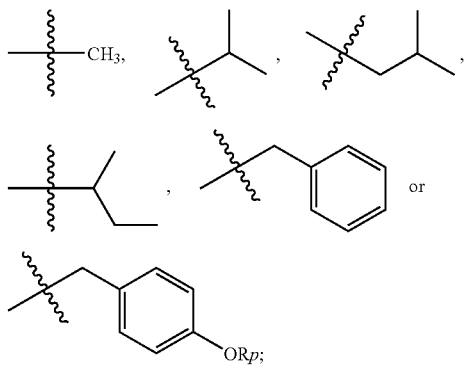

then R₃ is not:

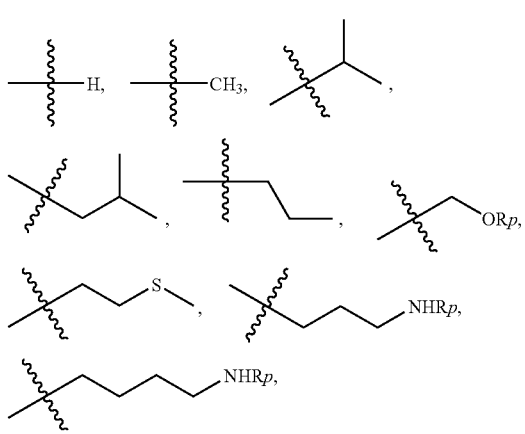

-continued
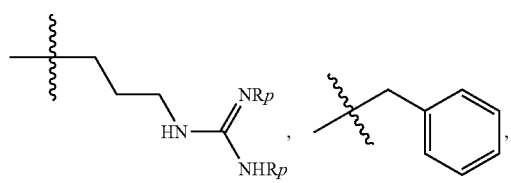,
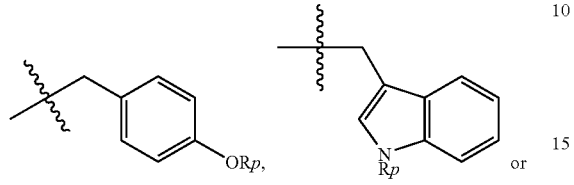
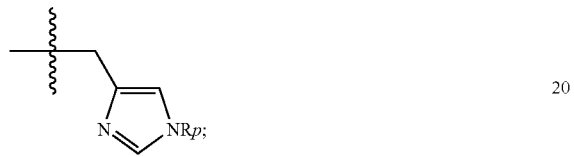;
and when $Z_1$, $Z_2$ and $Z_3$ are all NH, $R_1$ is:
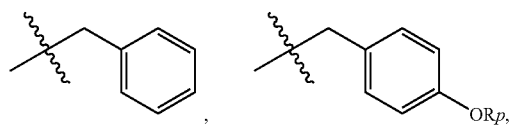,
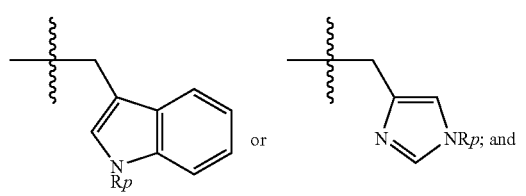
$R_3$ is:
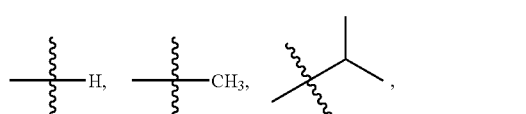
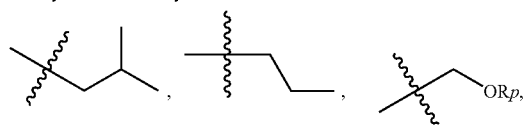
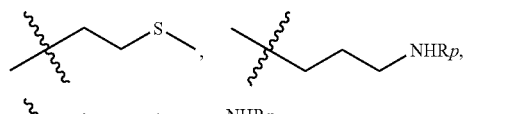
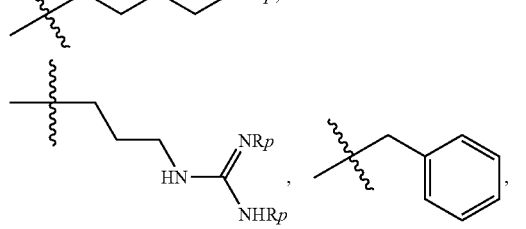,
-continued
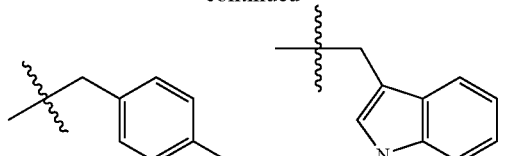
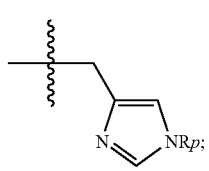;
then $R_2$ is not:
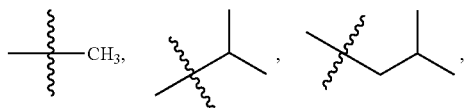,
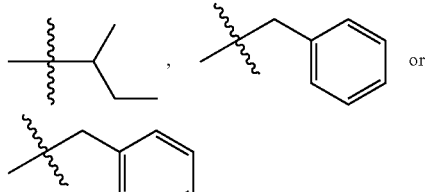;
and when $Z_1$, $Z_2$ and $Z_3$ are all NH, $R_2$ is:
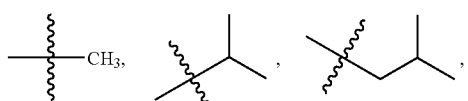,
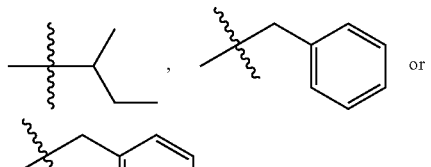;
and $R_3$ is:
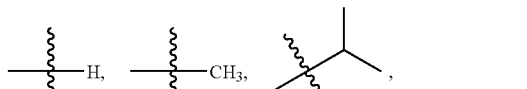
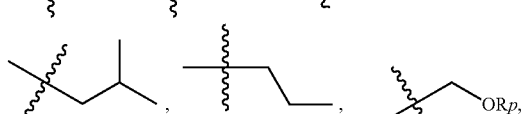
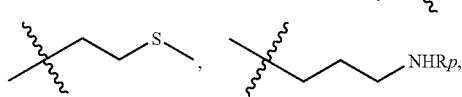

-continued
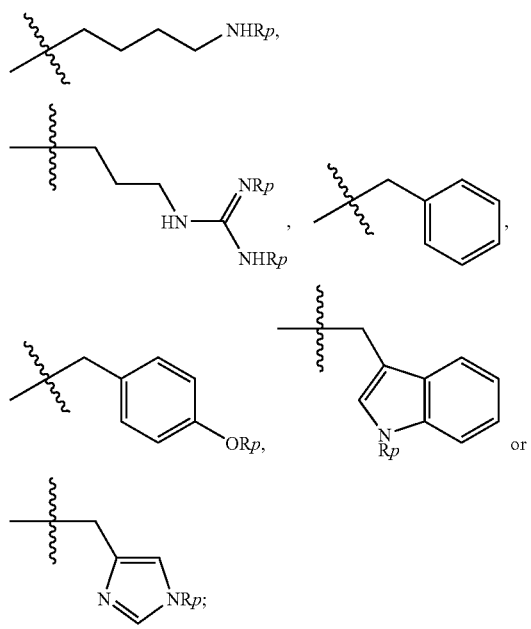
then R₁ is not:
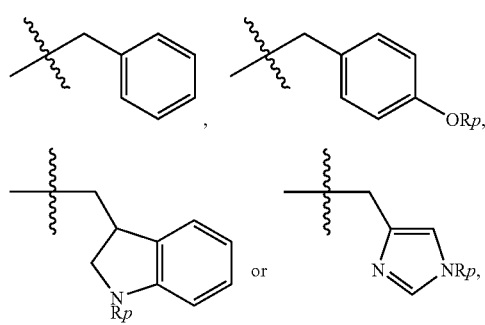
wherein Rp is hydrogen or a protecting group;
m, n, and p are 0; and
T is selected from the group consisting of:
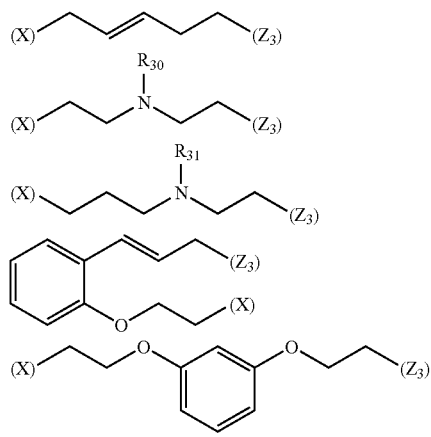
-continued
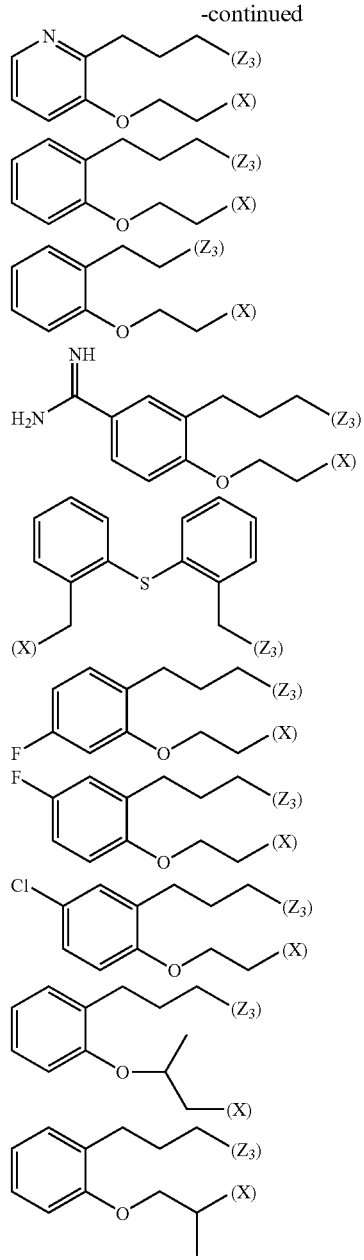

-continued

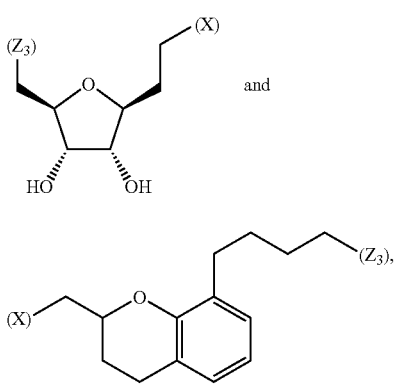

wherein $R_{30}$ and $R_{31}$ are independently selected from the group consisting of hydrogen and methyl; and (X) is the site of a covalent bond to X in formula (I); and ($Z_3$) is the site of a covalent bond to $Z_3$ in formula (I).

6. A pharmaceutical composition comprising:
(a) a compound of claim 1; and
(b) a pharmaceutically acceptable carrier.

7. A pharmaceutical composition, comprising:
(a) a compound of claim 4; and
(b) a pharmaceutically acceptable carrier.

8. A pharmaceutical composition, comprising:
(c) a compound of claim 5; and
(d) a pharmaceutically acceptable carrier.

9. A method of treating a gastrointestinal disorder associated with the motilin receptor or motility dysfunction in humans or other mammals comprising administering a therapeutically effective amount of a compound of claim 1.

10. A method of treating a gastrointestinal disorder associated with hyperotility or hypermotilinemia in humans or other mammals comprising administering a therapeutically effective amount of a compound of claim 1.

11. A method of treating irritable bowel syndrome or dyspepsia in humans or other mammals, comprising administering a therapeutically effective amount of a compound of claim 1.

12. A method of treating Crohn's disease, gastroesophogeal reflux disorders, ulcerative colitis, pancreatitis, infantile hypertrophic pyloric stenosis, carcinoid syndrome, malabsorption syndrome, diarrhea, atrophic colitis or gastritis, gastrointestinal dumping syndrome, postgastroenterectomy syndrome or celiac disease in humans or other mammals comprising administering a therapeutically effective amount of a compound of claim 1.

* * * * *

UNITED STATES PATENT AND TRADEMARK OFFICE
CERTIFICATE OF CORRECTION

PATENT NO. : 7,521,420 B2  
APPLICATION NO. : 10/872142  
DATED : April 21, 2009  
INVENTOR(S) : Fraser et al.

It is certified that error appears in the above-identified patent and that said Letters Patent is hereby corrected as shown below:

Column 4, line 2: Please correct "(=O) –, – (=ONH–,"
to read -- (=O) –, –C(=O) –NH– --

Column 80, Row T, compound 176: Replace the structure

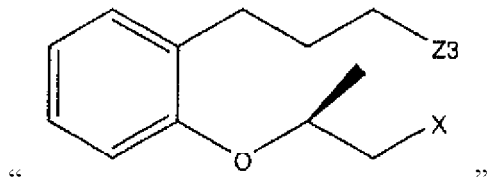

with the structure

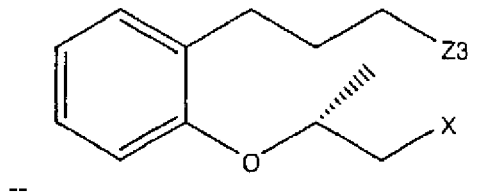

In the Claims:

Column 92, Claim 1, line 61: Please delete "and;"

Column 94, Claim 1, line 17: Please correct "$B_{11}$ is selected from N"
to read -- $B_{11}$ is selected from the group consisting of N --

Column 95, Claim 1, lines 55-60 and  
Column 97, Claim 1, lines 1-5: Replace the structure

with the structure

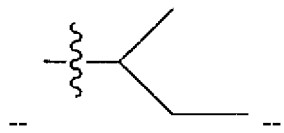

Column 114, Claim 5, line 62: Please correct "t is 1or 2;" to read -- t is 1 or 2; --

CERTIFICATE OF CORRECTION (continued)
U.S. Pat. No. 7,521,420 B2

Column 115, Claim 5, Line 23: Please correct "R₆ is each independently selected" to read -- R₆ is selected --

Column 116, Claim 5, lines 55-60;
Column 117, Claim 5, lines 50-55 and
Column 118, Claim 5, line 60-63: Replace the structure

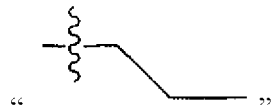

" "

with the structure

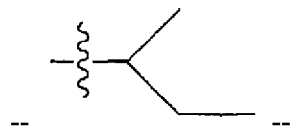

-- --

Column 119, Claim 5, line 40: Replace the structure

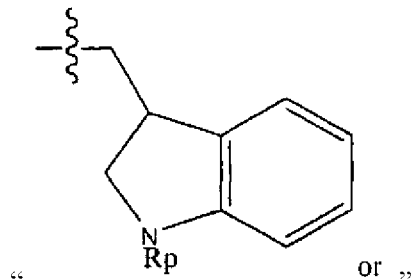

" or "

with the structure

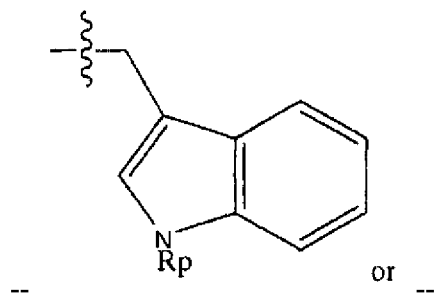

-- or --

Signed and Sealed this

Second Day of February, 2010

David J. Kappos
*Director of the United States Patent and Trademark Office*